US007122519B2

(12) United States Patent
Joullié et al.

(10) Patent No.: US 7,122,519 B2
(45) Date of Patent: Oct. 17, 2006

(54) DIDEMNIN ANALOGS AND FRAGMENTS AND METHODS OF MAKING AND USING THEM

(75) Inventors: Madeleine M. Joullié, Philadelphia, PA (US); Bo Liang, Glenolden, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 308 days.

(21) Appl. No.: 10/280,584

(22) Filed: Oct. 25, 2002

(65) Prior Publication Data

US 2003/0104991 A1 Jun. 5, 2003

Related U.S. Application Data

(62) Division of application No. 09/545,848, filed on Apr. 7, 2000, now Pat. No. 6,509,315.

(51) Int. Cl.
*A61K 38/00* (2006.01)
*A61K 38/12* (2006.01)
*C01K 16/00* (2006.01)

(52) U.S. Cl. ............... 514/10; 514/11; 530/317; 530/322; 530/323; 530/324; 530/402

(58) Field of Classification Search .......... 514/10, 514/11; 530/317, 322, 323, 324, 402
See application file for complete search history.

(56) References Cited

U.S. PATENT DOCUMENTS

| 4,160,452 | A | 7/1979 | Theeuwes |
| 4,256,108 | A | 3/1981 | Theeuwes |
| 4,265,874 | A | 5/1981 | Bonsen et al. |
| 4,493,796 | A | 1/1985 | Rinehart, Jr. |
| 4,782,135 | A | 11/1988 | Rinehart, Jr. |
| 5,137,870 | A | 8/1992 | Rinehart |
| 5,504,189 | A | 4/1996 | Emling et al. |
| 2003/0104991 | A1 | 6/2003 | Joullie et al. |

FOREIGN PATENT DOCUMENTS

| WO | WO 98/17275 A1 | 4/1998 |
| WO | WO 98/17302 A1 | 4/1998 |
| WO | WO 02/02596 A2 | 1/2002 |

OTHER PUBLICATIONS

Liang et al., J. Am. Chem. Soc., vol. 123, pp. 4469-4474, 2001.*
Vervoort et al., J. Org. Chem., vol. 65, pp. 782-792, 2000 (Published on Web Dec. 19 1999).*
Abdel-Magid et al., Synlett 537-539 (1990).
Abdel-Magid et al., Tetrahedron Lett. 31:5595-5598 (1990).
Campbell et al., Brit. J. Cancer 77(5):739-744 (1998).
Depenbrock et al., Brit. J. Cancer 78(6)::739-744 (1998).
Ewing et al., Tetrahedron 42:5863-5868 (1986).
Ewing et al., Tetrahedron Lett. 30(29):3757-3760 (1989).
Grubb et al., Biochem. Biophys. Res. Comm. 215:1130-1136 (1995).
Harris et al., Tetrahedron Lett. 28:2837-2840 (1987).
Harris et al., Tetrahedron 44:3489-3500 (1988).
Johnson et al., FEBS Lett. 383:1-5 (1996).
Johnson et al., Immunol. Cell Biol. 77:242-248 (1999).
Johnson et al., J. Cell Biochem. 72:269-278 (1999).
Li et al., J. Am. Chem. Soc. 112:7659-7672 (1990).
Li et al., Studies in Natural Products Chem. 10:241-302 (1992).
Liang et al., Org. Lett. 1:1319-1322 (1999).
Mayer et al., J. Org. Chem. 59:5192-5205 (1994).
Mayer et al., Tetrahedron, Asymmetry 5:519-522 (1994).
Pfizenmayer et al., Bioorg. Med. Chem. Lett. 8:3653-3656 (1998).
Sakai et al., J. Med. Chem. 39:2819-2834 (1996).
Schumacher et al., Tetrahedron, Asymmetry 9:47-53 (1997).
Wipf, Chem. Rev. 95:2115-2134 (1995).
STNEasy/CAplus English language abstract of document FP1, ES2102322A1, Accession No. 1998:169709.
Gemma Jou, et al., "Total Synthesis of Dehydrodidemnin B. Use of Uronium and Phosphonium Salt Coupling Reagents in Peptide Synthesis in Solution, " *J. Org. Chem.* 62:354-366 (Am. Chem. Society 1997).
Copy of Communication pursuant to Article 96(2) EPC for European Patent Application No. 01 924 886.3, European Patent Office, Netherlands (Aug. 2004).
Ahuja, D., et al., "Inhibition of Protein Synthesis by Didemnins: Cell Potency and SAR,"*J. Med. Chem.* 43:4212-4218, American Chemical Society (Nov. 2000).
Ahuja, D., et al., "Inhibition of Protein Synthesis by Didemnin B: How EF-1α Mediates Inhibition of Translocation," *Biochemistry* 39:4339-4346, American Chemical Society (Apr. 2000).
Crews, C. M., et al., "Didemnin Binds to the Protein Palmitoyl Thioesterase Responsible for Infantile Neuronal Ceroid Lipofuscinosis," *Proc. Natl. Acad. Sci. USA* 93:4316-4319, National Academy of Sciences (1996).
Ding, X., et al., "Structure-Activity Relationships of Side-Chain Modified Didemnins," *Bioorg. Med. Chem. Lett. 11*:231-234, Pergamon Press (Jan. 2001).
Joullié, M. M., et al., "Total Synthesis of (−)-Tamandarin B," *Tetrahedron Letters 41*:9373-9376 Elsevier Science Ltd. (2000).
Joullié, M.M., et al., "Chemical Defense in Ascidians of the Didemnidae Family," *Bioconjugate Chem. 14*:30-37, American Chemical Society (Jan.-Feb. 2003).
Liang, B., et al., "Total Synthesis of [(2S)-Hiv$^2$] Didemnin M," *J. Org. Chem.* 65:4762-4765, American Chemical Society (Jul. 2000).
Mayer, S., et al., "Synthetic Routes to a Constrained Ring Analog of Didemnin B," *J. Org. Chem.* 61:1655-1664, American Chemical Society (1996).

(Continued)

*Primary Examiner*—Jon Weber
*Assistant Examiner*—Abdel A. Mohaed
(74) *Attorney, Agent, or Firm*—Sterne, Kessler, Goldstein & Fox P.L.L.C.

(57) ABSTRACT

The present invention relates to macrocyclic depsipeptides, including didemnin analogs and fragments thereof, which are useful as anti-cancer agents and for other purposes. The invention includes numerous didemnin analogs and fragments and methods of making them. Methods of using these compounds as inhibitors of protein synthesis, cell growth, and tumorigenesis and as enhancers of apoptosis are also provided.

25 Claims, 55 Drawing Sheets

OTHER PUBLICATIONS

Mayer, S., et al., "The Cyclic Depsipeptide Backbone of the Didemnins," *Acta Cryst. C51*:1609-1614, Blackwell Publishing (1995).

Pfizenmayer, A.J., et al., "Synthesis and Biological Activities of [*N*-MeLeu$^5$] Didemnin B," *Biog. Med. Chem. Lett.* 6:2713-2716, Pergamon Press (1996).

Pfizenmayer, A.J., et al., "Synthesis and Biological Activites of [*N*-MeLeu$^5$]- and [N-MePhe$^5$]- Didemnin B," *Tetrahedron* 55:313-334, Pergamon Press (Jan. 1999).

Portonovo, P., et al., "First Total Synthesis of a Fluorescent Didemnin," *Tetrahedron* 56:3687-3690, Pergamon Press (Jun. 2000).

Ramanjulu, J.M., et al., "Synthetic Studies of a Didemnin B Analog Based on a 2,3-Diamino Sugar Scaffolding," *Journal of the Chinese Chemical Society* 48:1-4, The Chemical Society (Taipei) (2001).

Ramanjulu, J.M., et al., "Syntheses of Acyclic Analogs of Didemnin B," *Synthetic Communications* 27:3259-3272, Marcel Dekker, Inc. (1997).

Ramanjulu, J.M., et al., "Synthesis of a Reduced Ring Analog of Didemnin B," *J. Org. Chem.* 62:4961-4969, American Chemical Society (1997).

Ramanjulu, J.M., et al., "Analogs of the β-Turn of the Cyclodepsipeptide Didemnin B," *Tetrahedron Letters* 37:311-314, Pergamon Press (1996).

Ramanjulu, J.M., et al., "A Facile Synthesis of Benzyl 2-Amino-3-Azido-4-*O-p*-Methoxybenzyl-6-*O*-Benzyl-2,3-Dideoxy-α-D-Glucopyranoside: A Key Intermediate in the Formation of a Didemnin B Analog," *J. Carbohydrate Chemistry* 15:371-381, Marcel Dekker, Inc. (1996).

Tarver, J.E., et al., "Total Syntheses of Conformationally Constrained Didemnin B Analogues. Replacements of *N, O*-Dimethyltyrosine with L-1,2,3-4-Tetrahydroisoquinoline and L-1,2,3,4-Tetrahydro-7-methoxyisoquinoline," *J. Org. Chem.* 66:7575-7587, American Chemical Society (Nov. 2001).

Vera, M.D., et al., "Synthesis and Biological Evaluation of Didemnin Photoaffinity Analogues," *Biorg. Med. Chem. Lett.* 11:1871-1874, Pergamon Press (Jul. 2001).

Vera, M.D., et al., "Natural Products as Probes of Cell Biology: 20 Years of Didemnin Research," *Medicinal Research Reviews* 22:102-145, John Wiley & Sons, Inc. (Mar. 2002).

Vera, M.D., et al., "[Lys$^3$] Didemnins as Potential Affinity Ligands," *Biorg. Med. Chem. Lett.* 11:13-16, Pergamon Press (Jan. 2001).

Xiao, D., et al., "Total Synthesis of a Conformationally Constrained Didemnin B," *J. Org. Chem.* 66:2734-2742, American Chemical Society (Apr. 2001).

\* cited by examiner

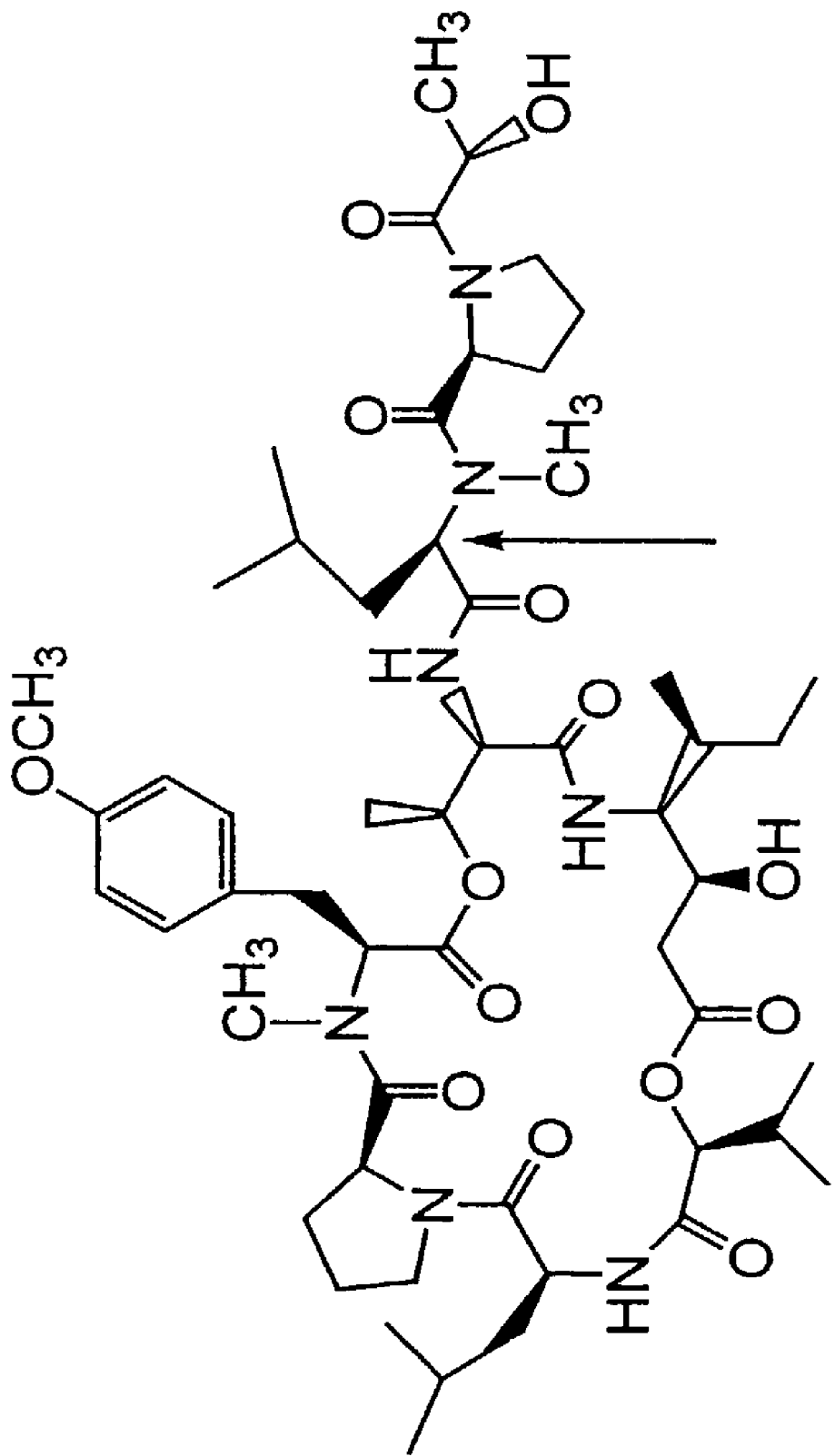
Fig. 1A

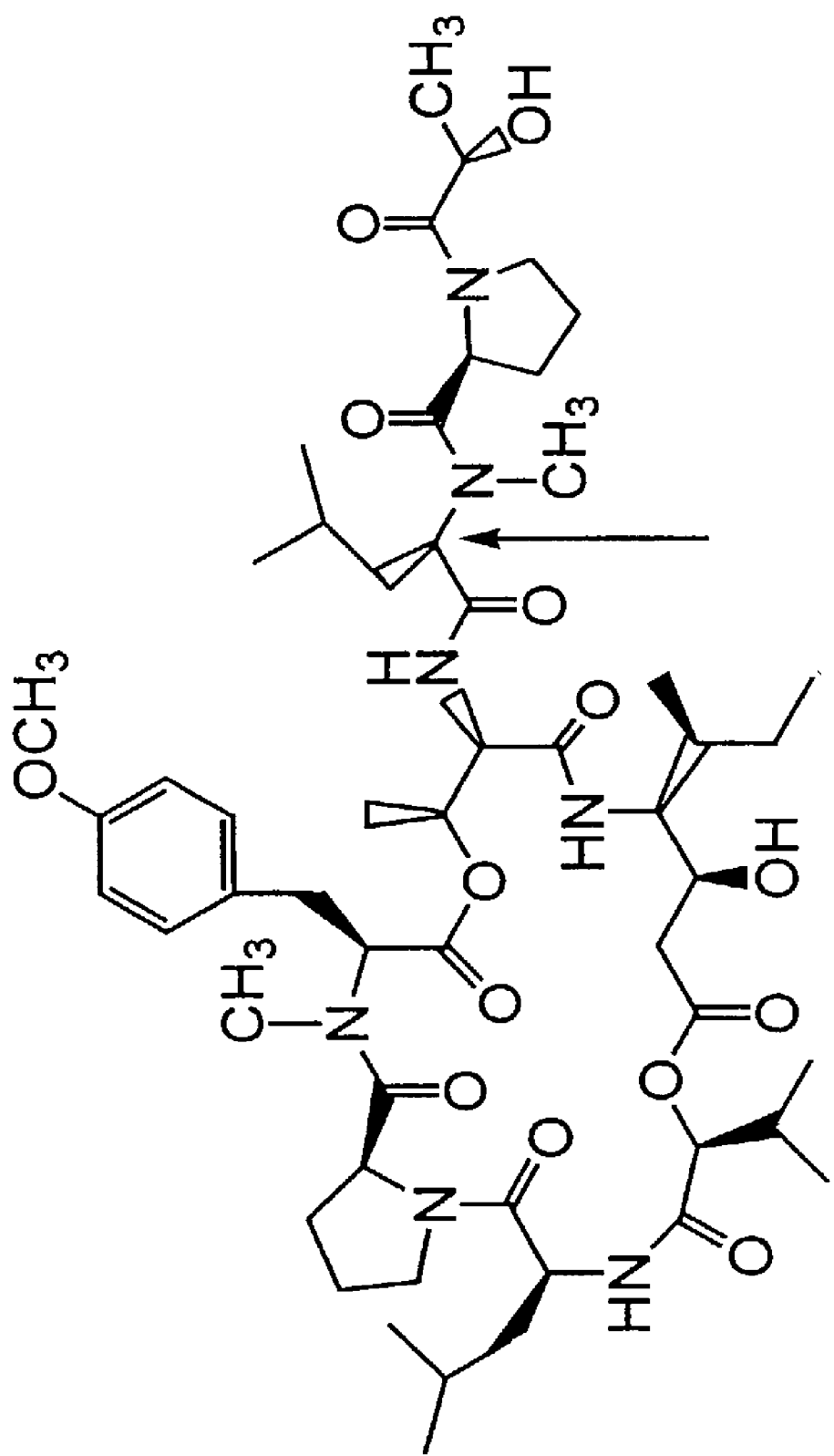
Fig. 1B

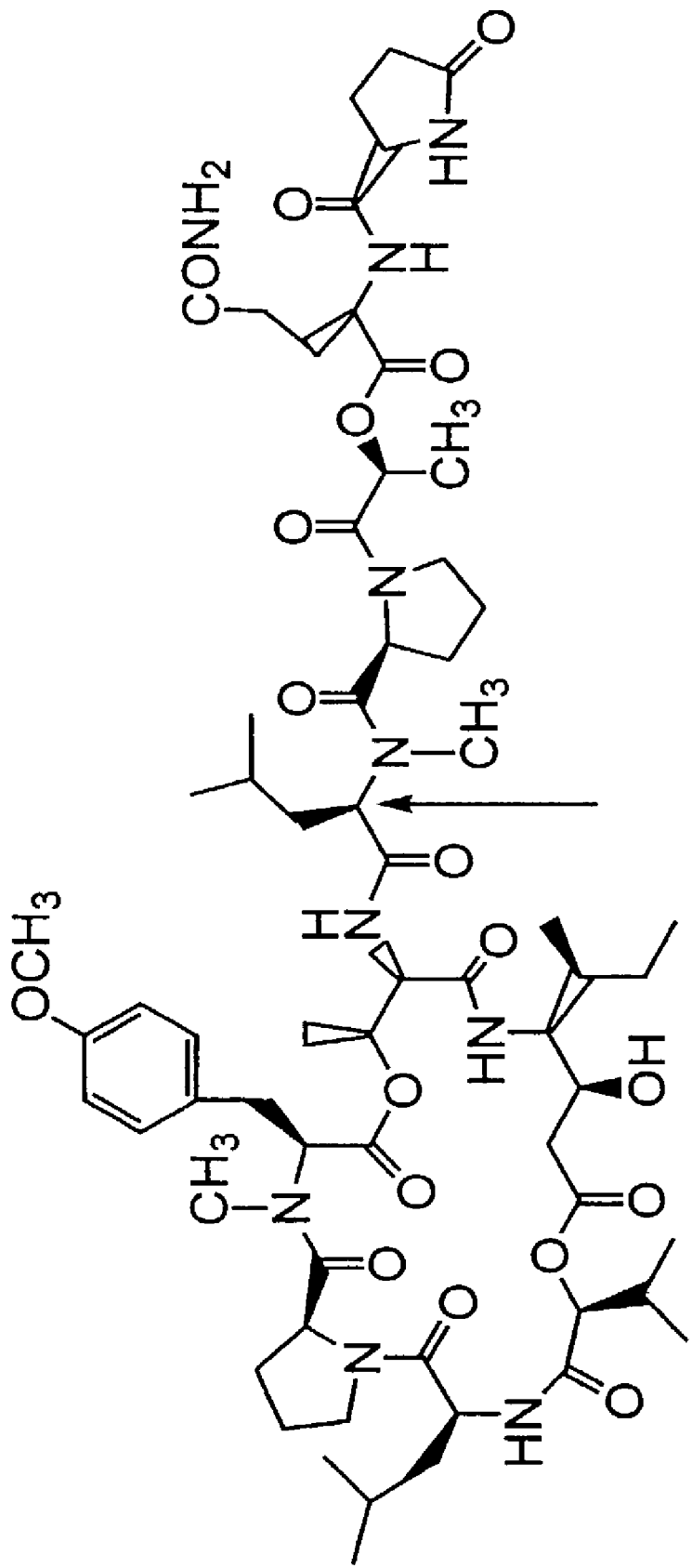
Fig. 2A

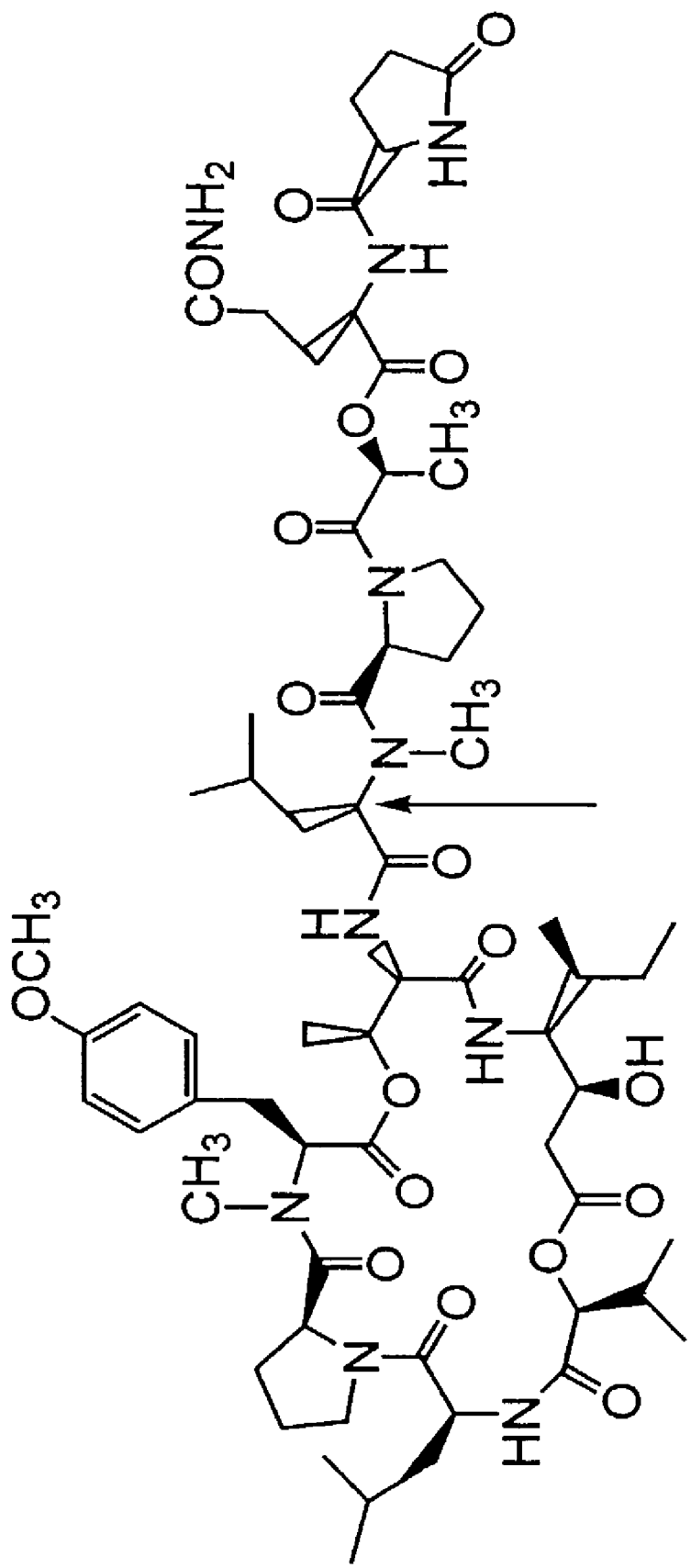
Fig. 2B

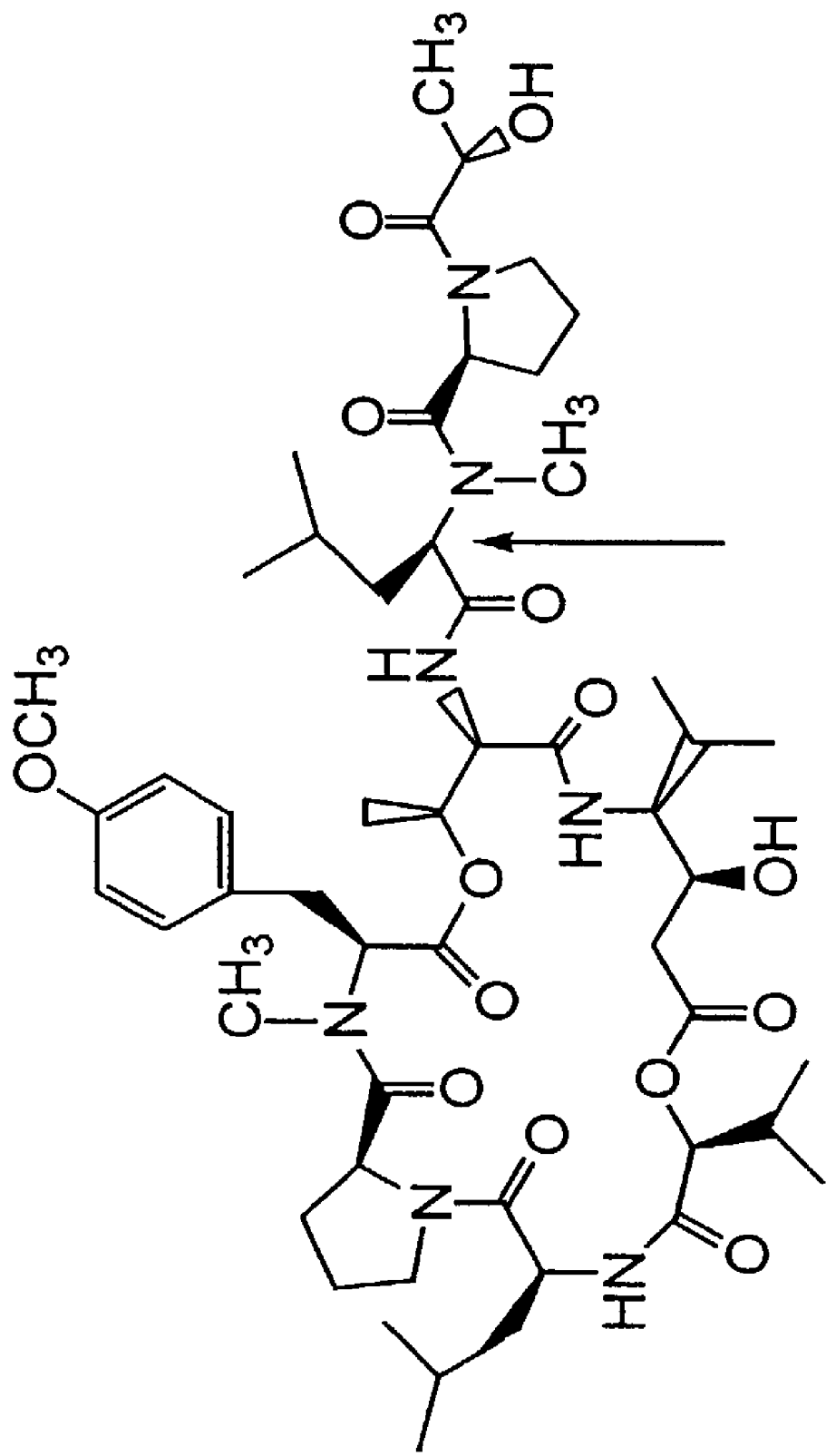
Fig. 3A

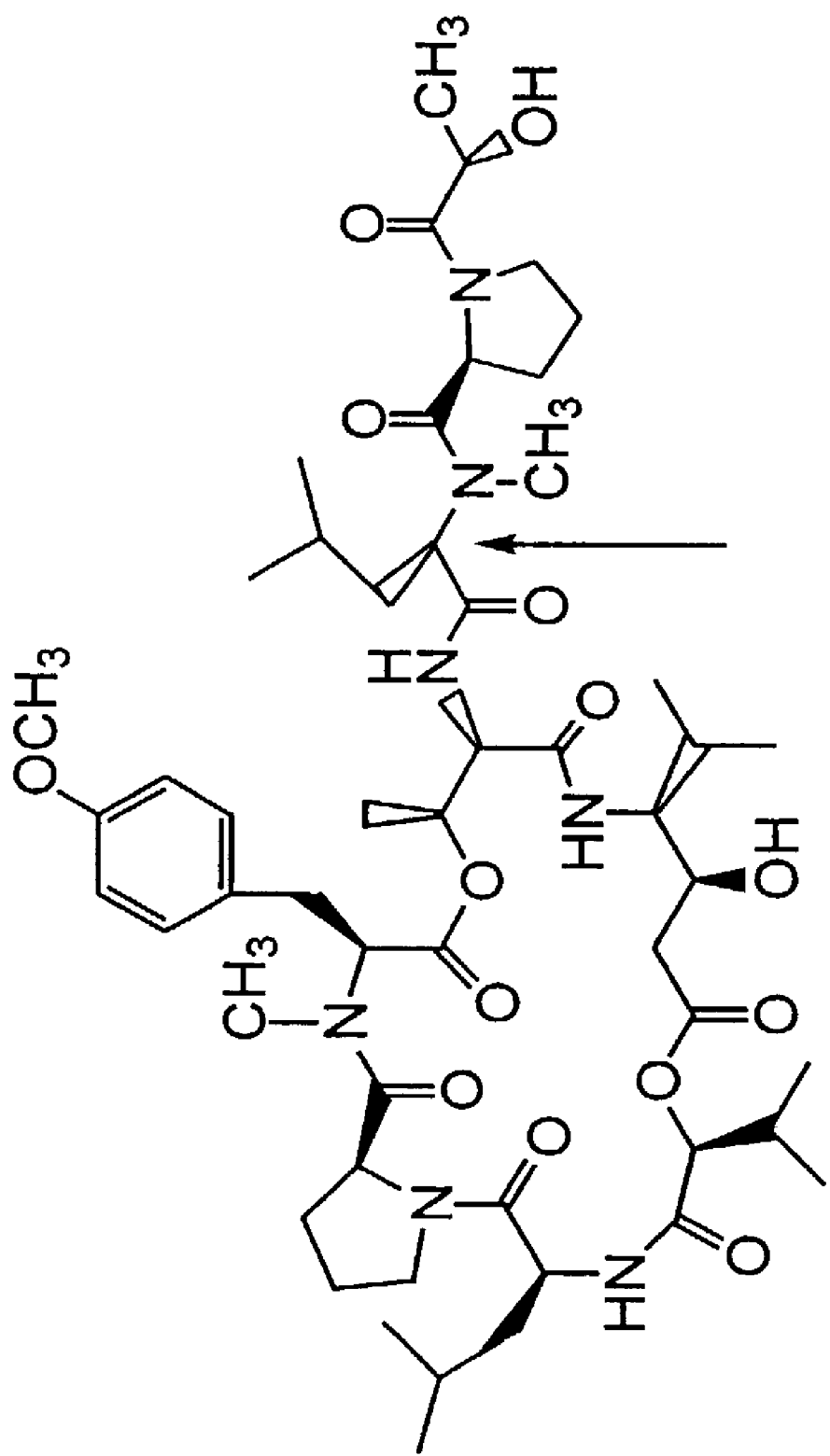
Fig. 3B

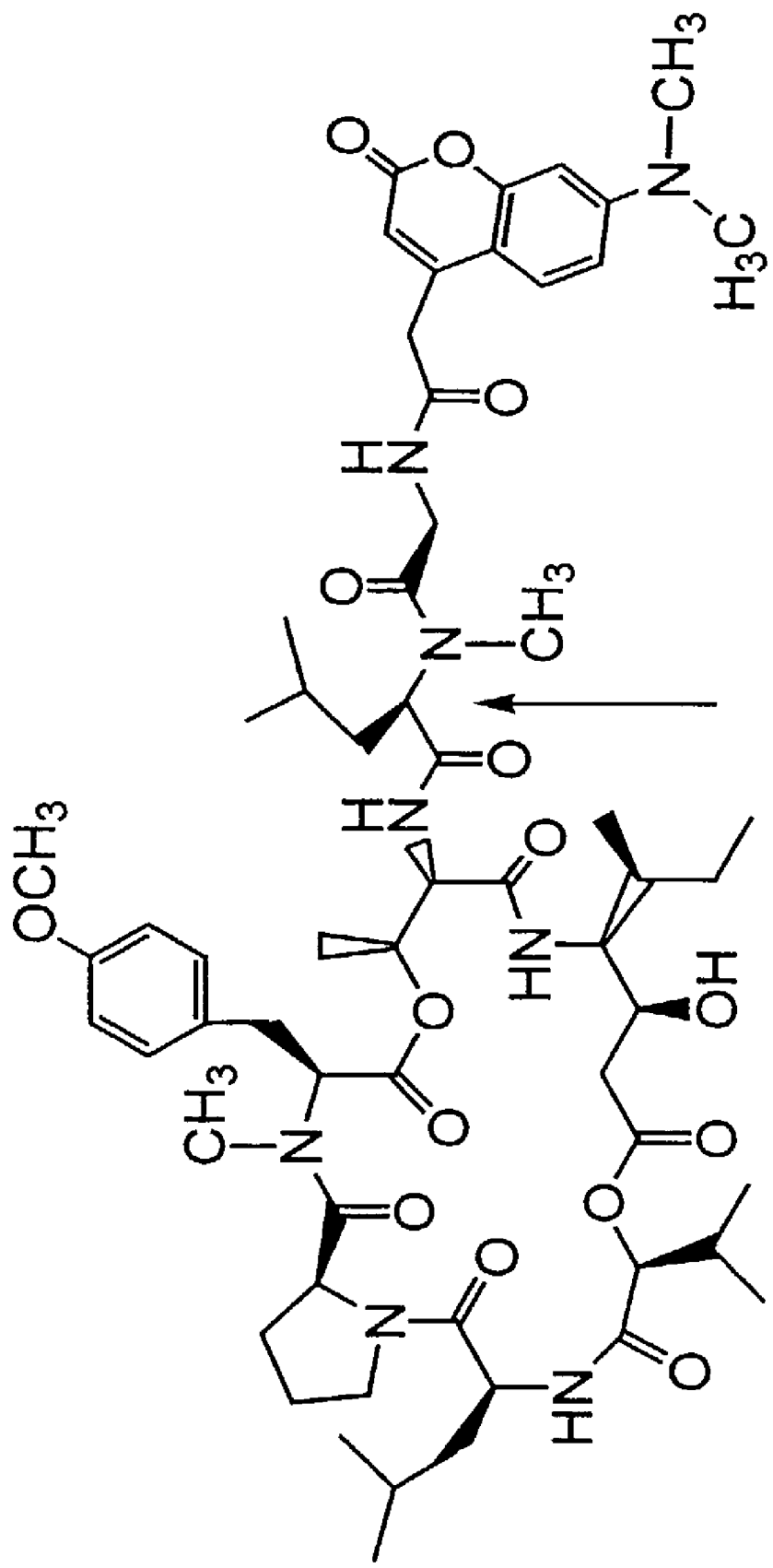
Fig. 4A

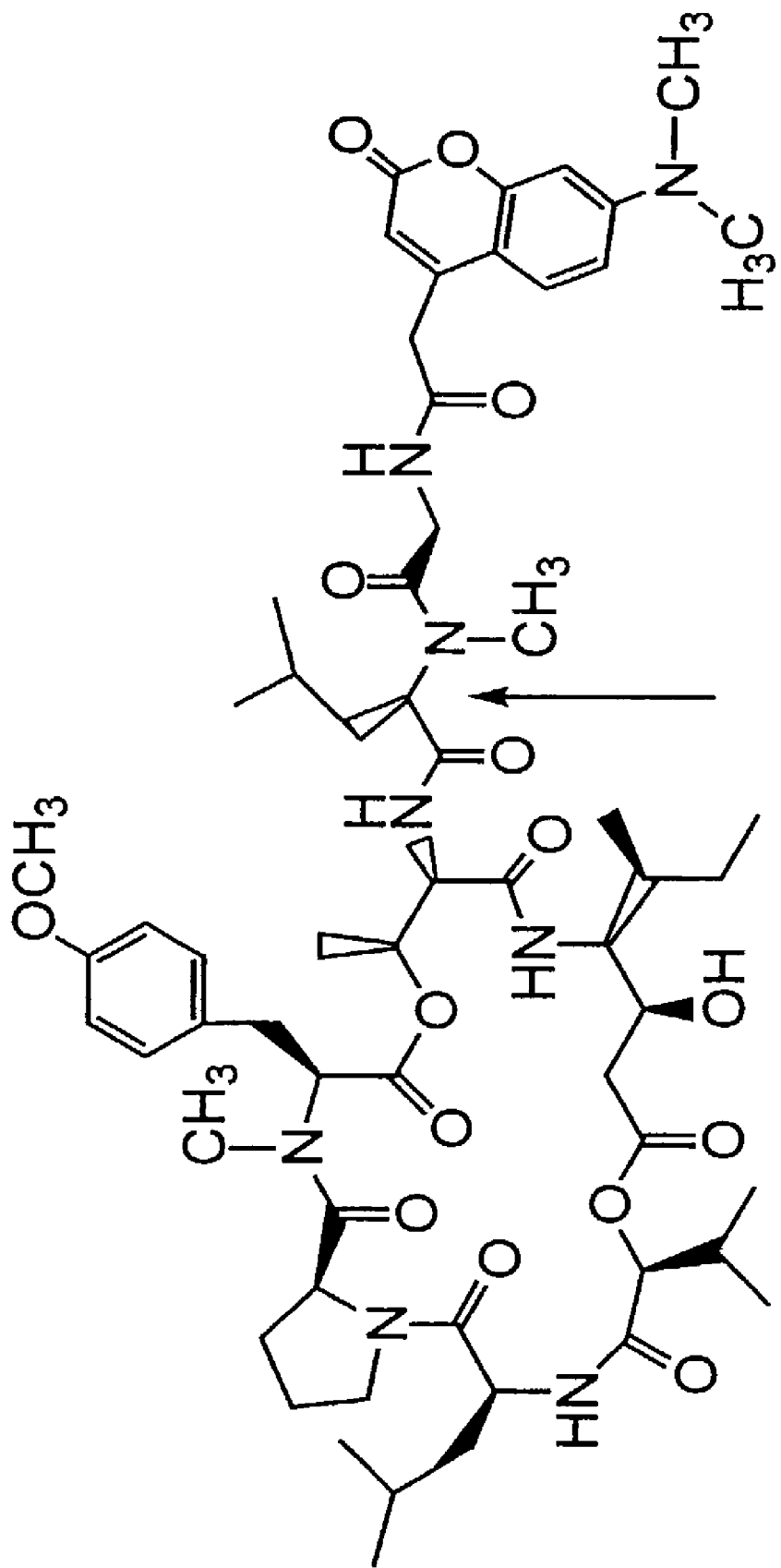
Fig. 4B

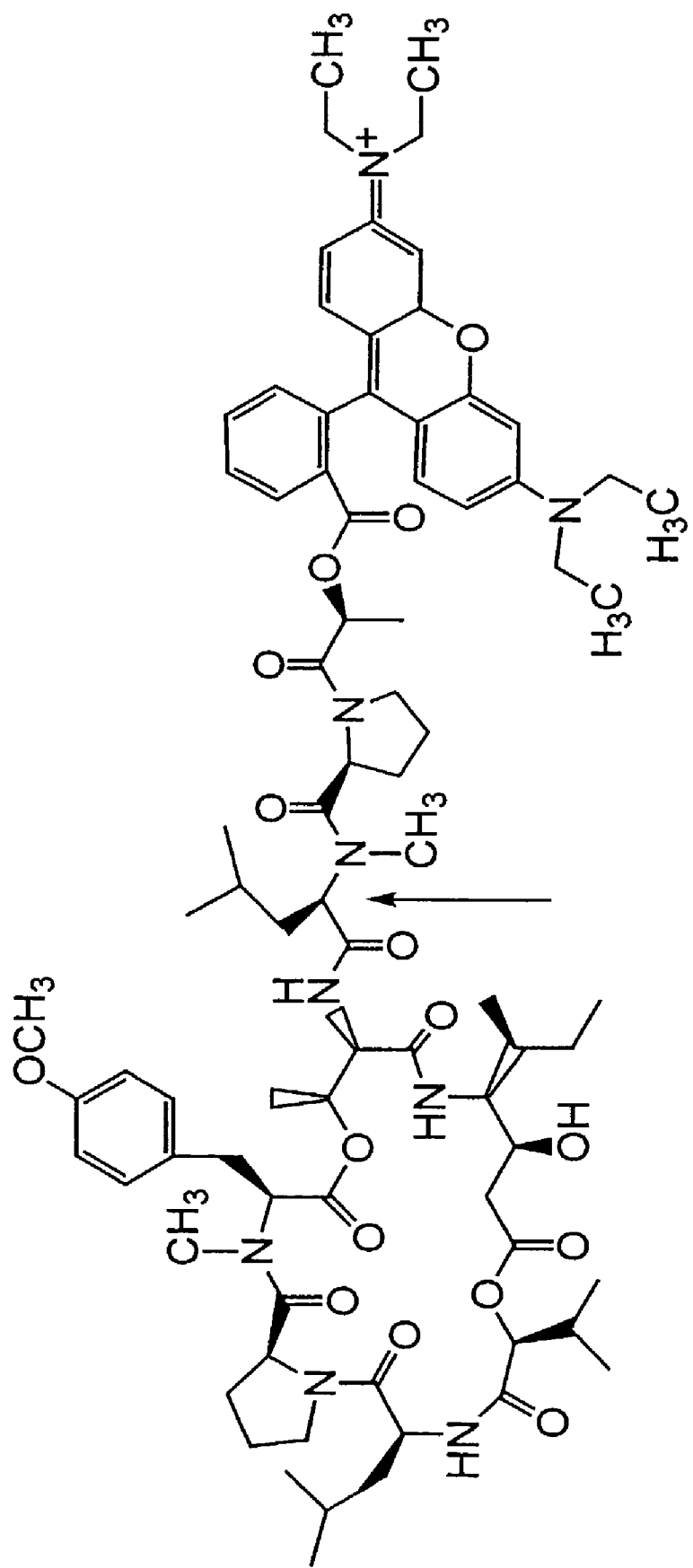
Fig. 4C

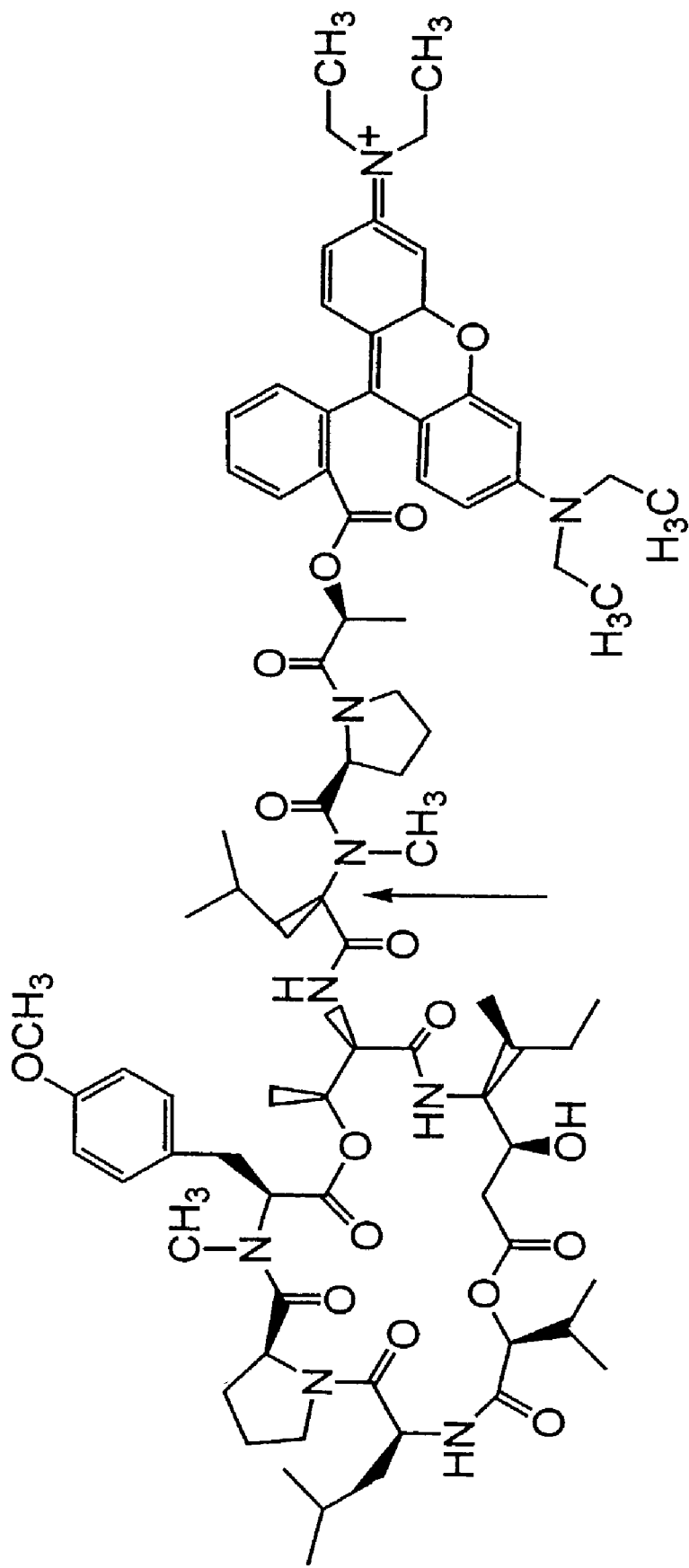
Fig. 4D

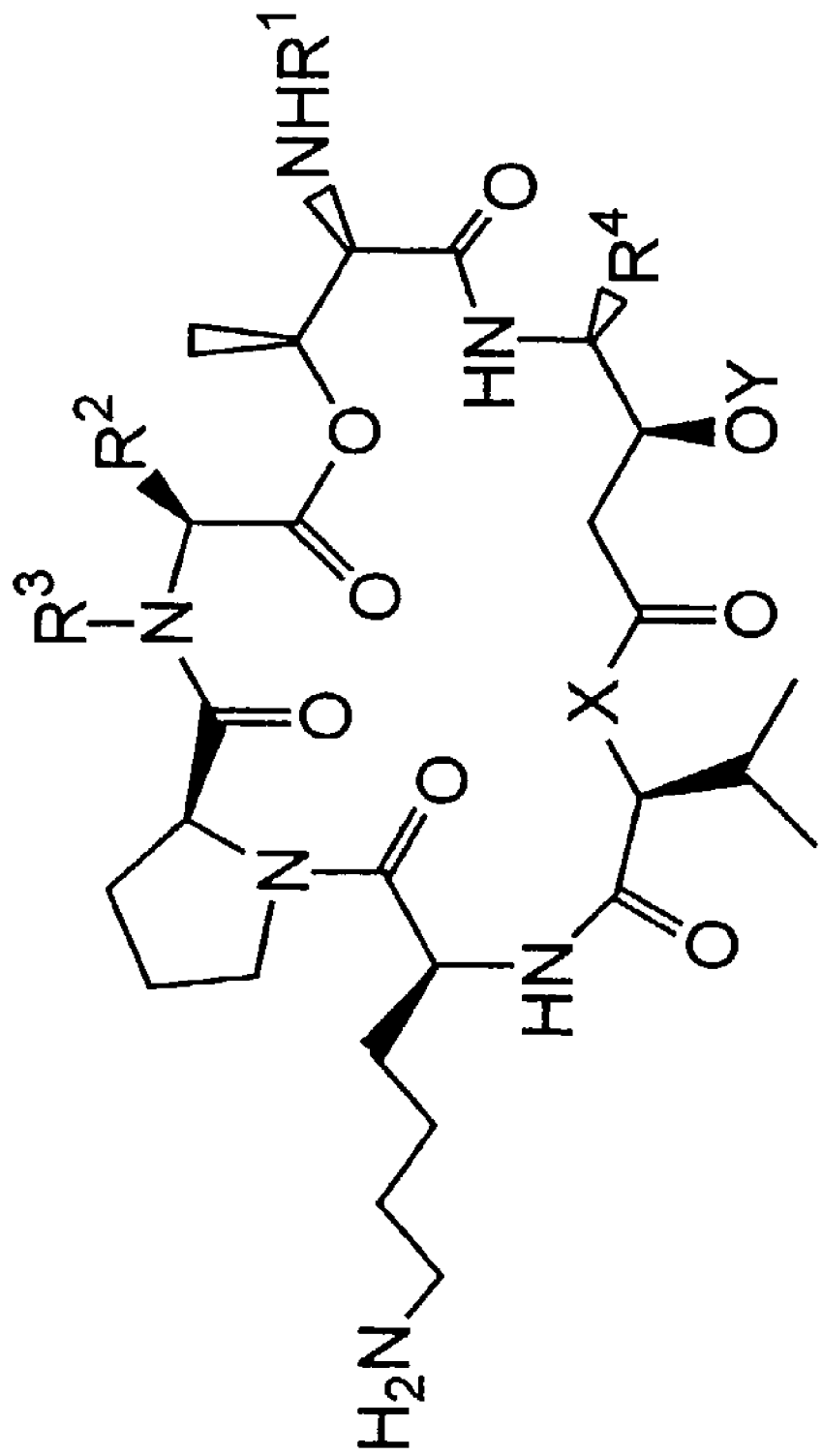
Fig. 5A

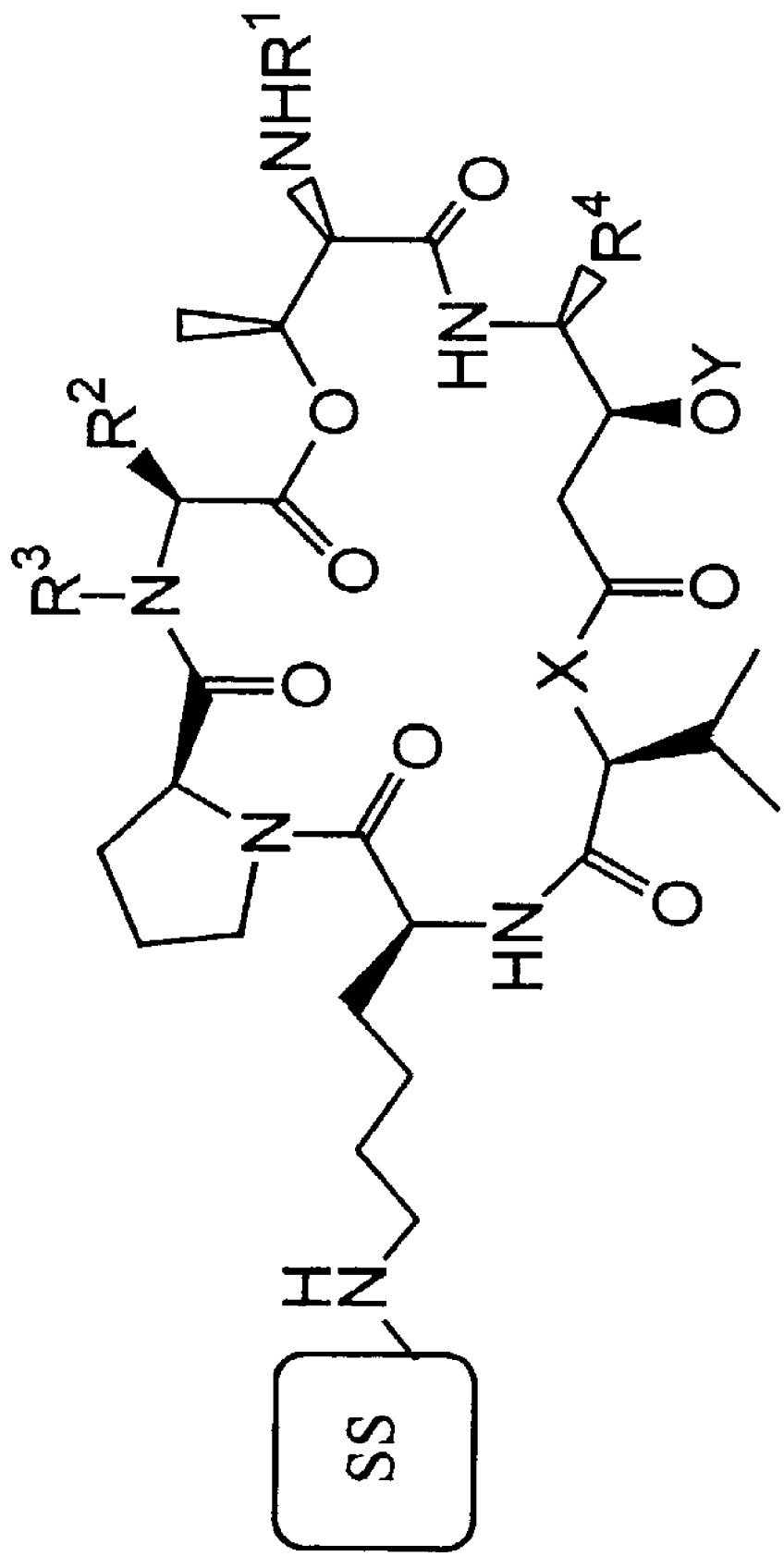
Fig. 5B

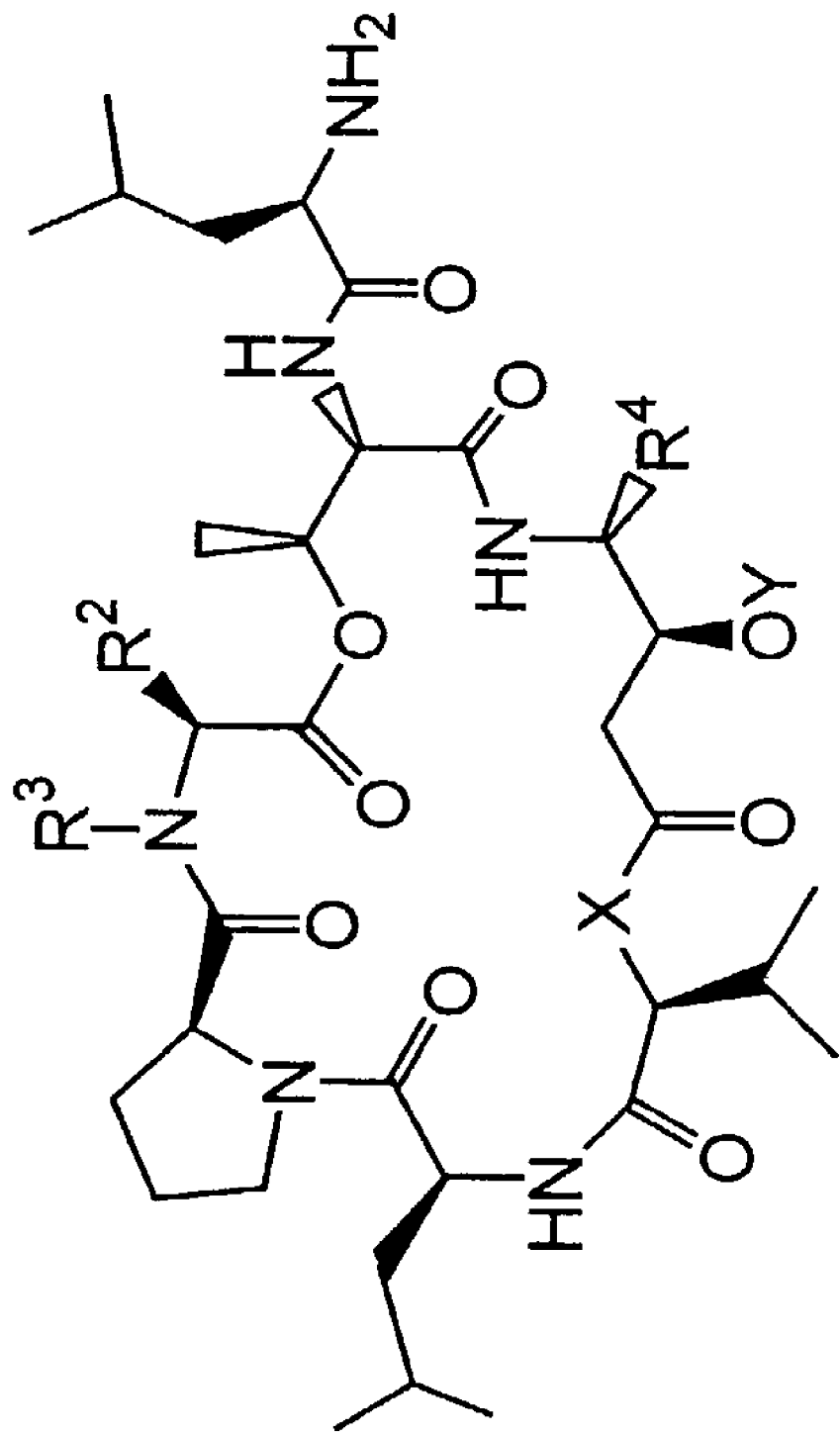
Fig. 6A

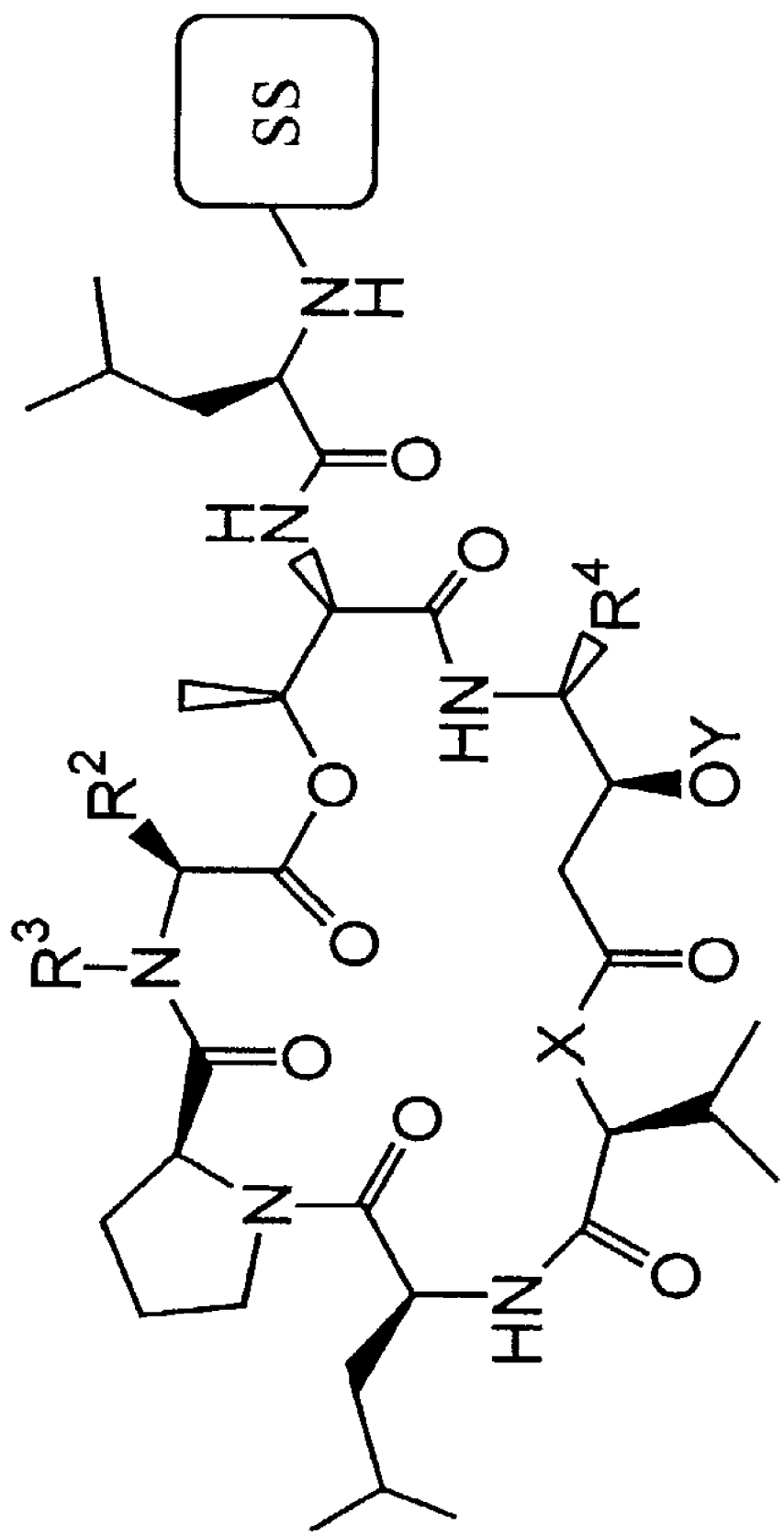
Fig. 6B

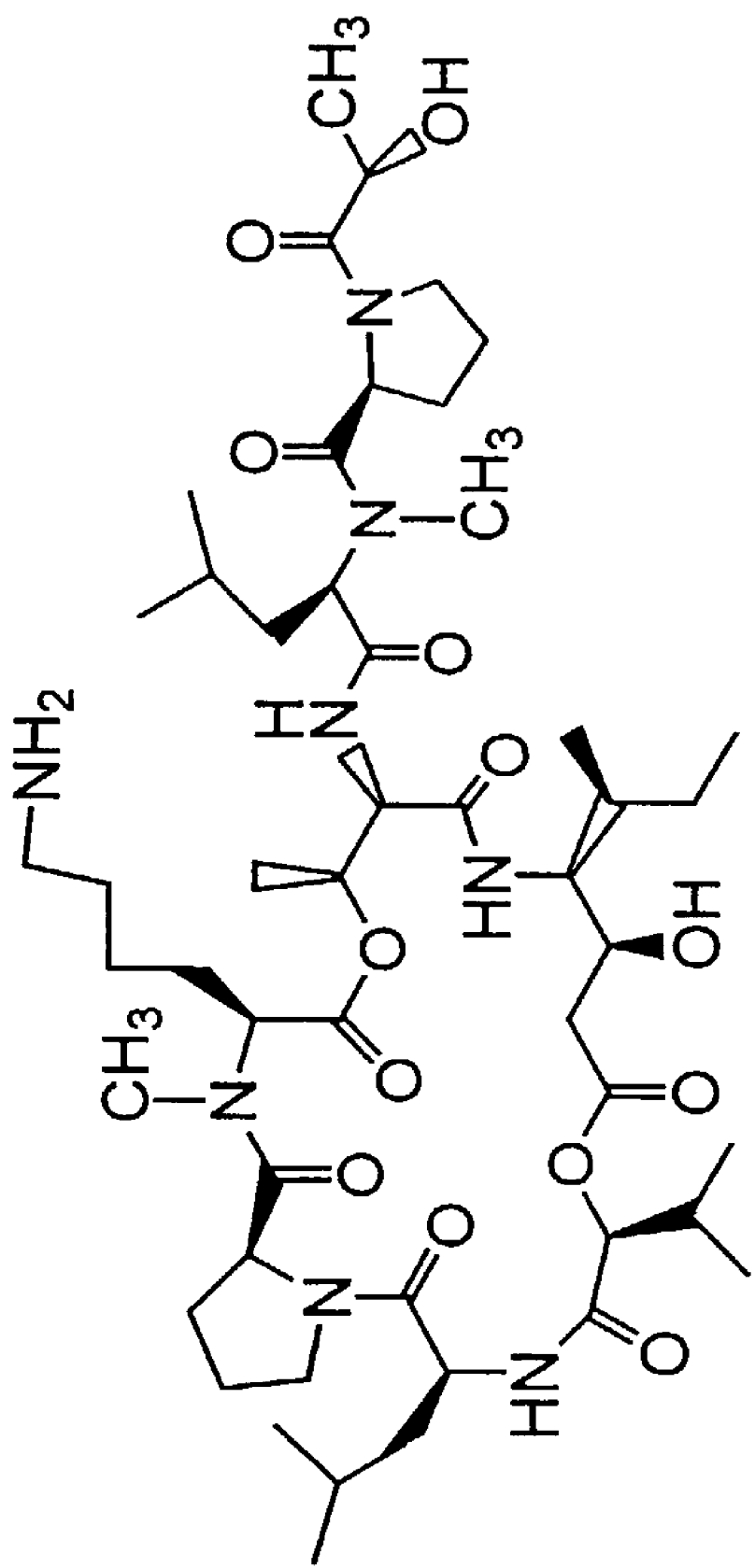
Fig. 7

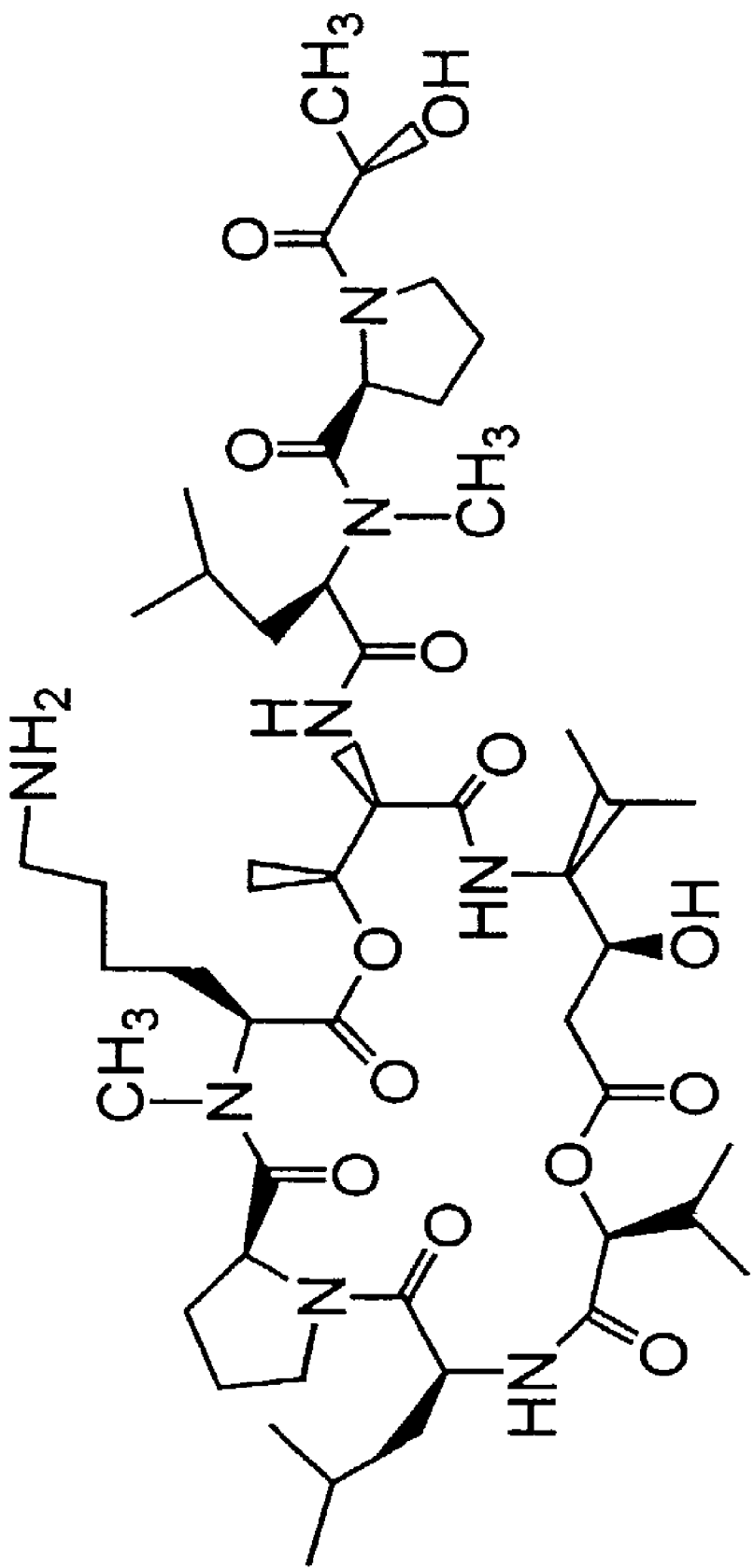
Fig. 8

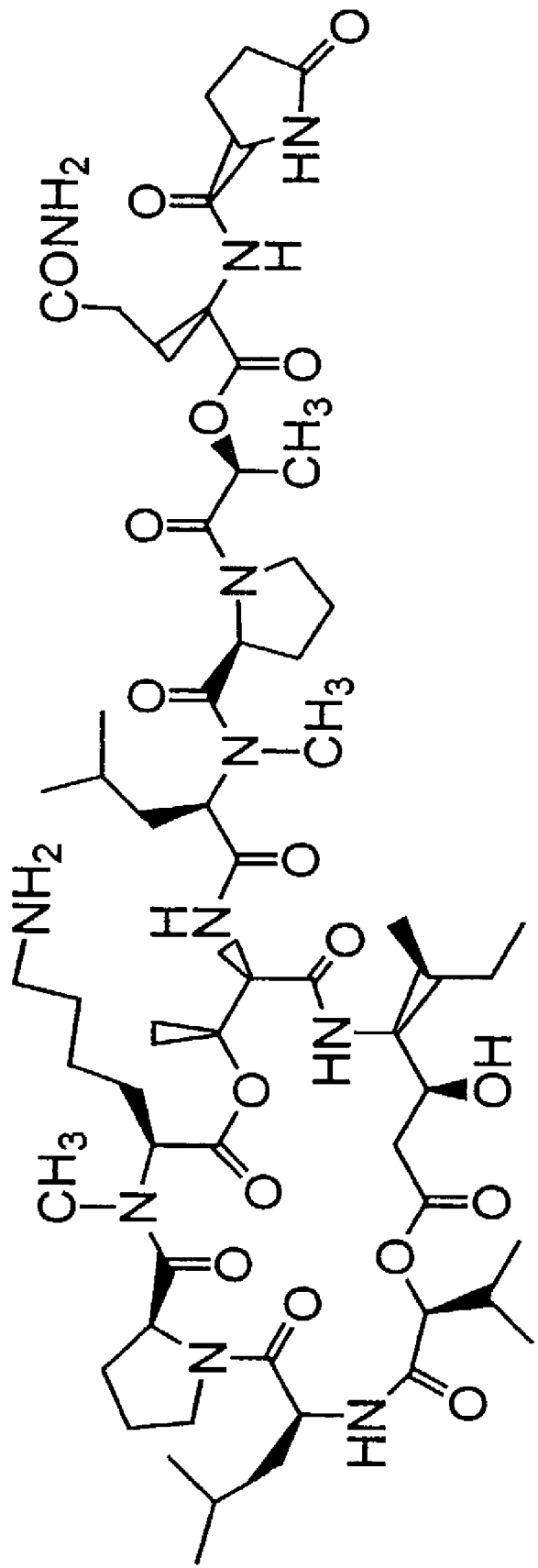
Fig. 9

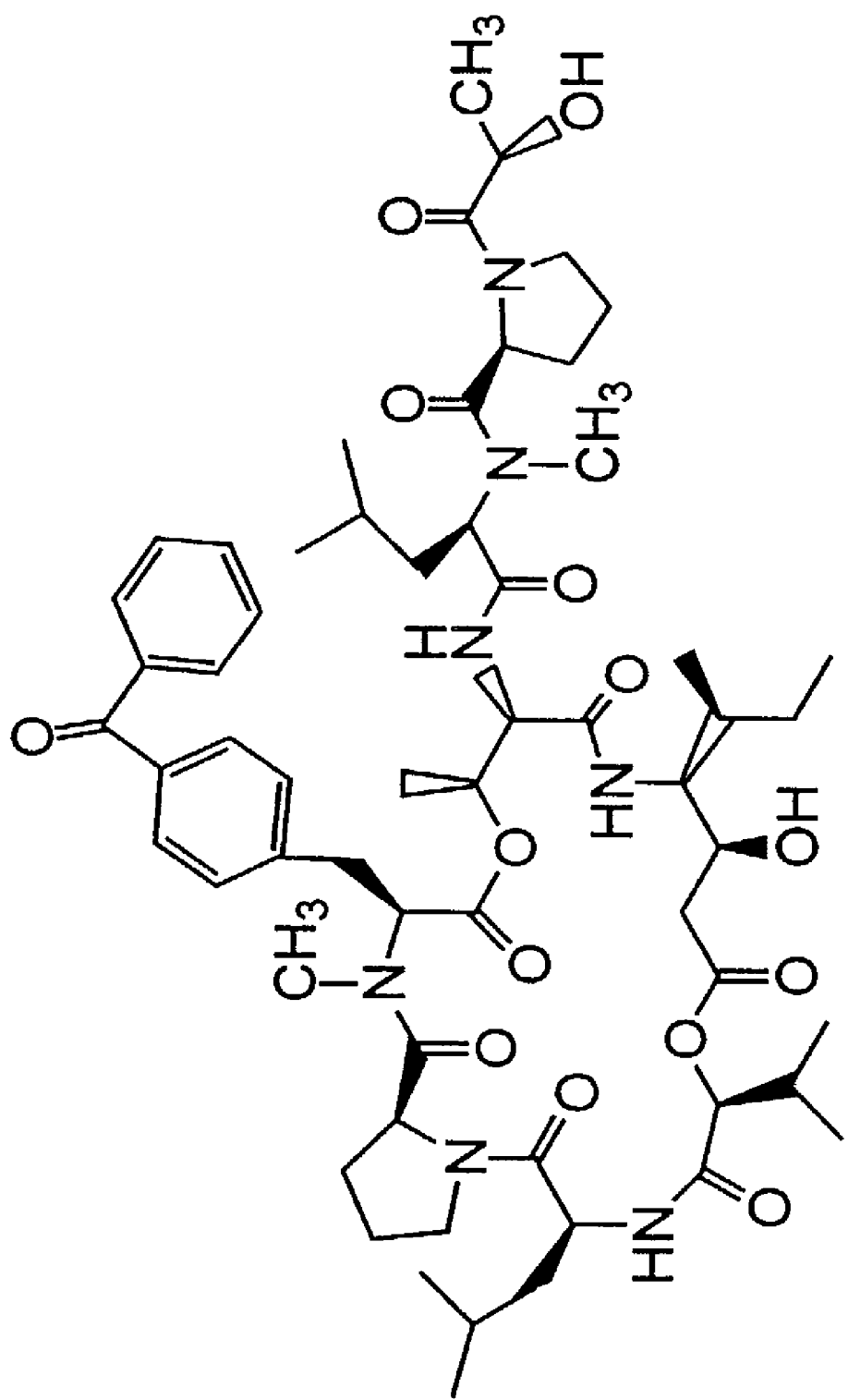
Fig. 10

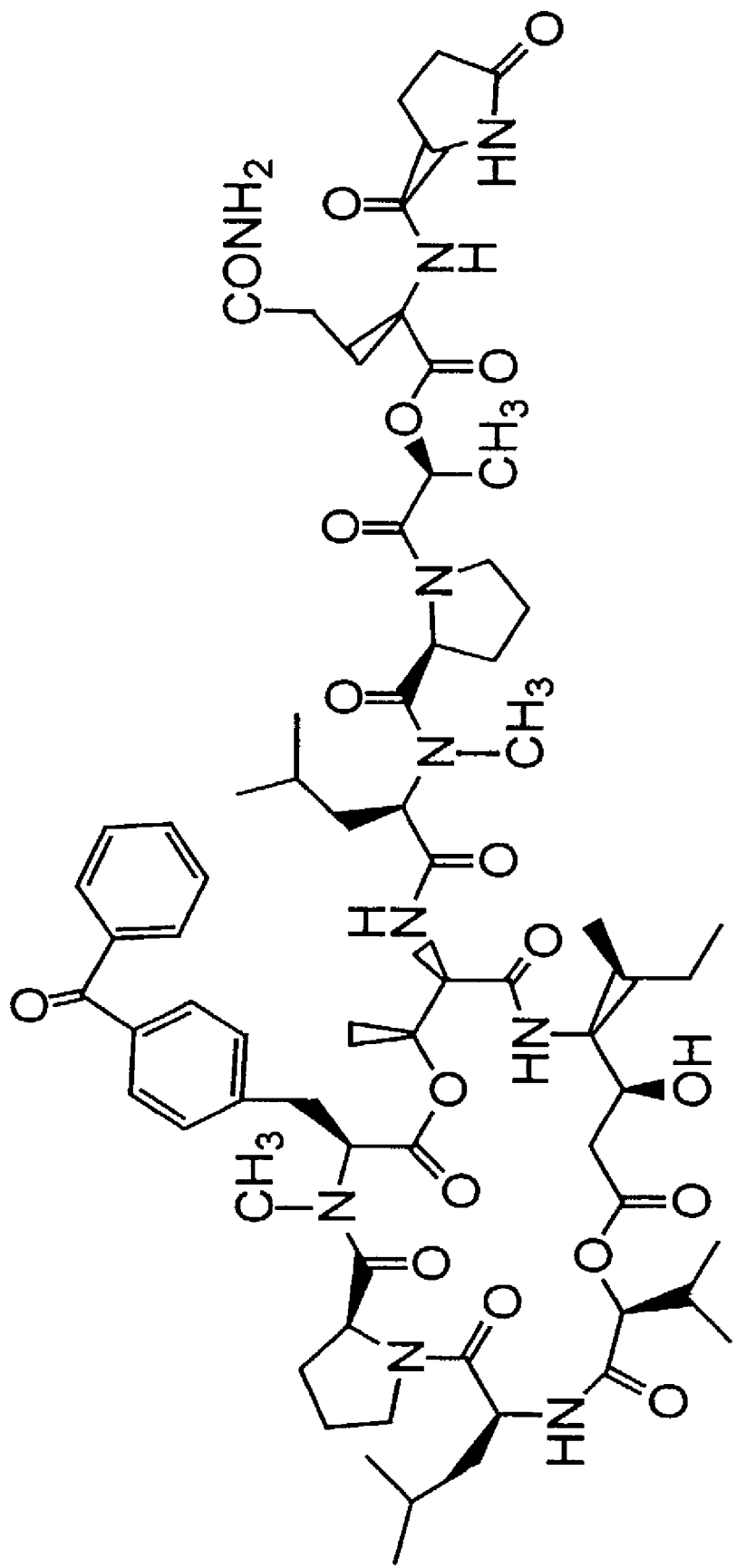
Fig. 11

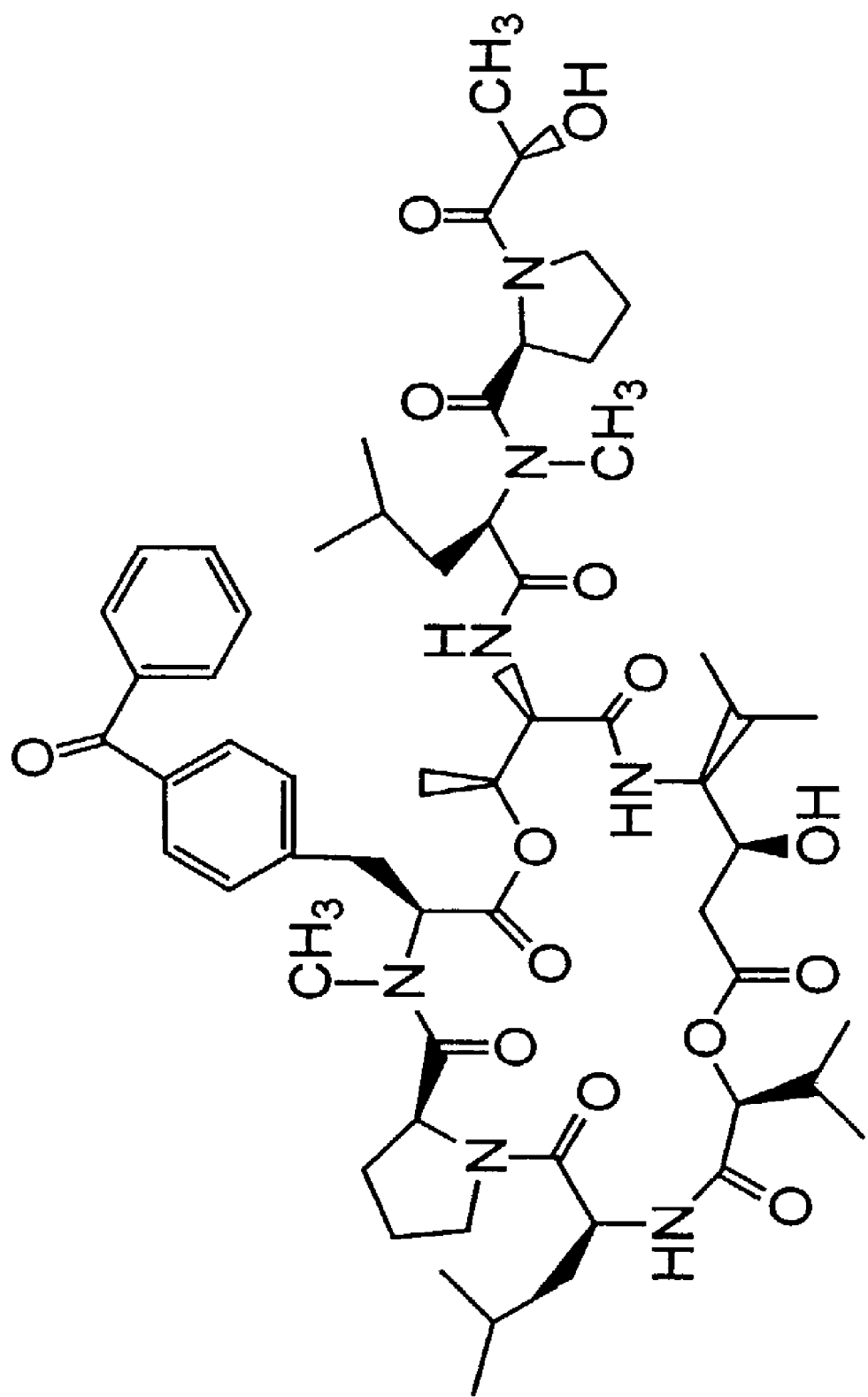
Fig. 12

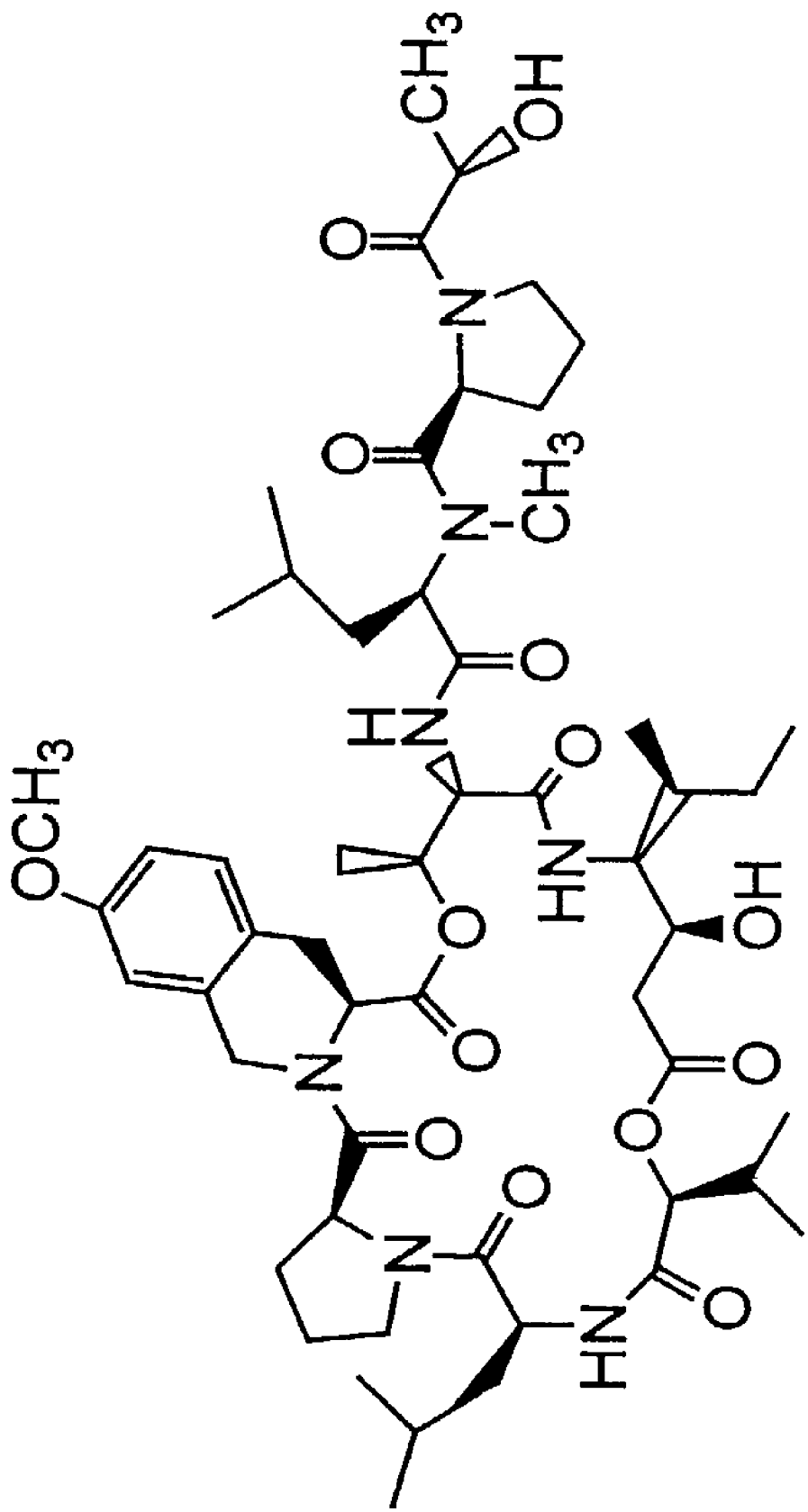
Fig. 13

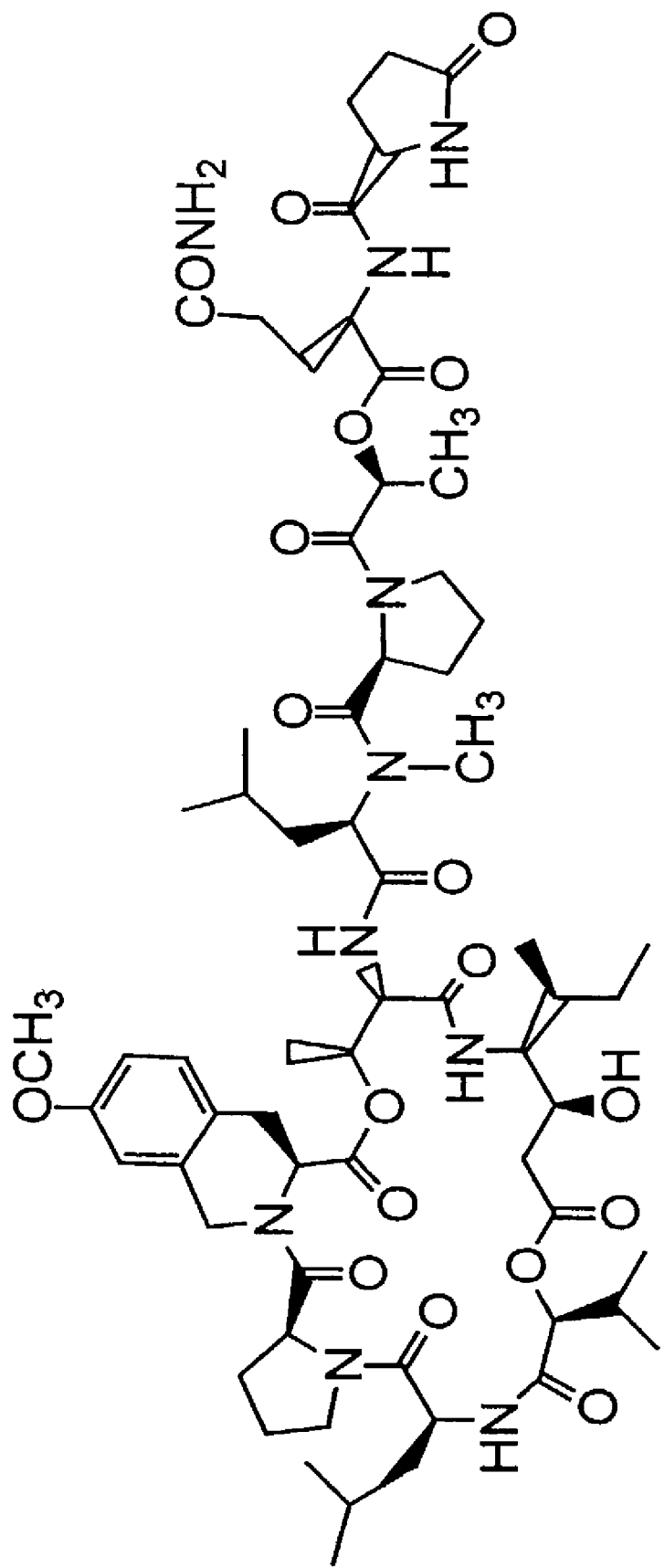
Fig. 14

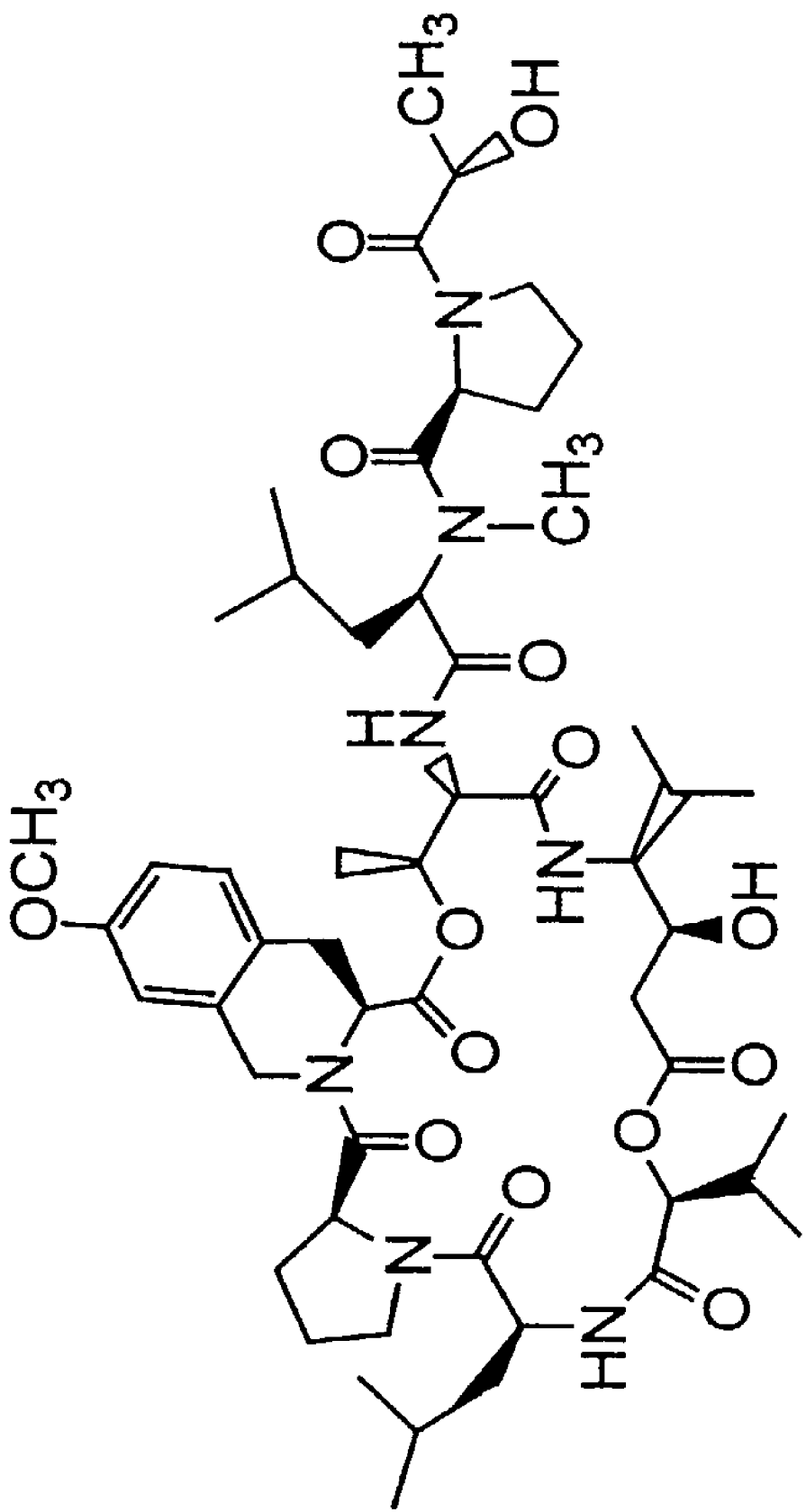
Fig. 15

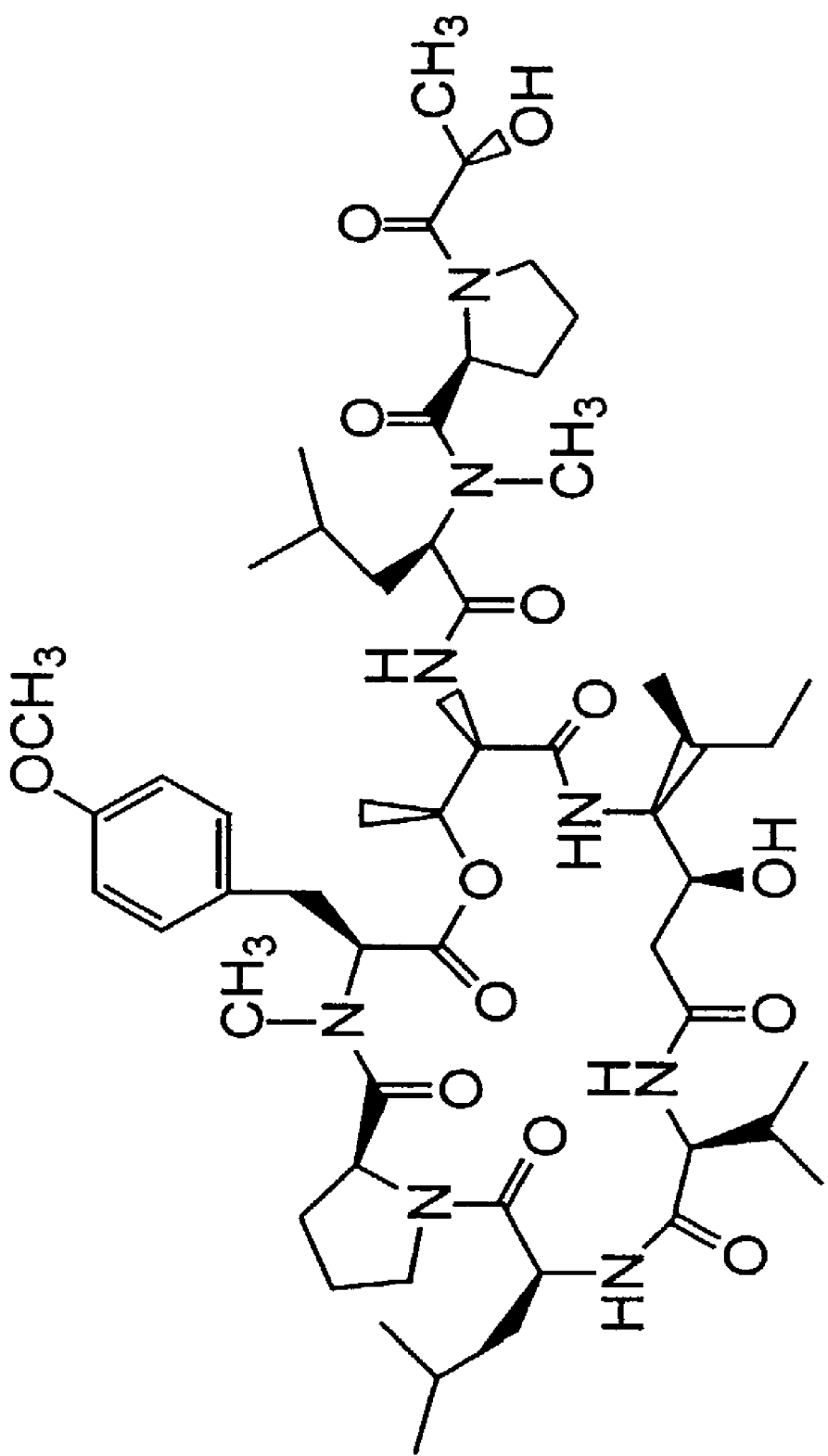
Fig. 16

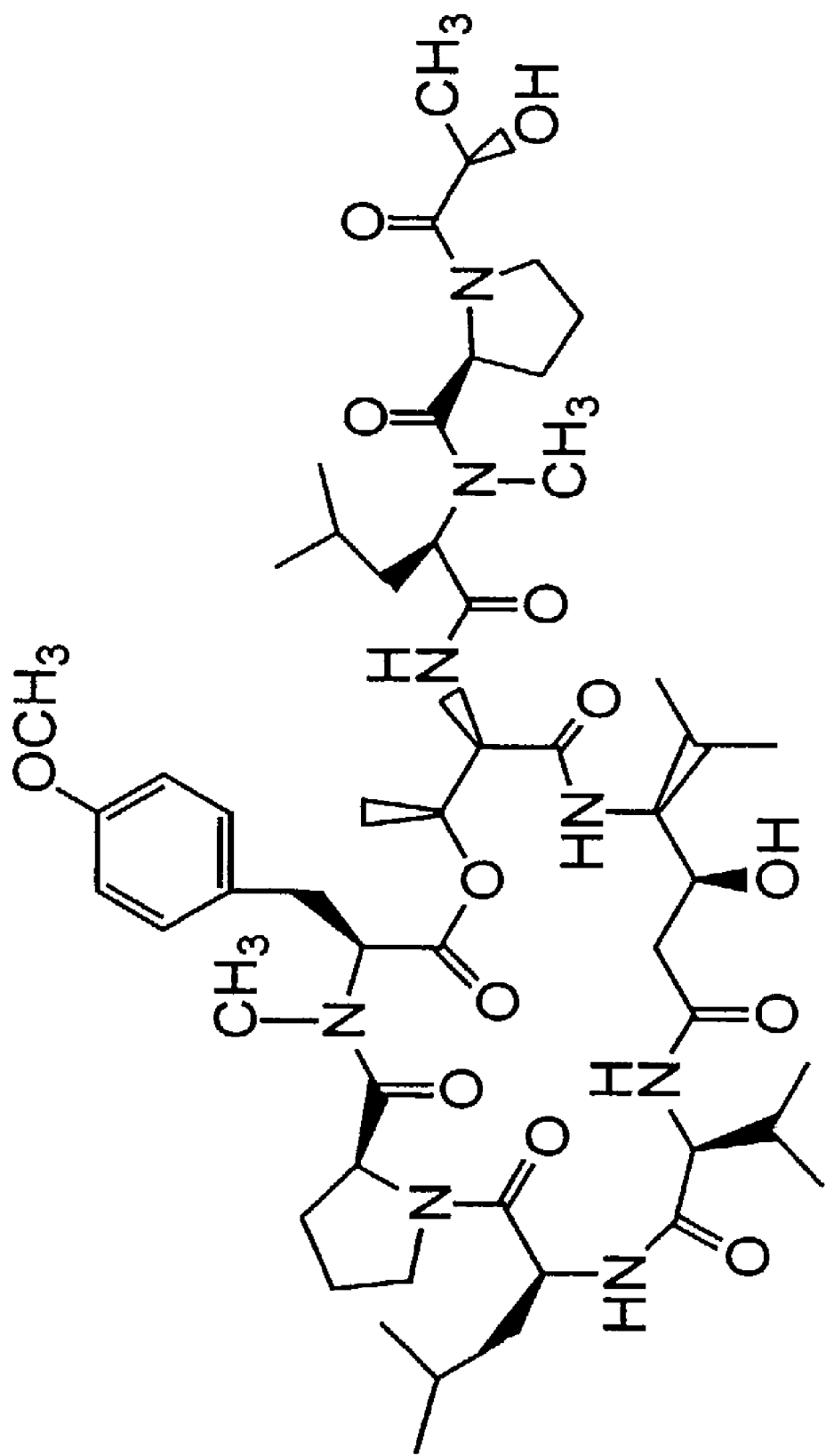
Fig. 17

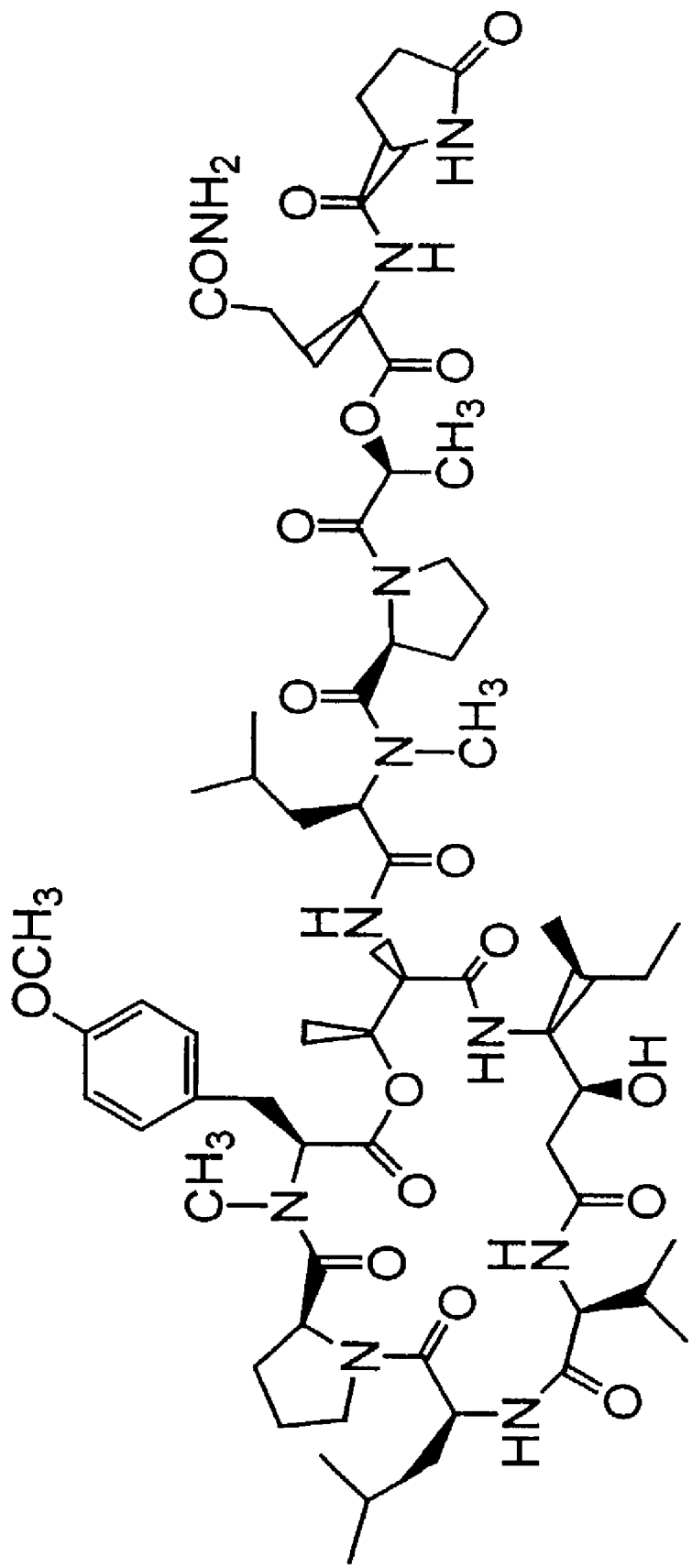
Fig. 18

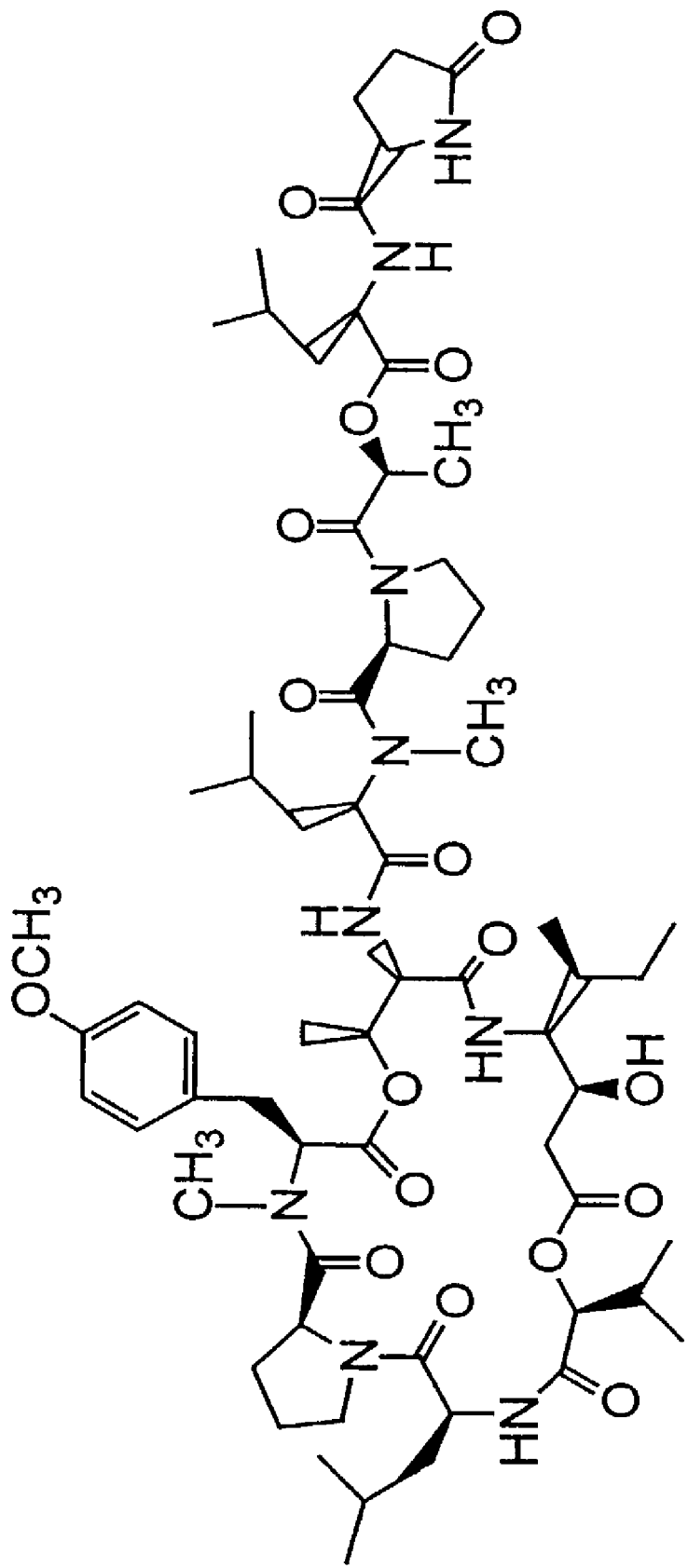
Fig. 19

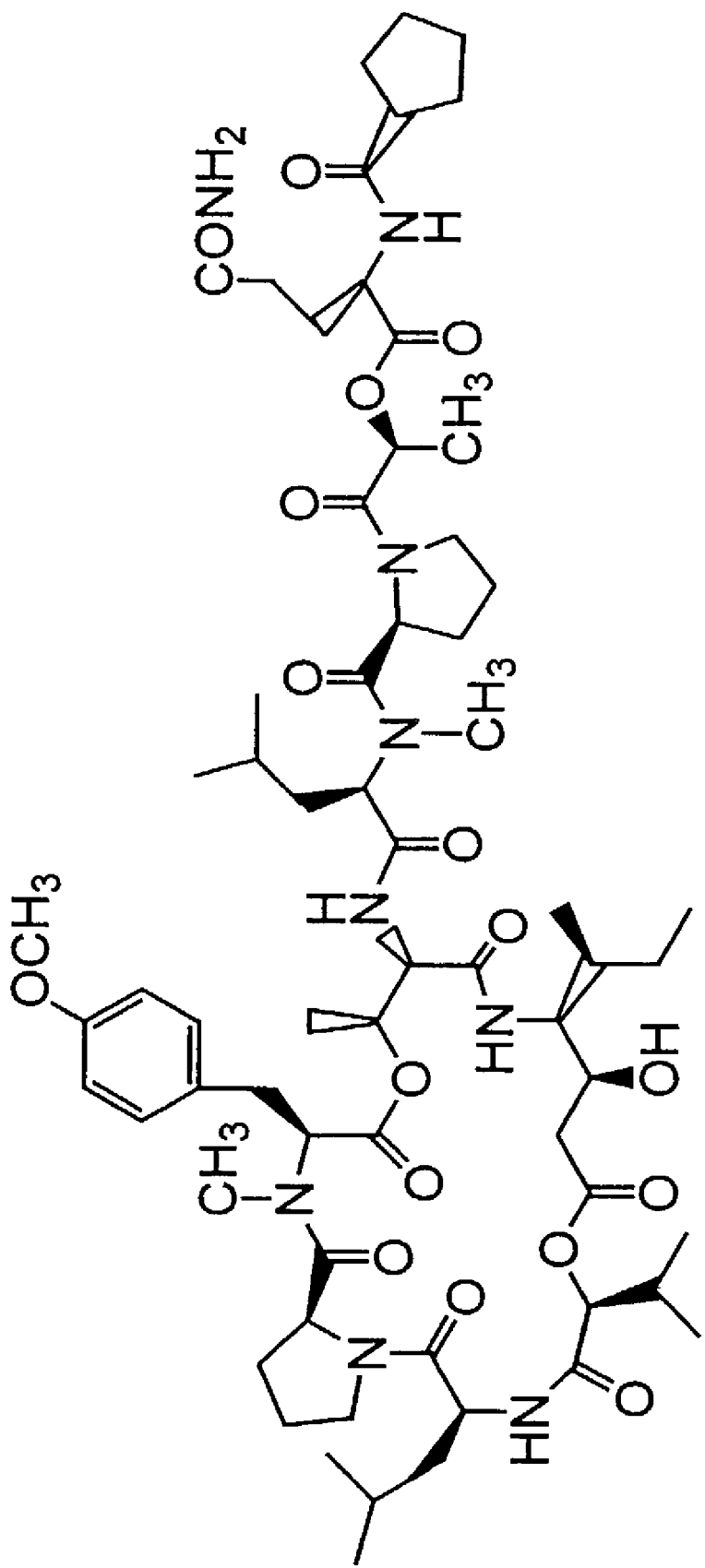
Fig. 20

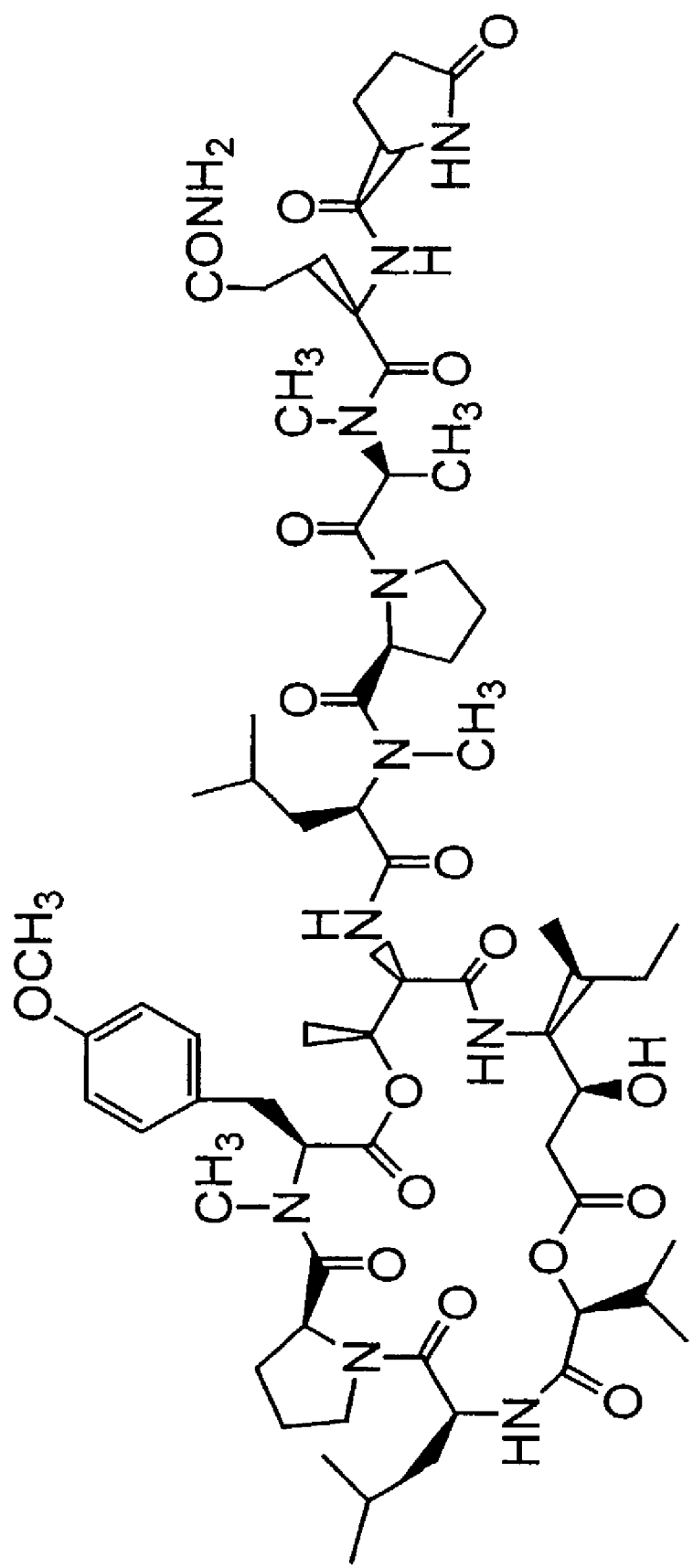
Fig. 21

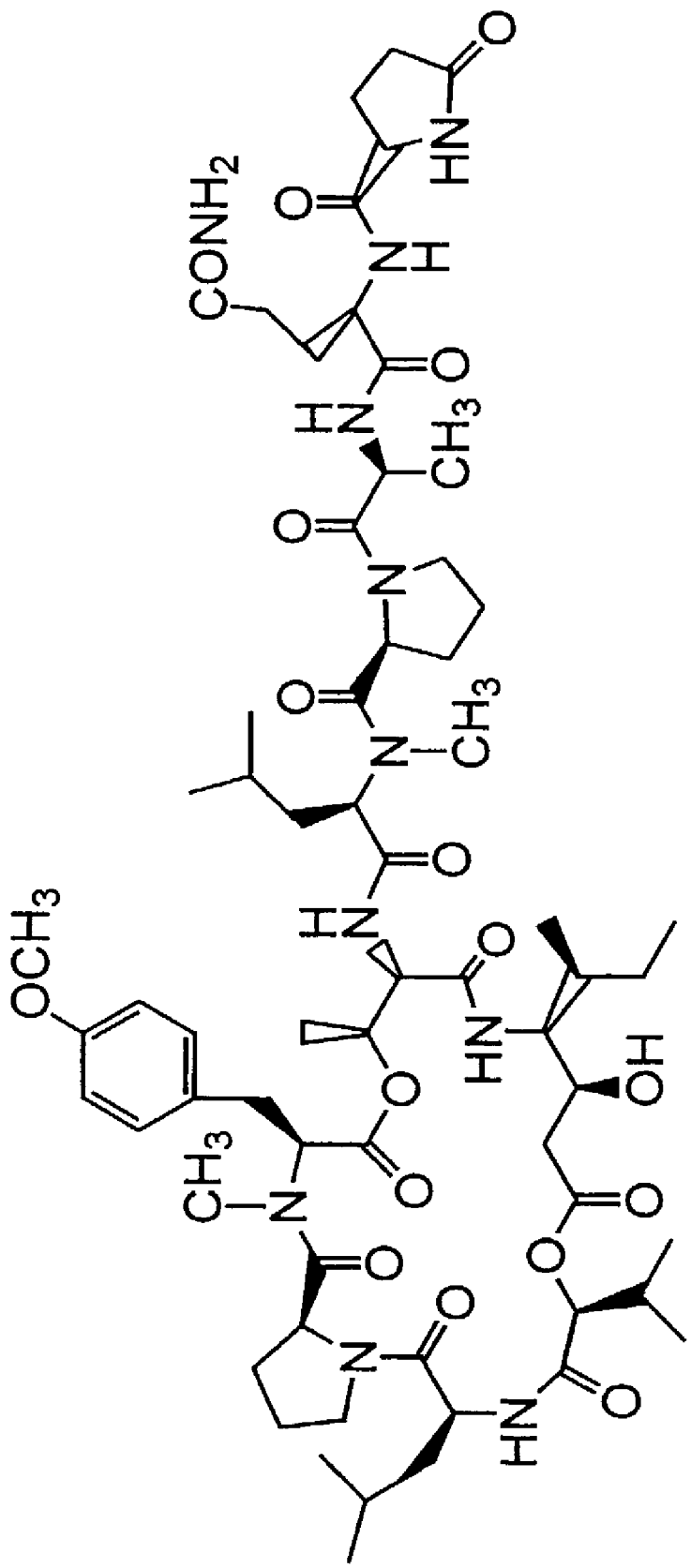
Fig. 22

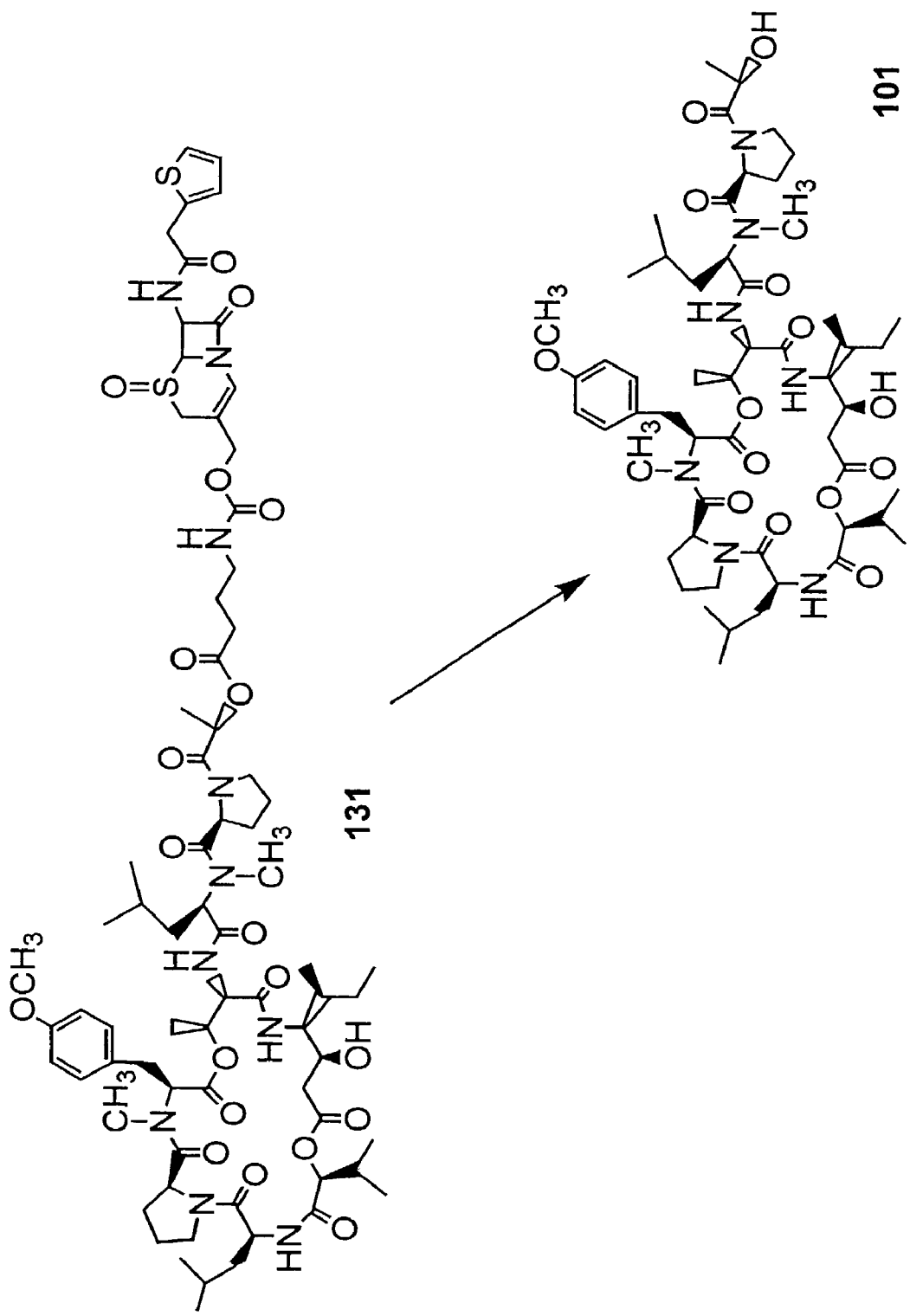
Fig. 23

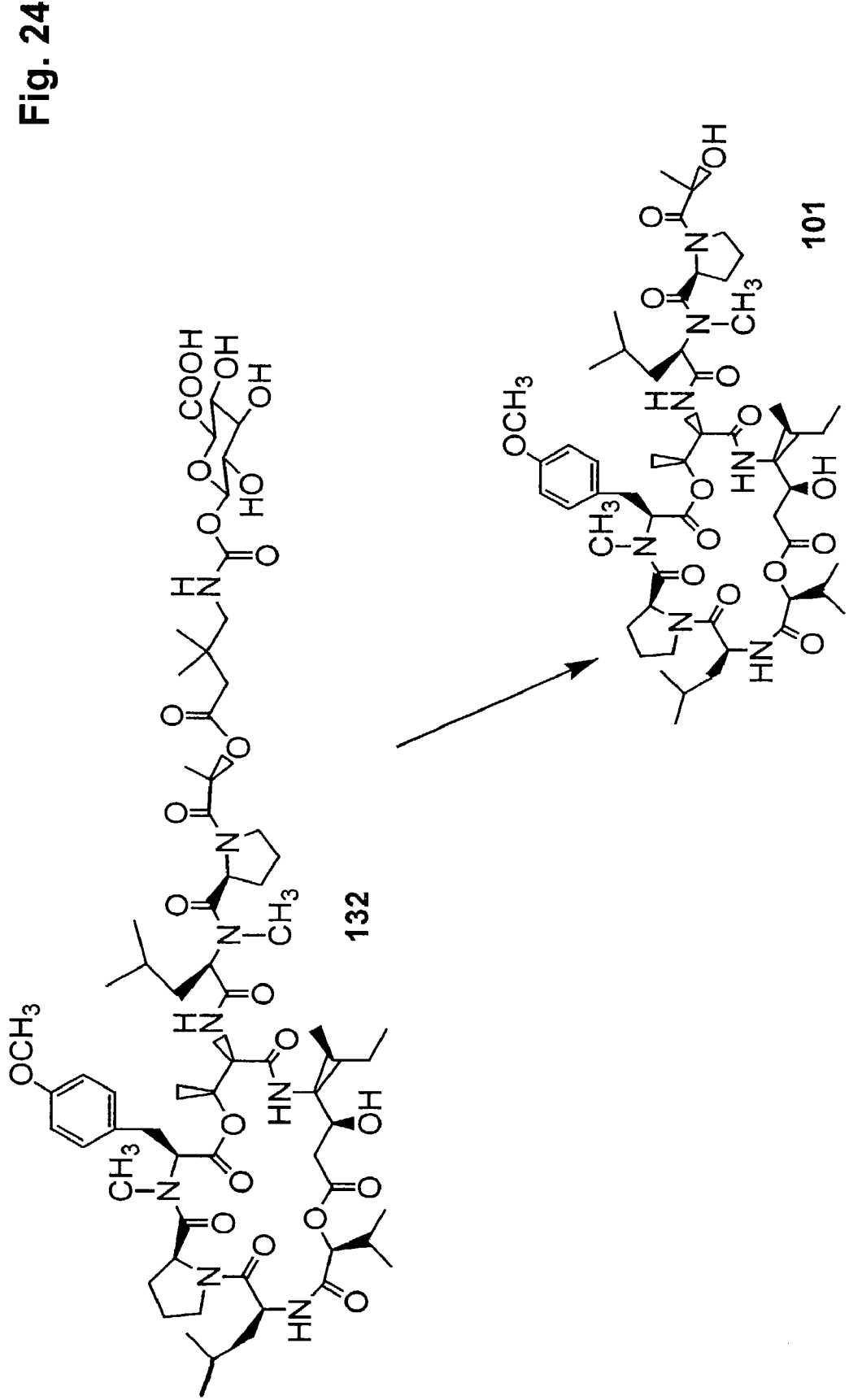
Fig. 24

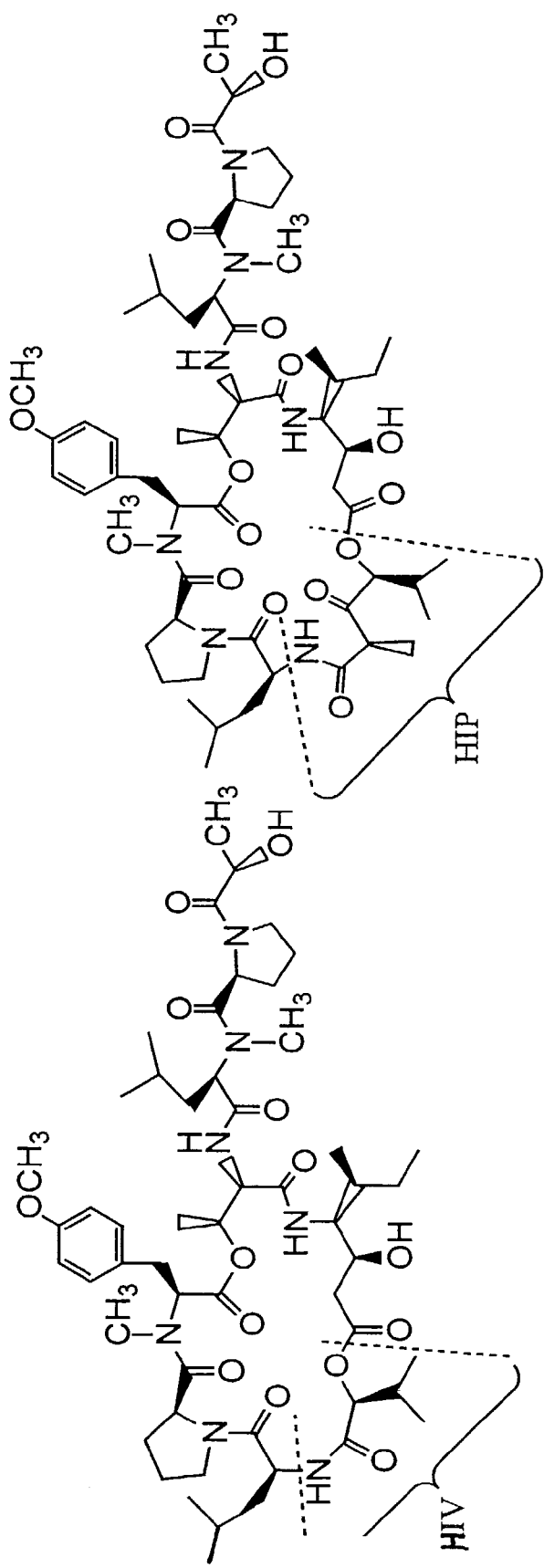
PRIOR ART
Fig. 25B
PRIOR ART
Fig. 25A

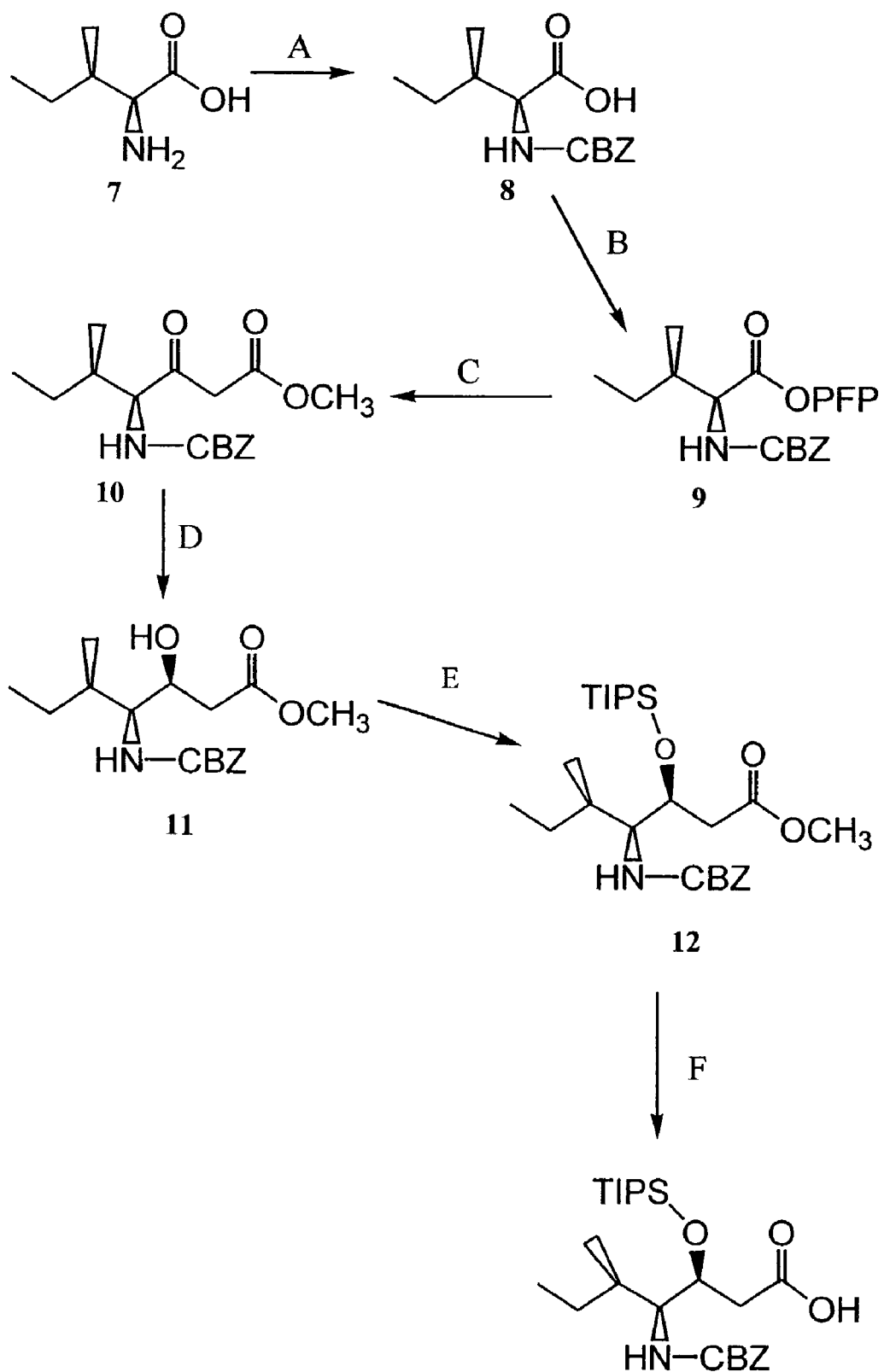
Fig. 26A

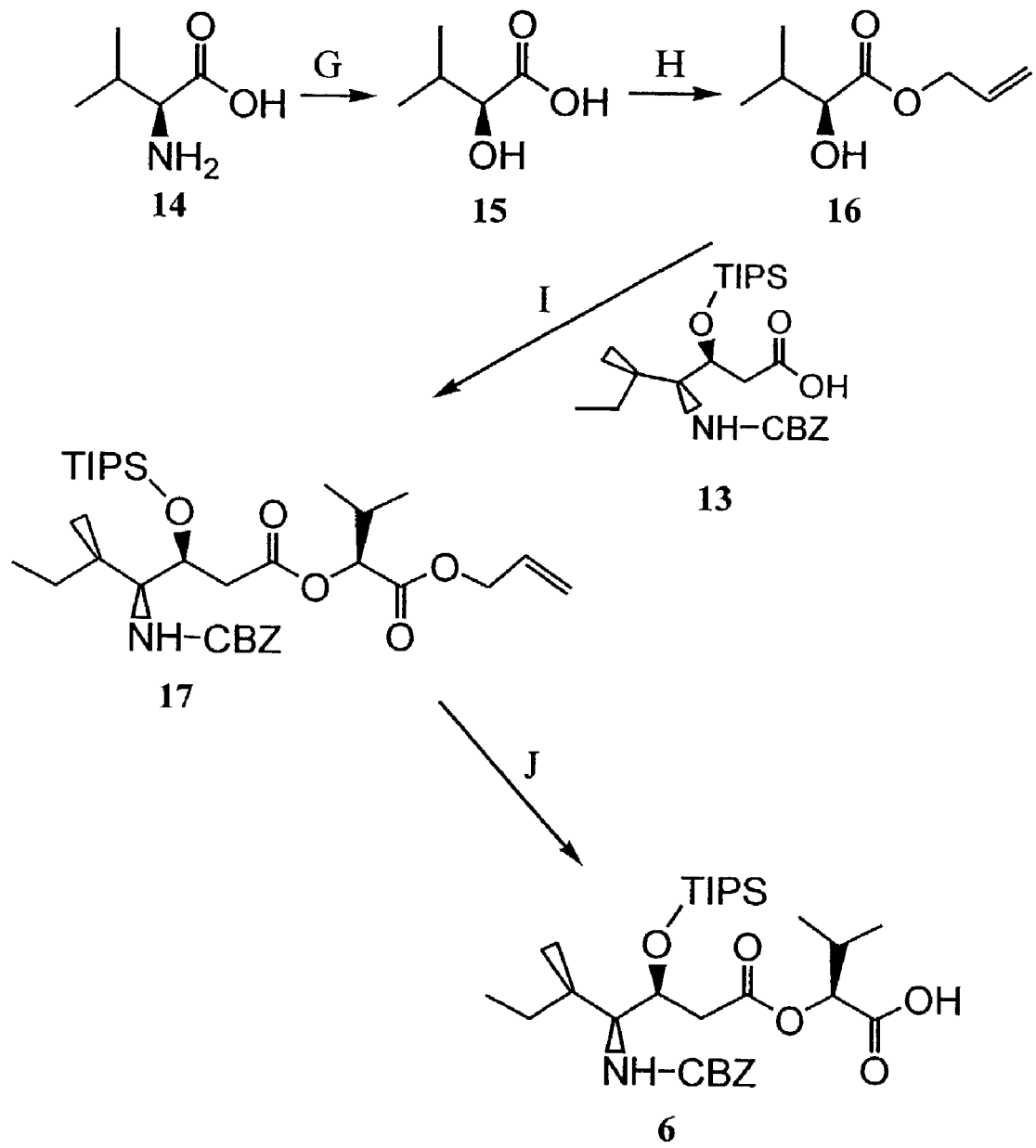
Fig. 26B

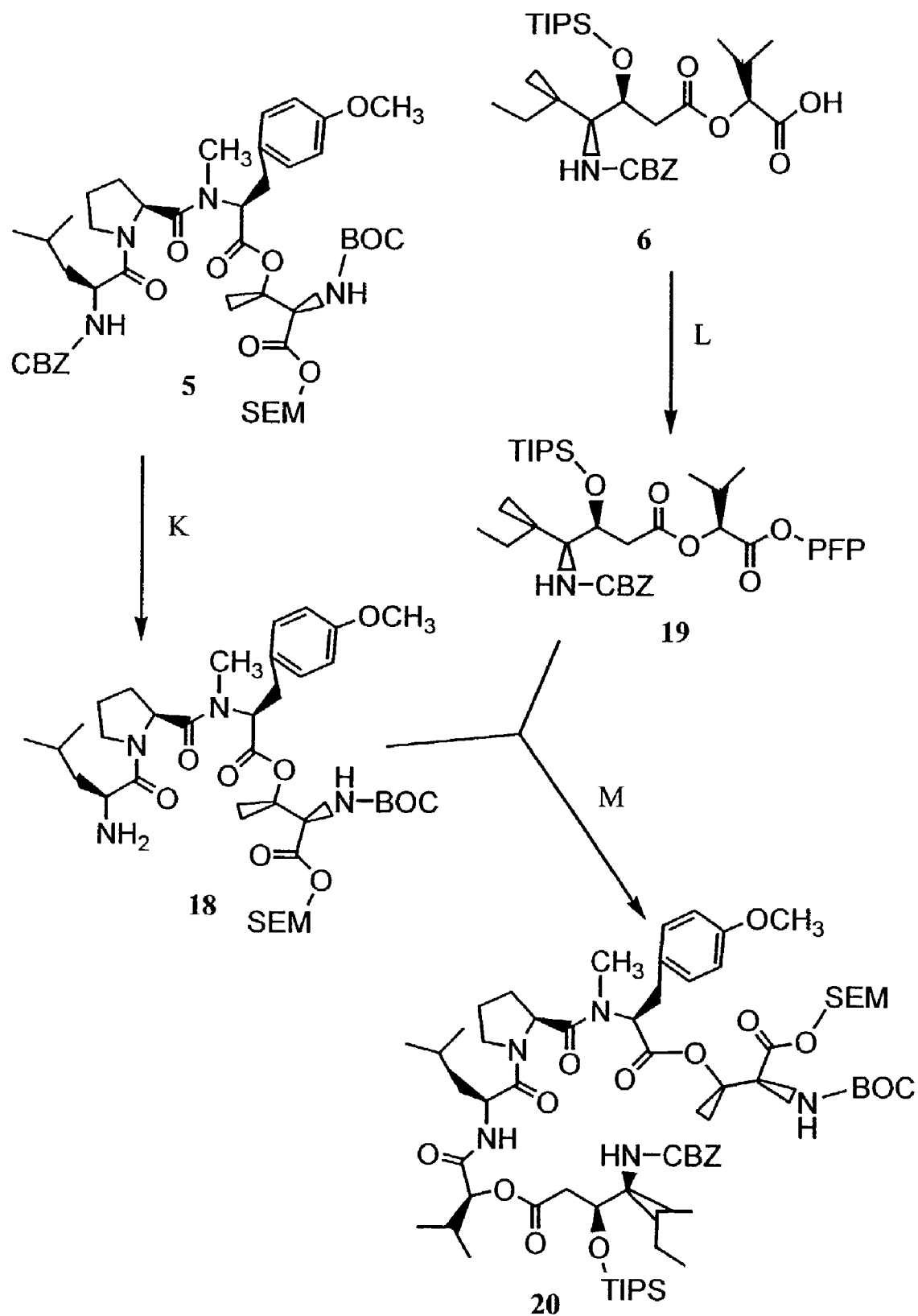
Fig. 26C

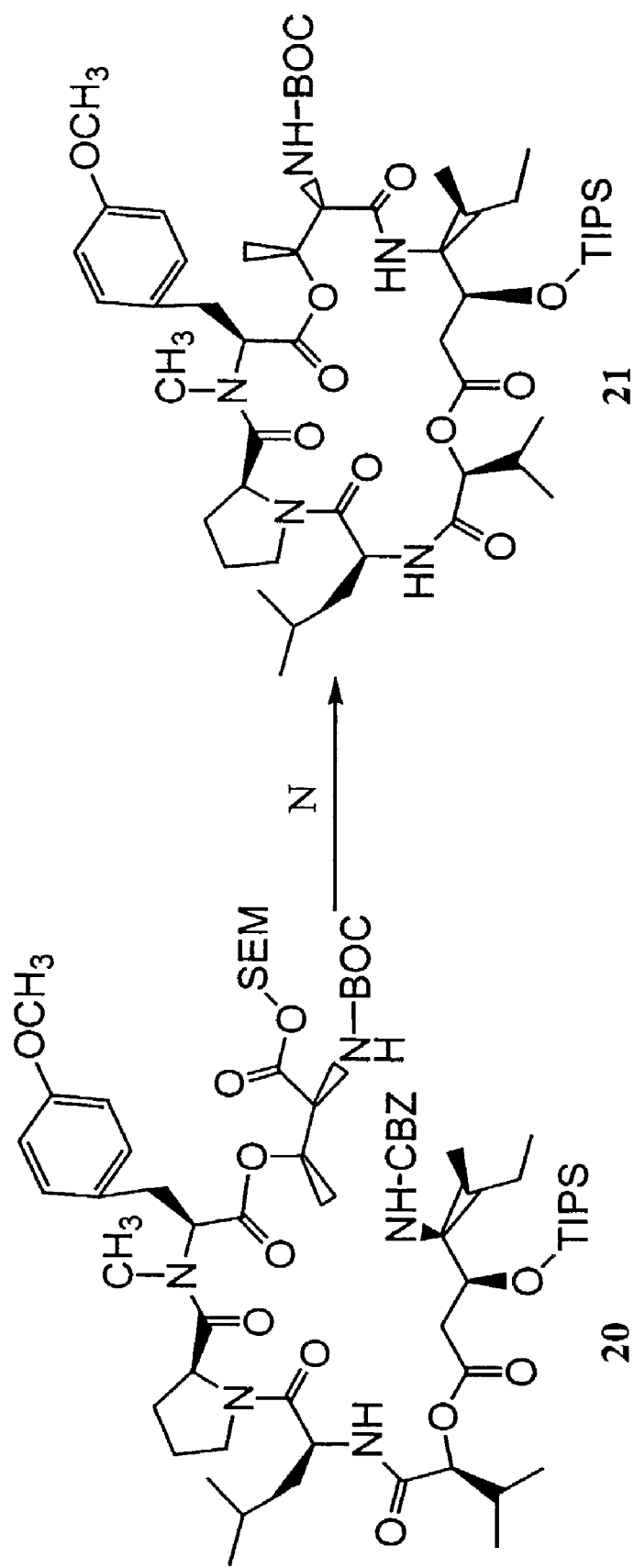
Fig. 26D

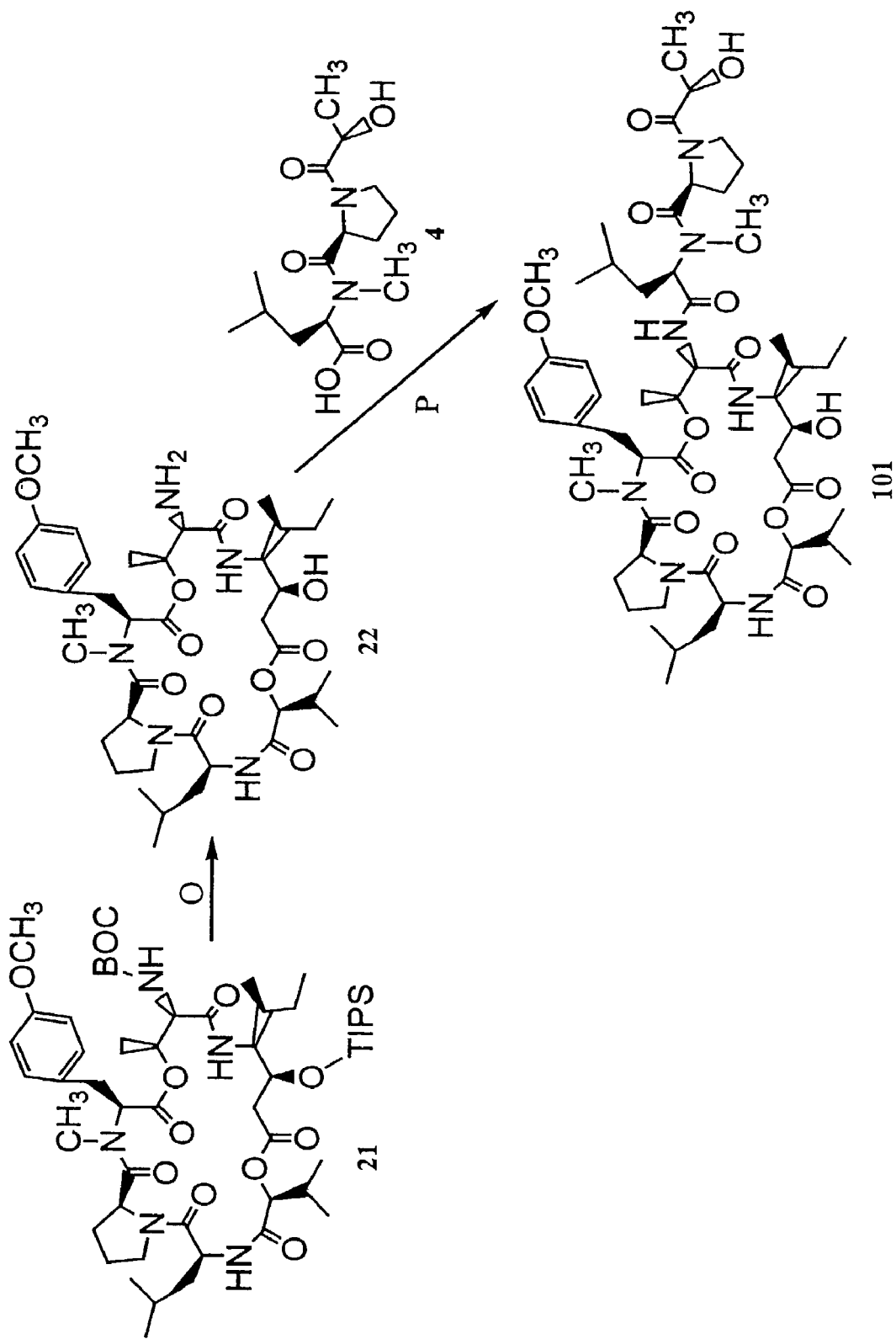
Fig. 26E

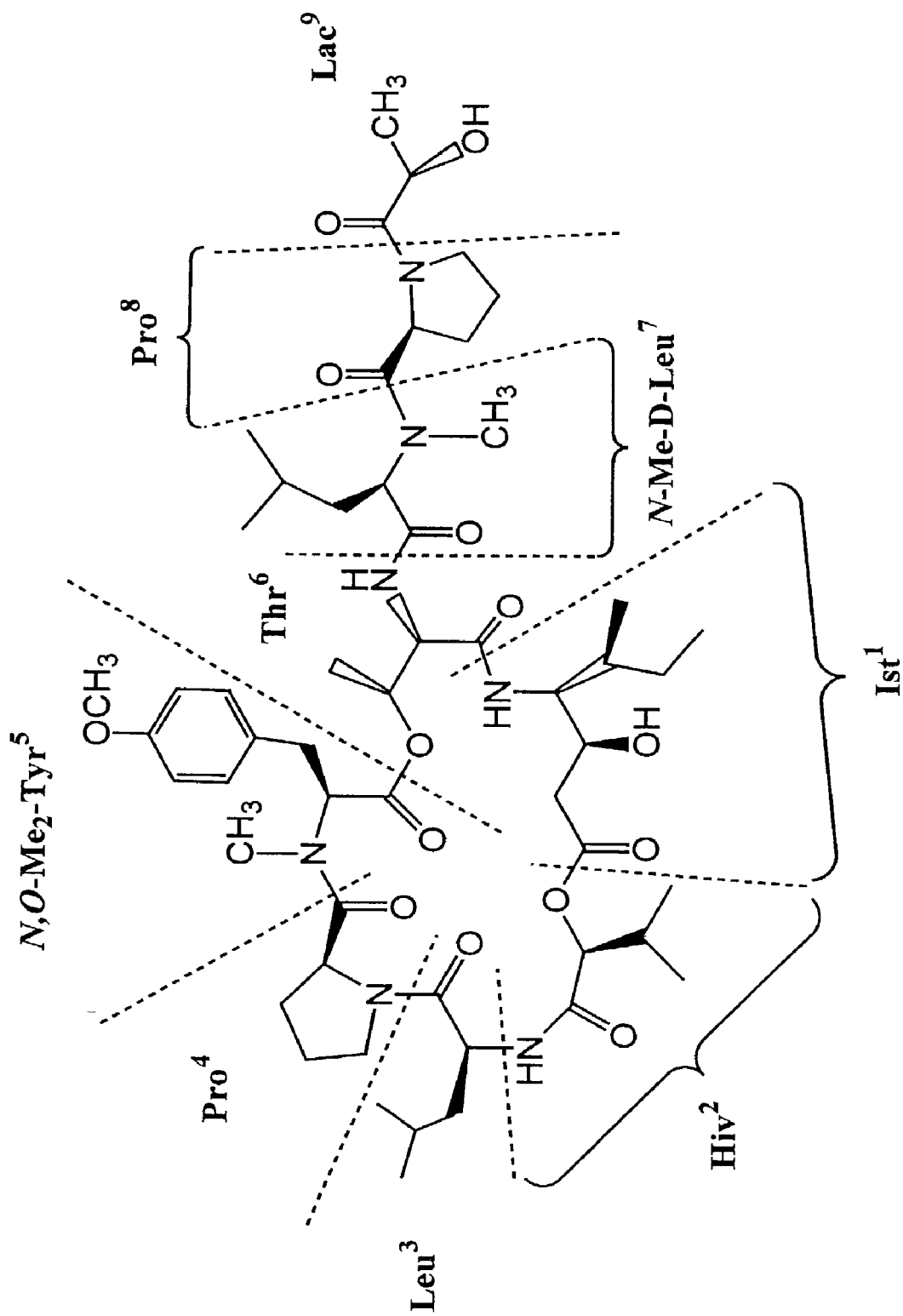
Fig. 27

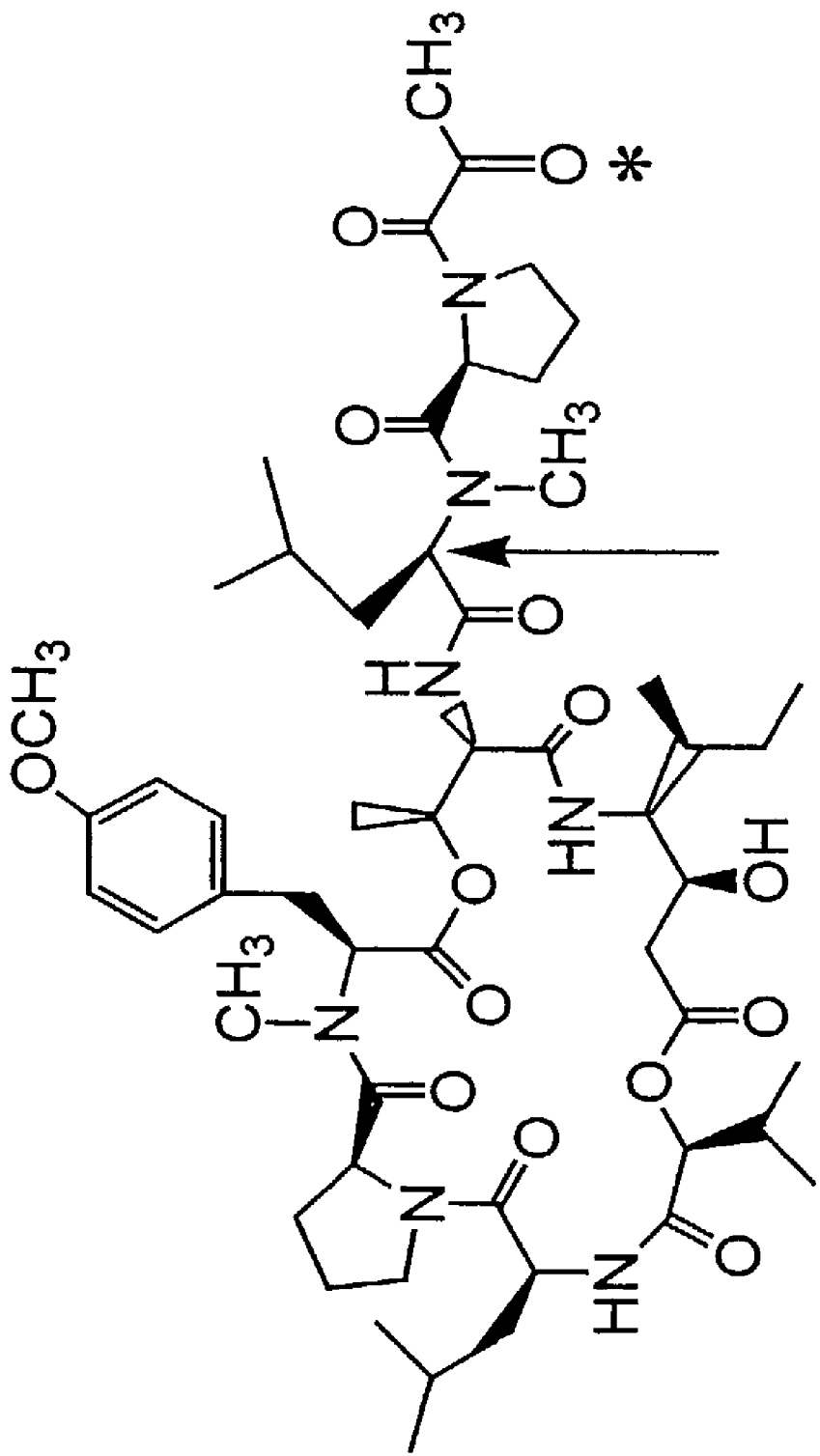
Fig. 28A

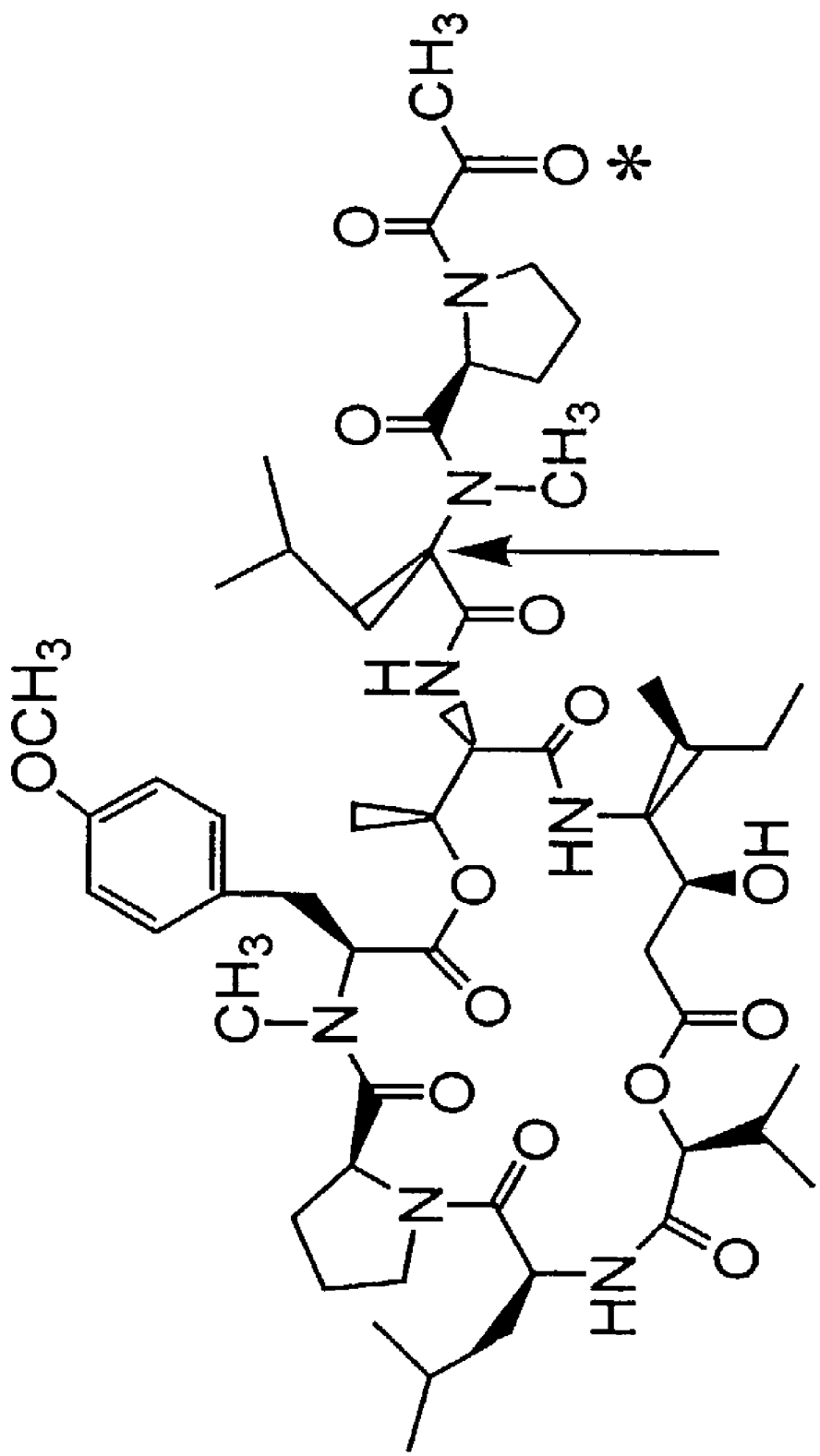
Fig. 28B

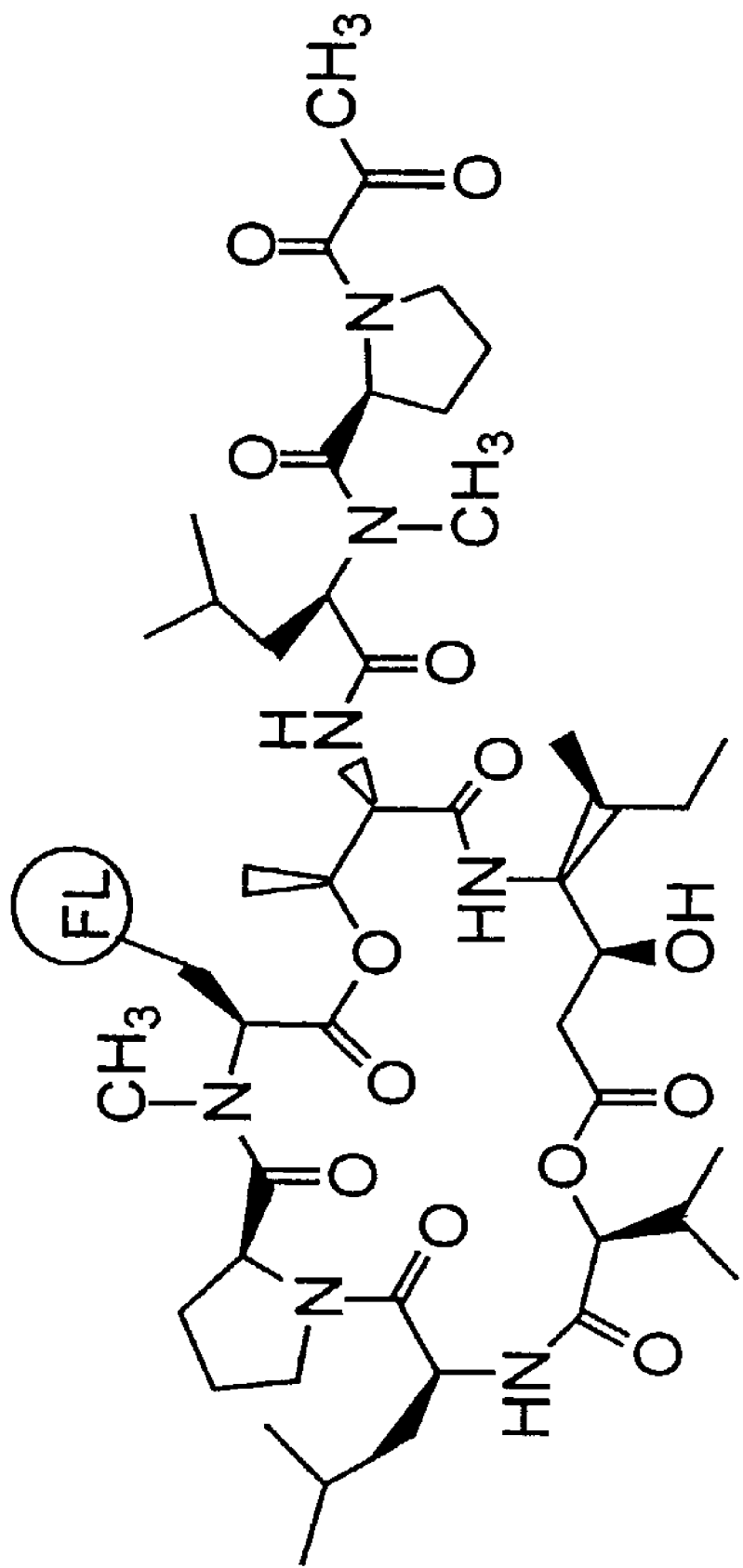
Fig. 29

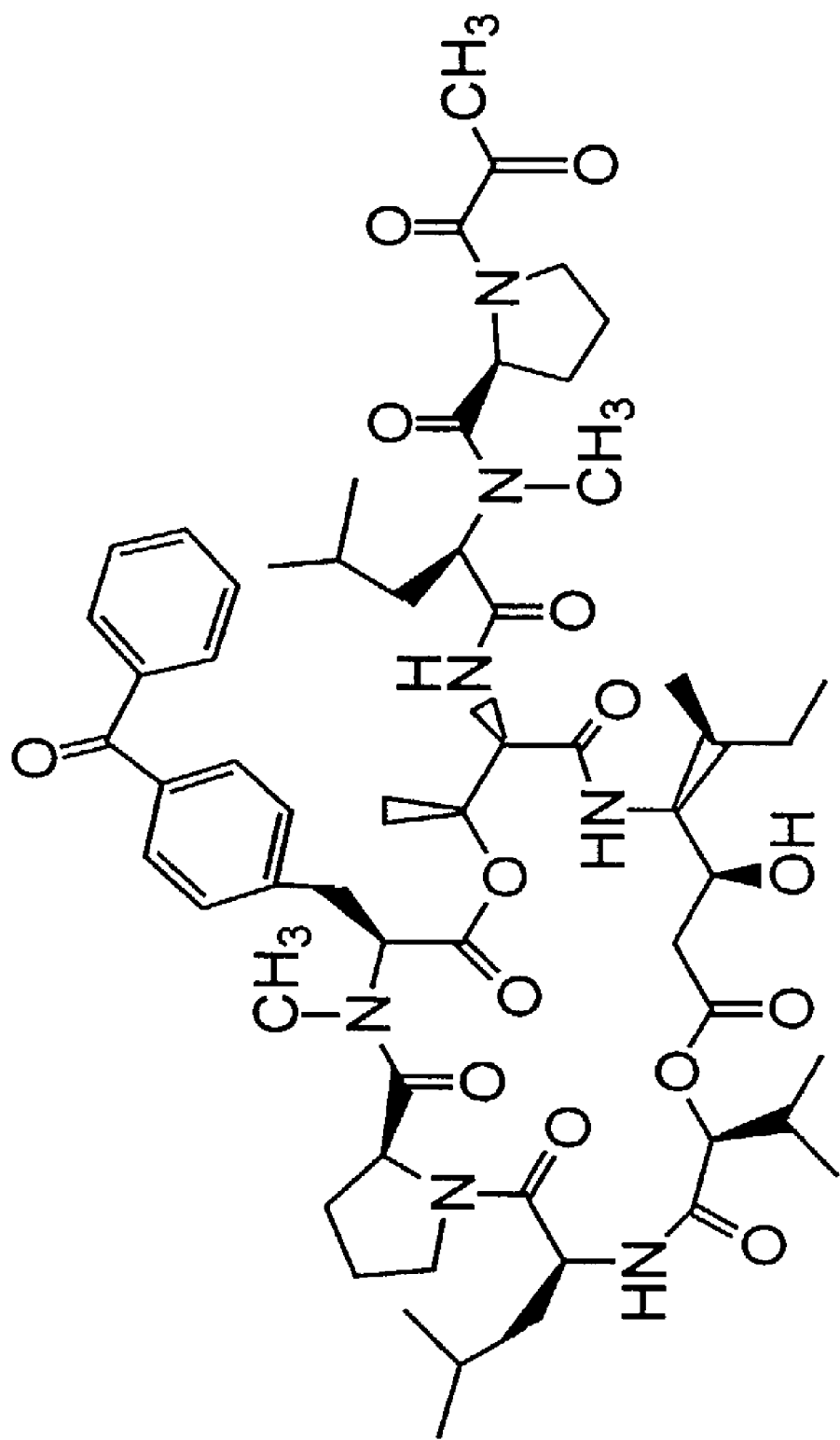
Fig. 30

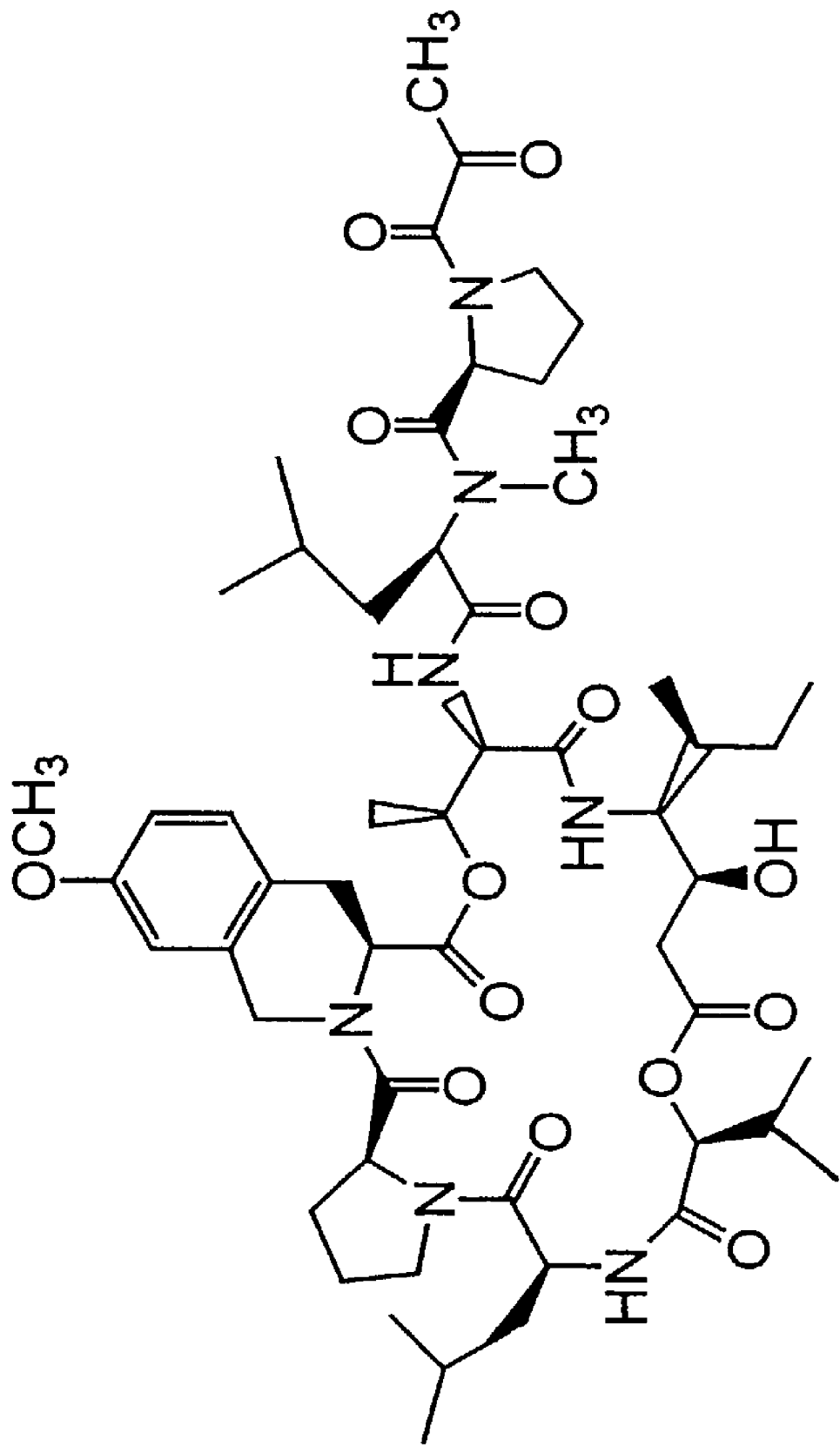
Fig. 31

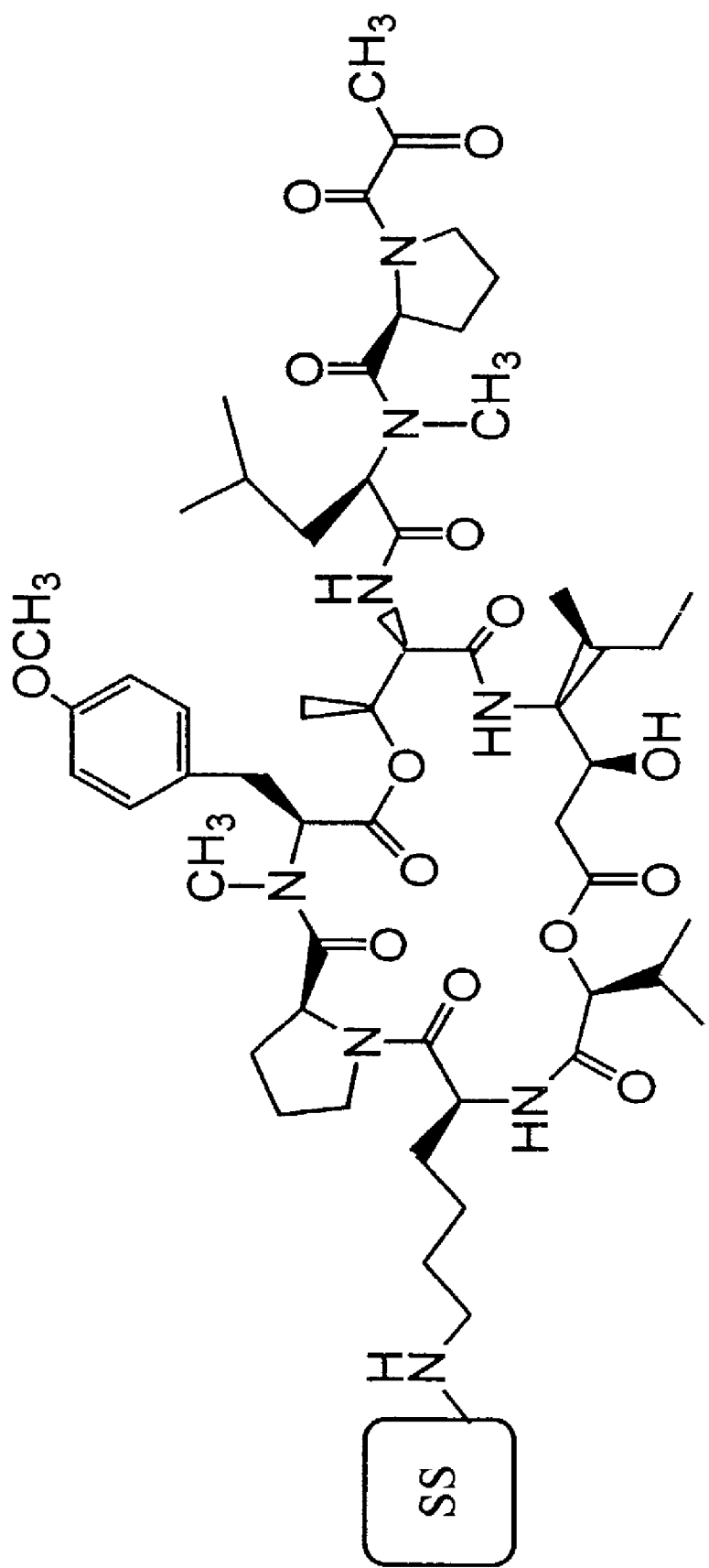
Fig. 32

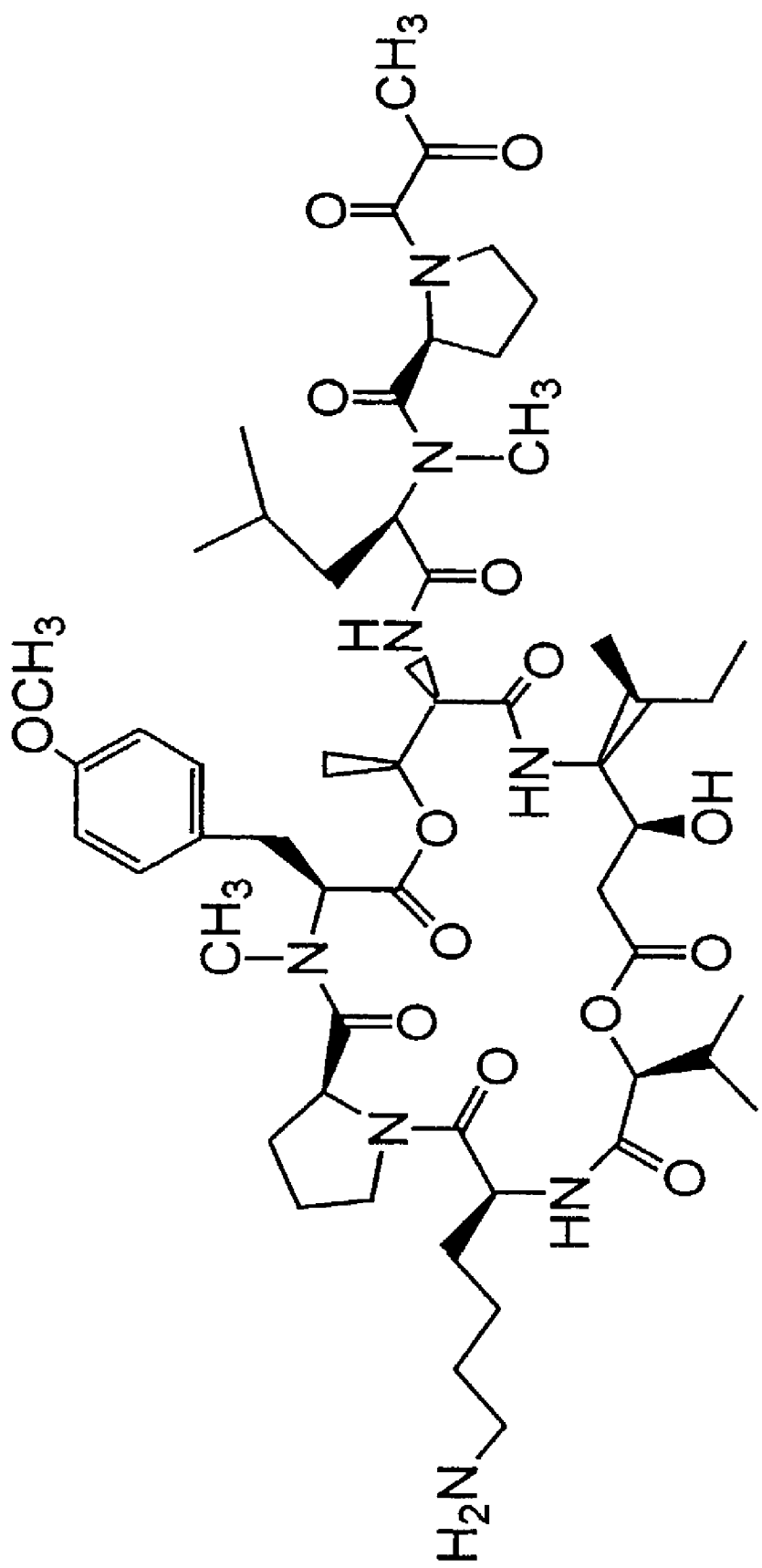
Fig. 33

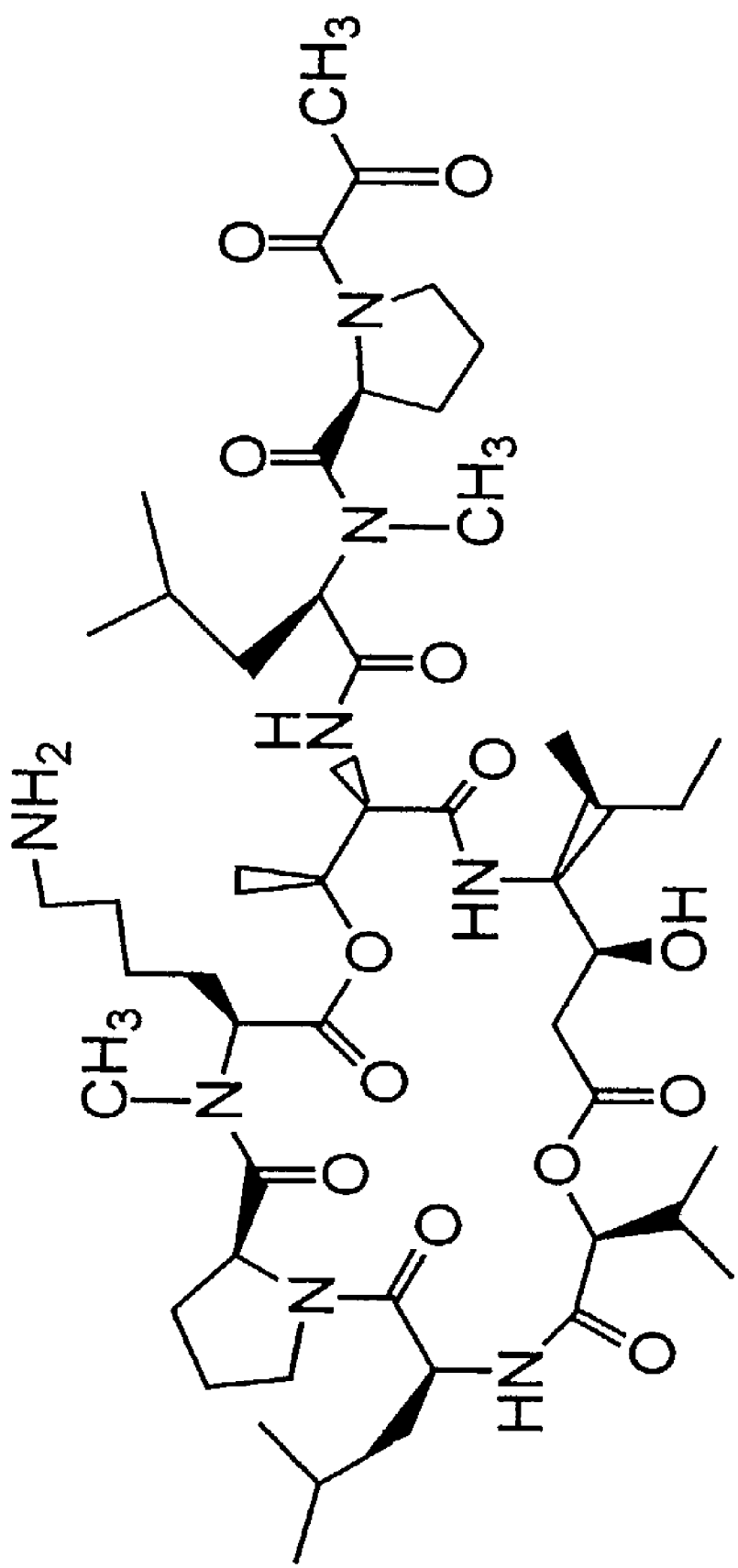
Fig. 34

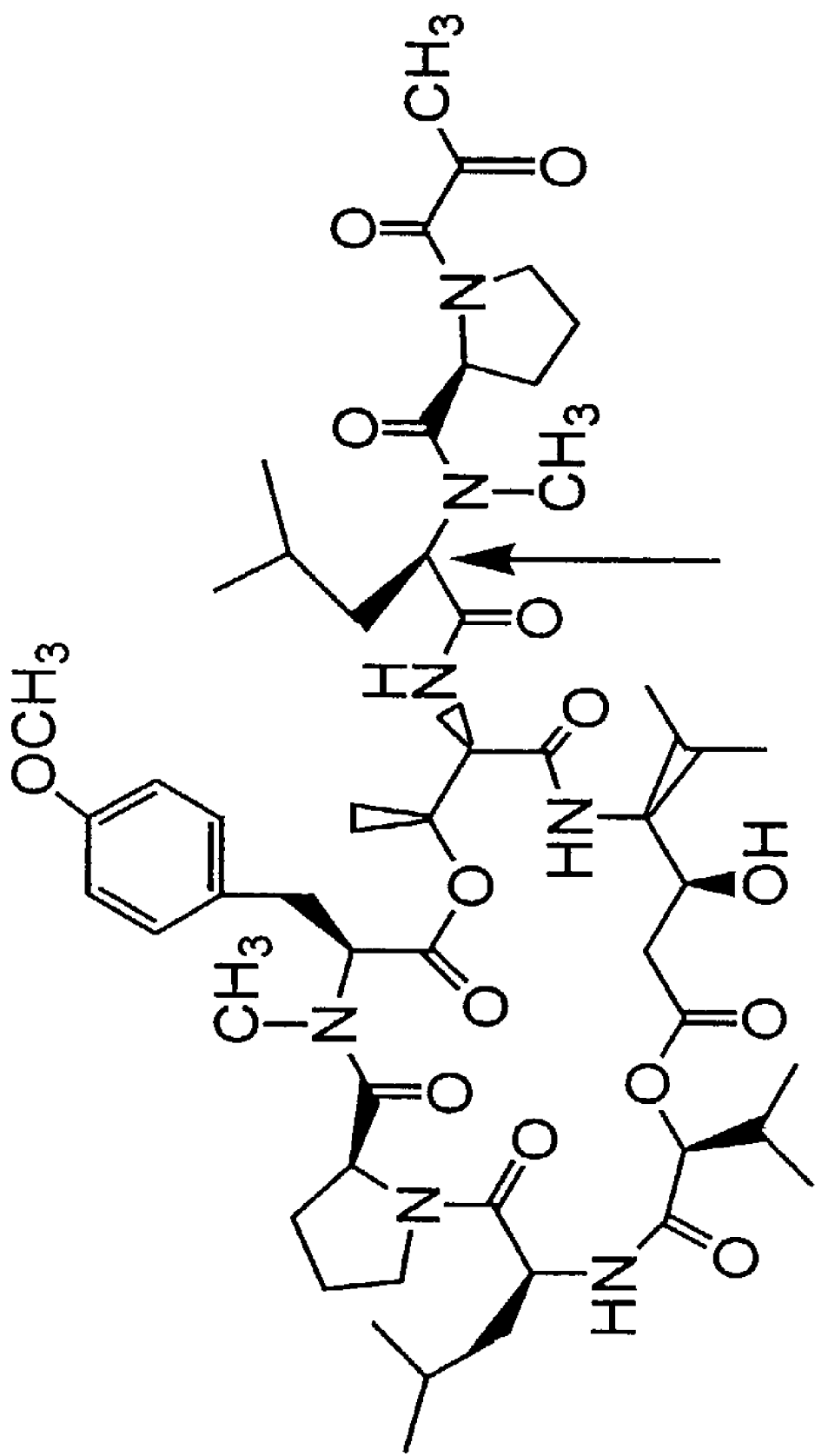
Fig. 35A

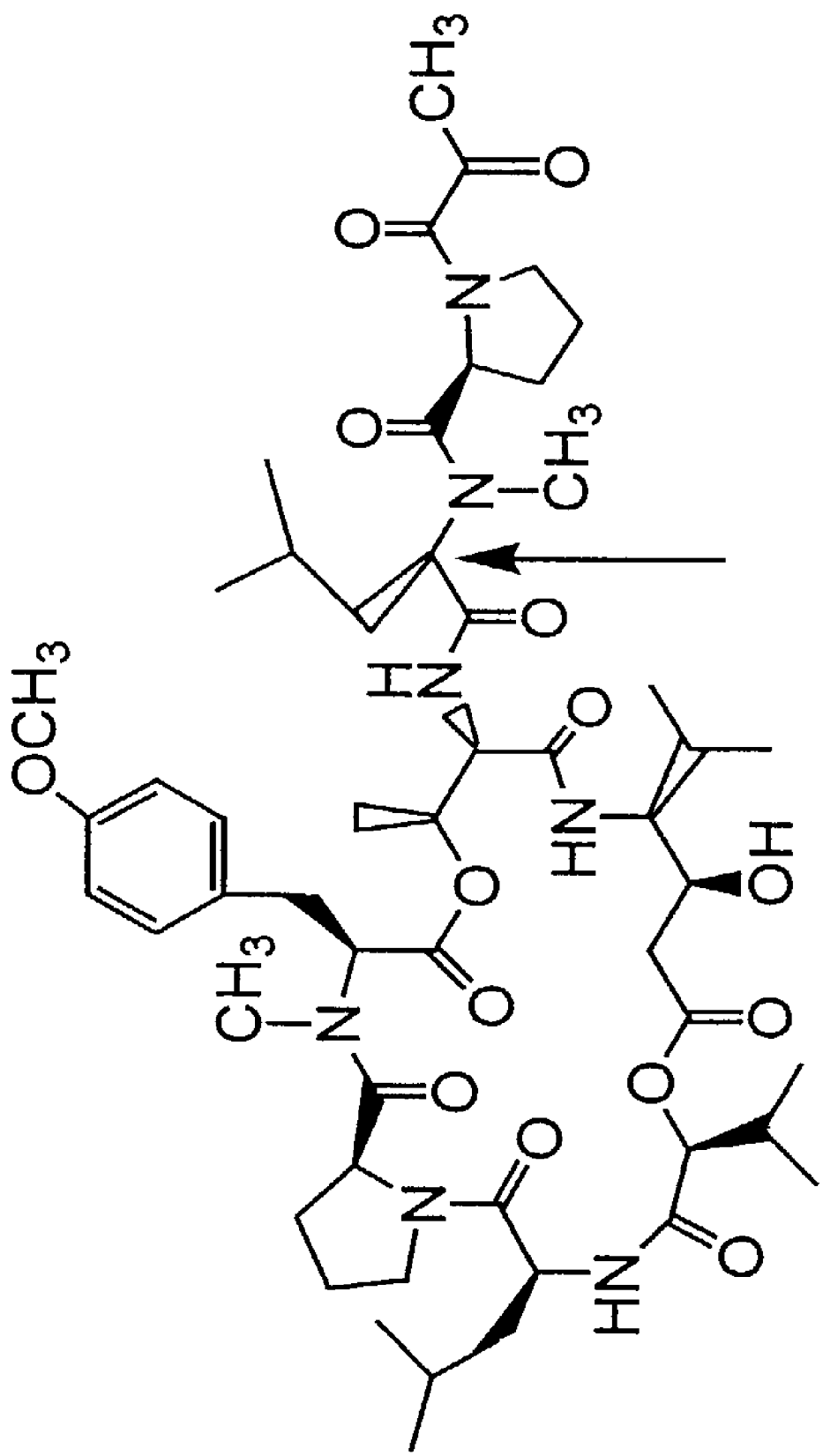
Fig. 35B

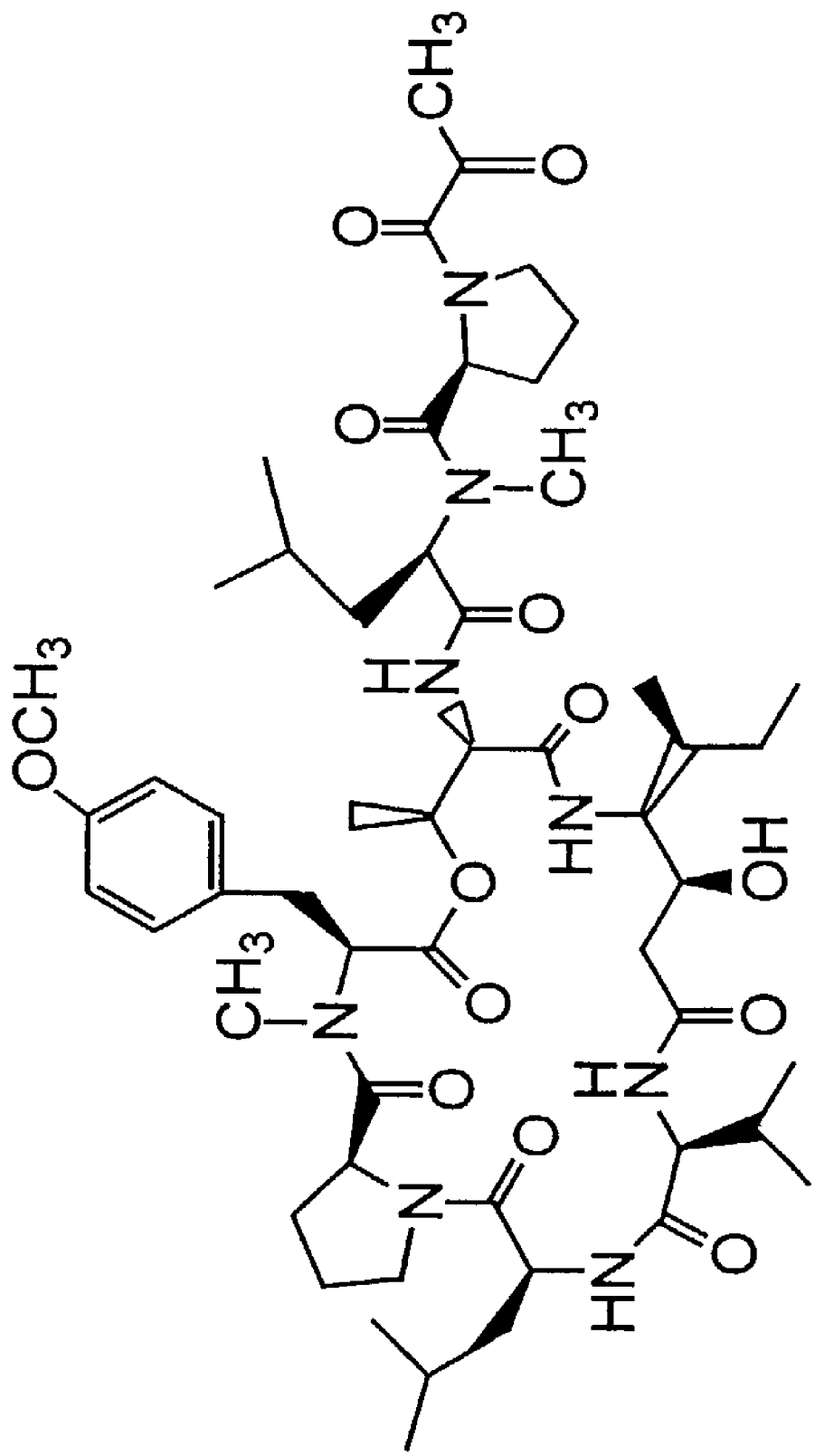
Fig. 36

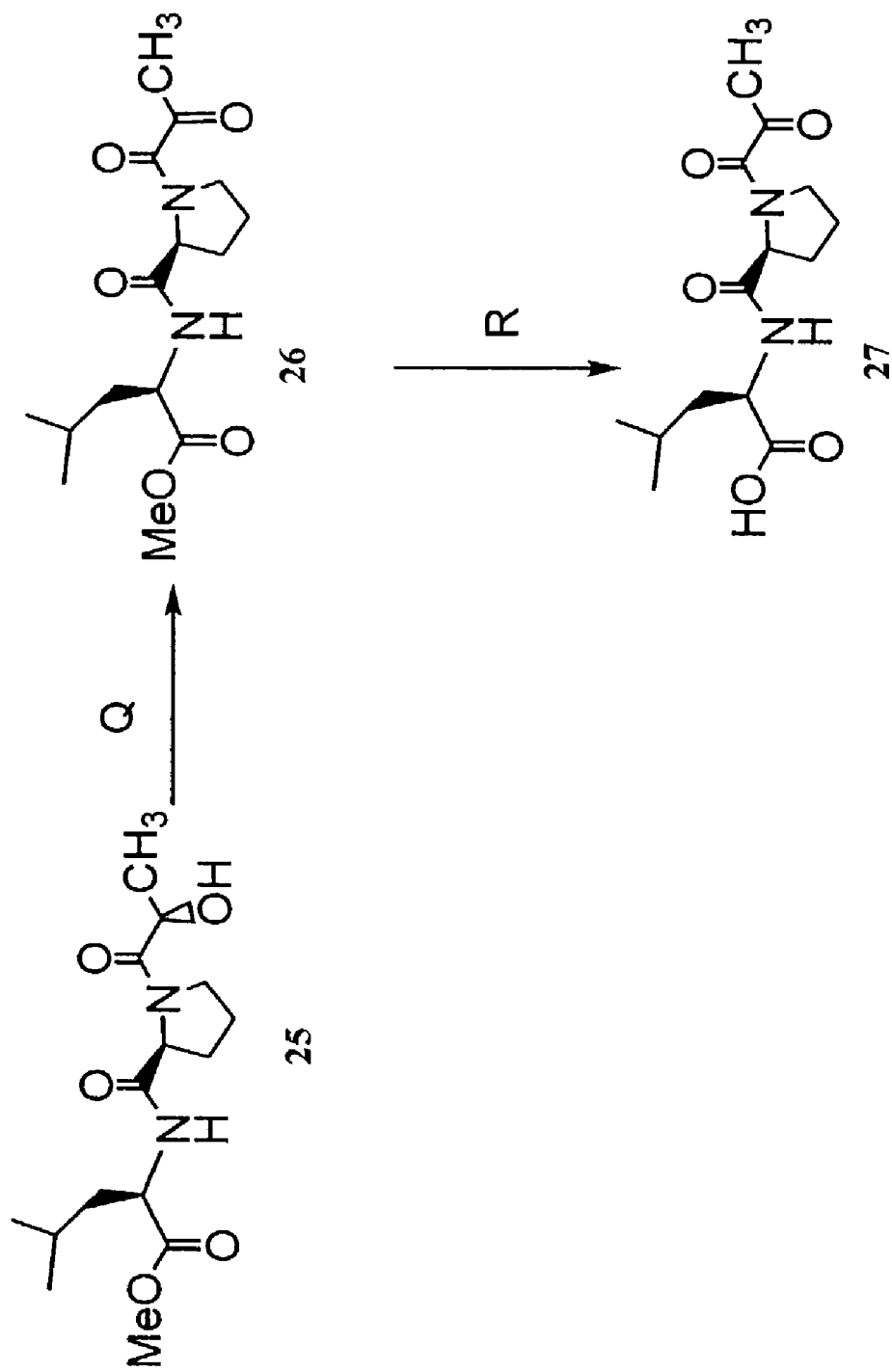
Fig. 37A

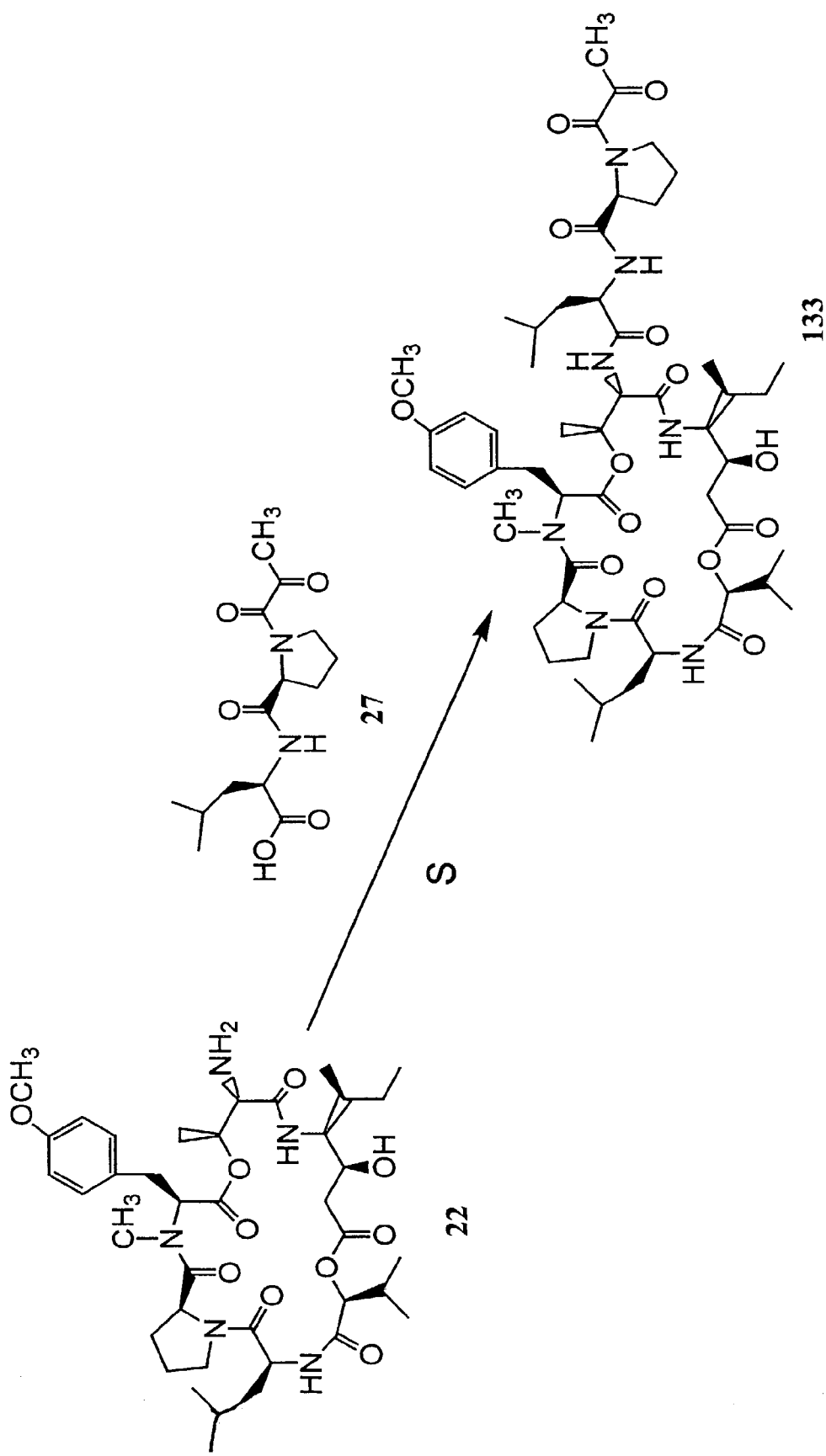
Fig. 37B

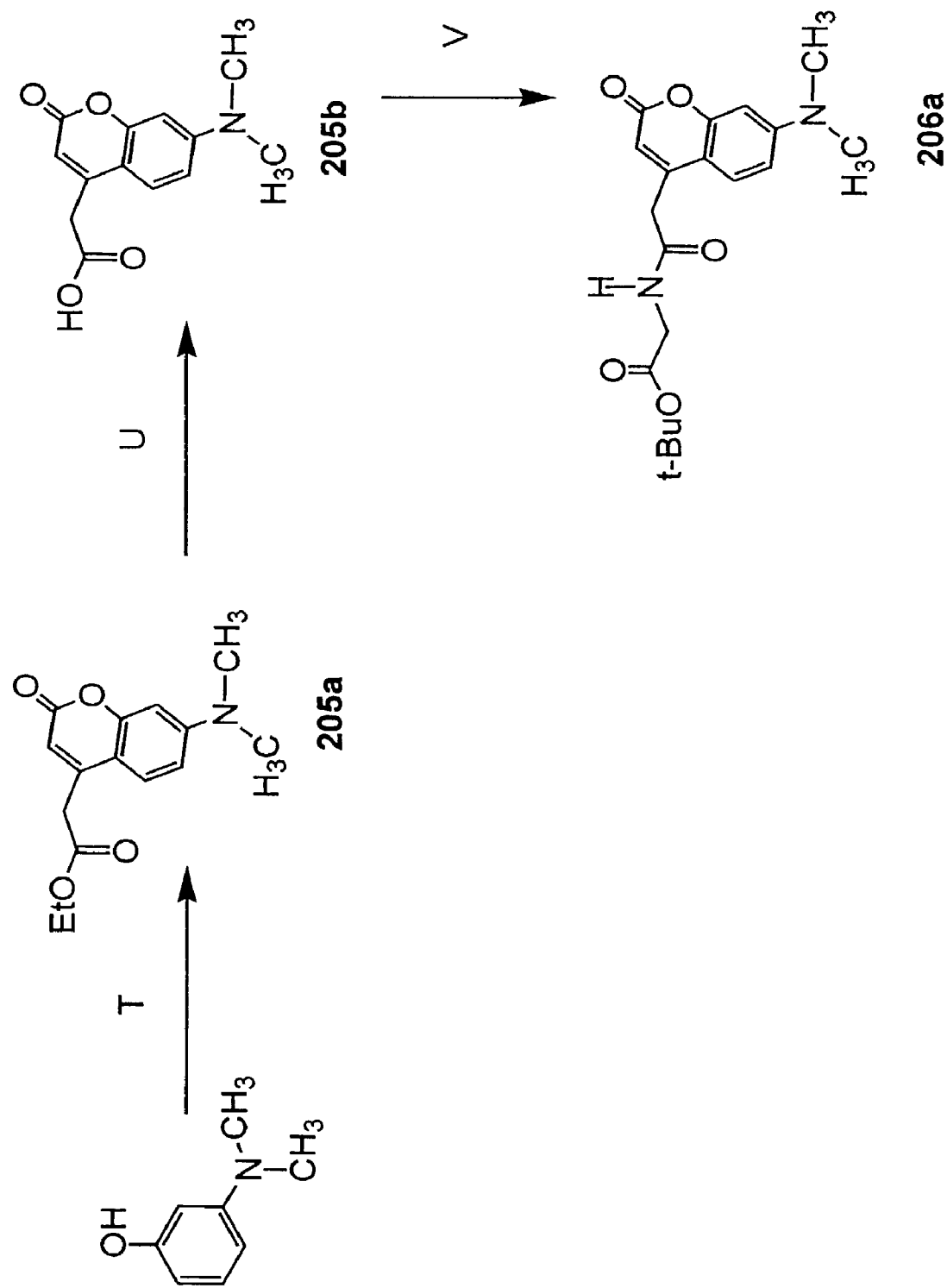
Fig. 38A

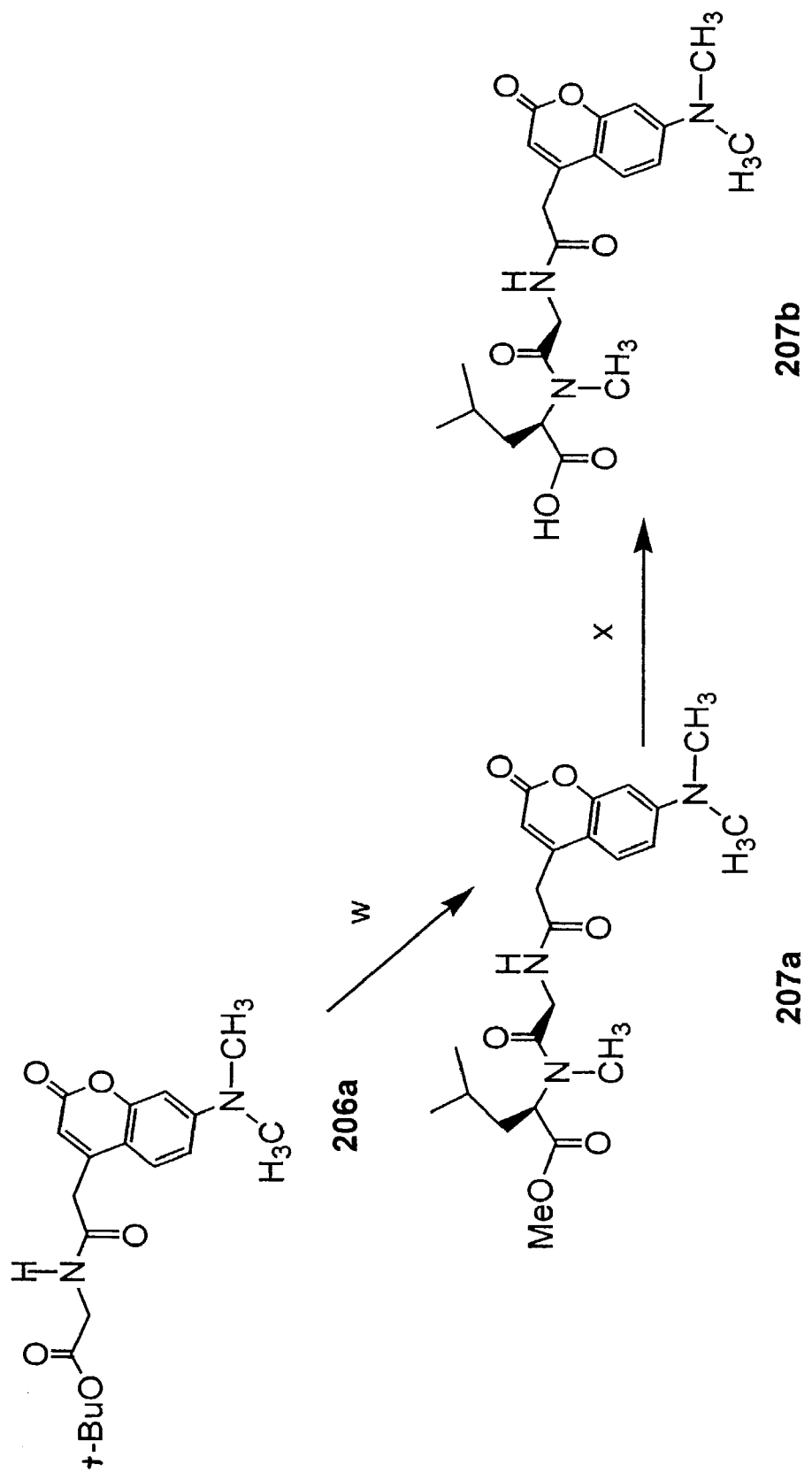
Fig. 38B

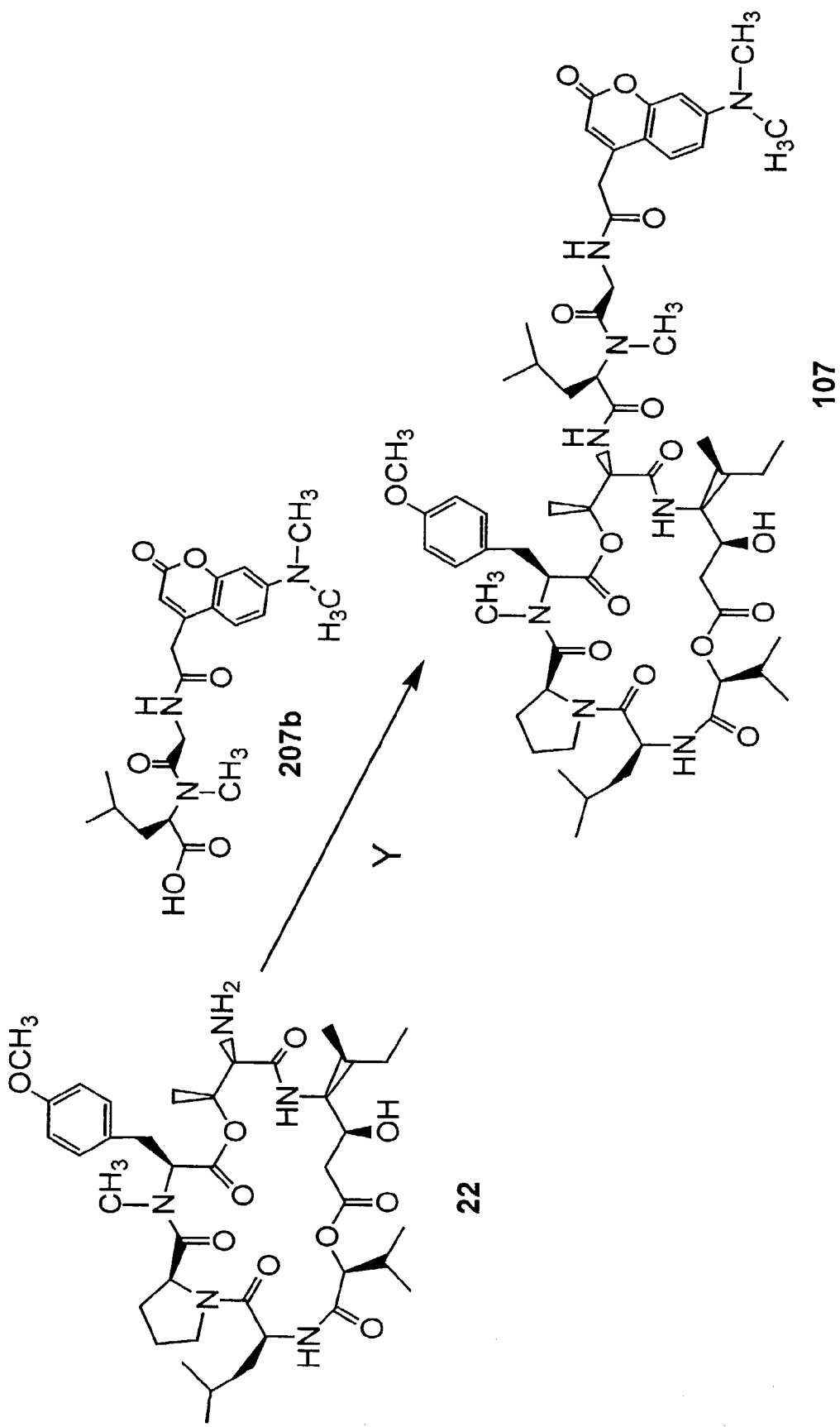
Fig. 38C

DIDEMNIN ANALOGS AND FRAGMENTS AND METHODS OF MAKING AND USING THEM

CROSS-REFERENCE TO RELATED APPLICATIONS

This application is a division of U.S. patent application Ser. No. 09/545,848, filed Apr. 7, 2000, now U.S. Pat. No. 6,509,315.

STATEMENT REGARDING FEDERALLY SPONSORED RESEARCH OR DEVELOPMENT

This research was supported in part by U.S. Government funds (NIH grant number CA40081), and the U.S. Government may therefore have certain rights in the invention.

REFERENCE TO A MICROFICHE APPENDIX

Not applicable.

BACKGROUND OF THE INVENTION

Didemnin B is a macrocyclic depsipeptide isolated from a species of marine tunicate. Didemnin B exhibits potent anti-viral, immunosuppressive, and anti-tumor activities in vitro and in vivo, and was the first marine natural product to enter clinical testing against human cancers (Li et al., 1992, Studies in Natural Products Chemistry, 10:241–302; Sakai et al., 1996, J. Med. Chem. 39:2819–2834; Wipf, 1995, Chem. Rev. 95:2115–2134). Didemnin B is a didemnin, a family of compounds which potently inhibit protein synthesis and cell cycle progression, and induce more rapid apoptosis than any other natural products that has been isolated to date (Grubb et al., 1995, Biochem. Biophys, Res. Commun. 215:1130–1136; Johnson et al., 1996, FEBS Lett. 383:1–5; Johnson et al., 1999, Immunol. Cell Biol. 77:242–248; Johnson et al., 1999, J. Cell. Biochem. 72:269–278). Other members of this family of compounds, including didemnin M and dehydrodidemnin B, exhibit cytotoxic and cytostatic effects as well.

Tamandarin A (also designated {(2S)HIV$^2$}didemnin B) is a naturally occurring didemnin analog which has recently been isolated from a marine tunicate. Tamandarin A exhibits biological activity which is analogous to the activities exhibited didemnin B. For example, tamandarin A is a potent inhibitor of protein synthesis, cell growth, and tumorigenesis. Tamandarin A exhibits greater in vitro activity against pancreatic carcinoma than does didemnin B (Liang et al., 1999, Org. Lett. 1: 1319–1322). A significant limitation on use of tamandarin A, either for research or for practical applications, is the limited supply of tamandarin A that is available from natural sources and the difficulty and expense of isolating this product. A need exists for a method of synthesizing tamandarin A and other didemnin analogs (including dehydrodidemnin analogs).

Despite the potency of didemnin B in isolated studies, its clinical effectiveness is hampered by side effects associated with therapeutic doses of the compound. As with many anti-proliferative agents, didemnin B exhibits a relatively narrow therapeutic window. Although didemnin M and dehydrodidemnin B exhibit improved therapeutic potential, relative to didemnin B, a need still exists for anti-proliferative agents which exhibit less toxicity at a therapeutic dose (i.e. didemnin analogs having a greater therapeutic index). The present invention satisfies the needs set forth above.

BRIEF SUMMARY OF THE INVENTION

The invention relates to a composition comprising a didemnin analog having the structure of formula I

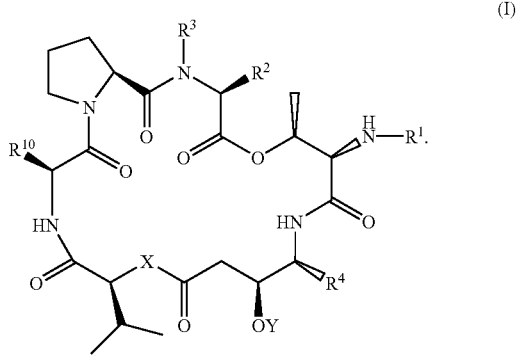

(I)

In formula I, $R^1$ is selected from the group consisting of
—H,
-(tert-butyloxycarbonyl),
-leucine,
—(N-methyl)leucine,
—(N-methyl)leucine-proline,
—(N-methyl)leucine-proline-lactate,
—(N-methyl)leucine-proline-pyruvate,
—(N-methyl)leucine-proline-lactate-(a first fluorophore),
—(N-methyl)leucine-proline-lactate-glutamine-pyroglutamate,
—(N-methyl)leucine-proline-lactate-glutamine-cyclopentanoate,
—(N-methyl)leucine-proline-alanine-leucine-pyroglutamate, and
—(N-methyl)leucine-proline-(N-methyl-alanine)-leucine-pyroglutamate.

$R^2$ and $R^3$ in formula I, can be separate moieties or they can, together, be a single moiety. When $R^2$ and $R^3$ are separate moieties, $R^3$ is either a methyl group or a hydride radical and $R^2$ is selected from the group consisting of an isoleucine side chain, a valine side chain, an alanine side chain, a norleucine side chain, a norvaline side chain, a leucine side chain, a histidine side chain, a tryptophan side chain, an arginine side chain, a lysine side chain, a second fluorophore, and a substituent having the structure of formula III

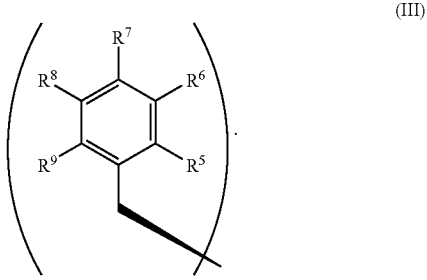

(III)

When $R^2$ and $R^3$ are, together, a single substituent, this substituent has the structure of formula IV

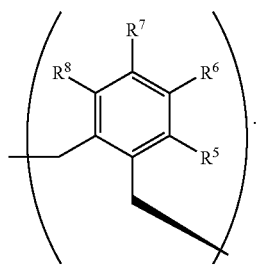
(IV)

In formulas III and IV, each of $R^5$, $R^6$, $R^7$, $R^8$, and $R^9$ is independently selected from the group consisting of —H, —OH, —OCH$_3$, —CO(C$_6$H$_5$), —Br, —I, —F, —Cl, —CH$_3$, and —C$_2$H$_5$;.

$R^4$ in formula I is either an isoleucine side chain or a valine side chain. Also, in formula I, X is either —O— or —(NH)—, Y is either a hydride radical or a hydroxyl protecting group, and $R^{10}$ is either a leucine side chain or a lysine side chain. The didemnin analog is an analog other than tamandarin A (i.e. {(2S)Hiv$^2$}didemnin B). In one embodiment, every proline or lactate moiety that is present in $R^1$ exhibits (S) stereochemistry. In another, every moiety capable of exhibiting stereochemistry in R1 is present in its naturally occurring form (i.e. the (S) form for amino acid residues and lactate. It is believed that cyclopentanoate occurs naturally in an (S) stereochemistry.

Examples of didemnin analogs that are included in the invention are compound 103, compound 104, compound 105, compound 106, compound 107, compound 108, compound 109, compound 110, compound 115, compound 116, compound 117, compound 118, compound 119, compound 120, compound 121, compound 122, compound 123, compound 124, compound 125, compound 126, compound 127, compound 128, compound 129, compound 130, compound 133, compound 134, compound 136, compound 137, compound 139, compound 141, compound 142, compound 143, In one embodiment, the didemnin analog has a photoreactive substituent, such as an $R^2$ moiety having the structure

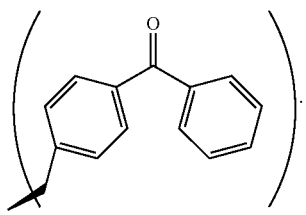

In another embodiment, the didemnin analog has a fluorophore attached, such as an analog in which a fluorophore is attached at the omega amino moiety of a lysine side chain at $R^2$ or at $R^{10}$. An example of the structure of such a fluorescent didemnin analog is show in FIG. 29. Alternatively, the didemnin analog can be attached (e.g. covalently) with a support. In most embodiments, Y in formula I is preferably a hydride radical.

The invention includes an embodiment of a didemnin analog which can be activated (or the activity of which can be enhanced) by enzymatic cleavage of a moiety bound with the analog. For example, the invention includes compositions which comprise a didemnin analog having the structure of formula II

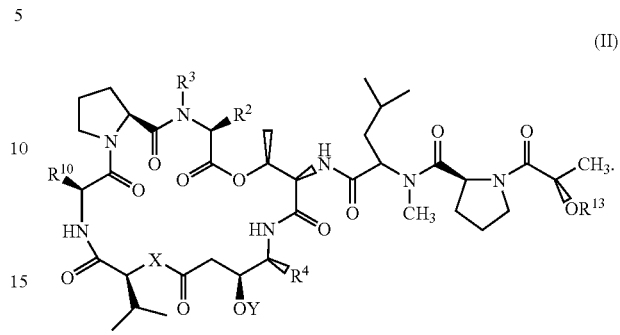
(II)

In formula II, $R^2$, R3, $R^4$, $R^{10}$, X, and Y have the same identities described above for formula I. $R^{13}$ is an enzyme-cleavable moiety that is cleavable by an enzyme, such as one selected from the group consisting of a carboxypeptidase, a beta-lactamase, a beta-galactosidase, a penicillin V-amidase, a cytosine deaminase, a nitroreductase, a alkaline phosphatase, a beta-glucuronidase, and a catalytic antibody. By way of example, $R^{13}$ can have the structure of either of formulas V and VI

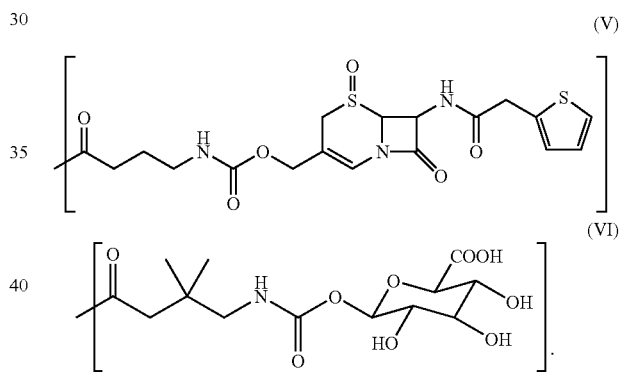
(V)

(VI)

Examples of such didemnin analogs include compound 131 and compound 132.

The invention also relates to compositions which comprise a didemnin fragment having the structure of formula VII

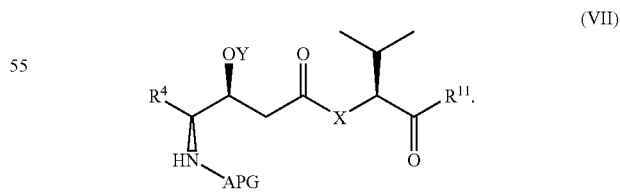
(VII)

In formula VII, Y is either a hydride radical or a hydroxyl protecting group, X is either —O— or —(NH)—, $R^4$ is either an isoleucine side chain or a valine side chain, and APG is a amine protecting group. $R^{11}$ can be any of —OH, —NH$_2$, —O(allyl), —O(pentafluorophenyl), and a substituent having the structure of formula VIII

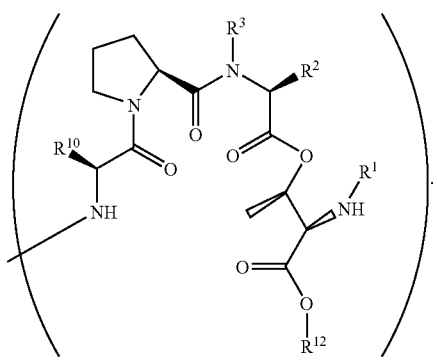

(VIII)

In formula VIII, $R^1$, $R^2$, $R^3$, and $R^{10}$ have the same identities described above for formula I, and $R^{12}$ can be either a hydride radical or a -2-(trimethylsilyl)ethoxycarbonyl moiety.

The didemnin analogs and fragments described herein can be formulated, together with one or more pharmaceutically acceptable carriers, to make pharmaceutical preparations. These preparations can be administered to a mammalian (e.g. human) cell (i.e. either in vitro or in vivo) in order to inhibit protein synthesis, inhibit growth, inhibit proliferation, inhibiting tumorigenesis, or enhance apoptosis in the cell or in one or more tissues of the mammal.

The invention further includes a method of making a didemnin fragment. This method comprises coupling a first reactant having the structure

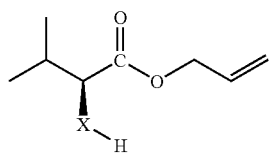

and a second reactant having the structure

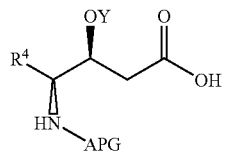

to yield a first didemnin fragment having the structure

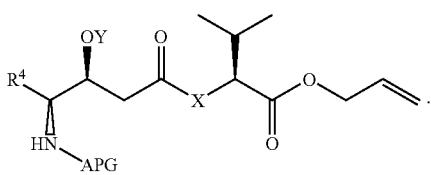

In this structure, X is either —O— or —(NH)—, APG is an amine protecting group; Y is a hydroxyl protecting group (e.g. a-triisopropylsilyl group), and $R^4$ can be either an isoleucine side chain or a valine side chain. The first didemnin fragment can be hydrolyzed to yield a second didemnin fragment having the structure

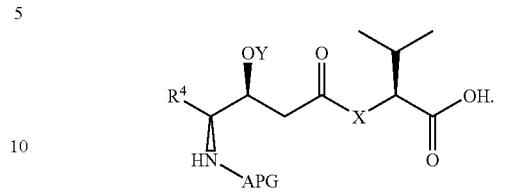

An activator (ACT) can be added to the carbonyl moiety of the second didemnin fragment to yield a third didemnin fragment having the structure

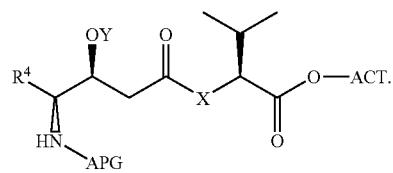

The third didemnin fragment can be coupled with a third reactant which has the structure

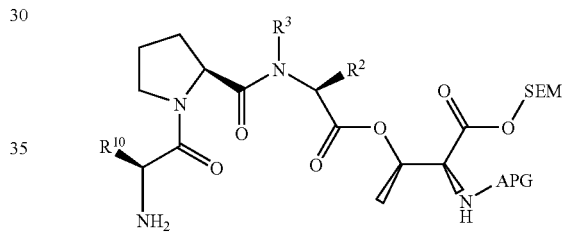

to yield a fourth didemnin fragment having the structure

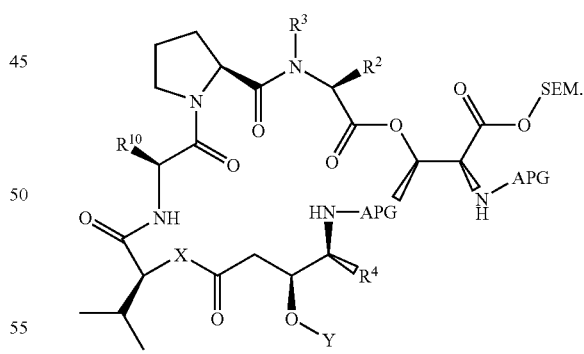

In this structure, $R^2$ and $R^3$ have the identities described above for formula I, APG is an amine protecting group, SEM is a 2-(trimethylsilyl)ethoxycarbonyl group, and $R^{10}$ is either a leucine side chain or a lysine side chain.

The invention also relates to a method of making a didemnin analog from the fourth didemnin fragment. This method comprises removing the SEM and CBZ moieties from the fourth didemnin fragment and cyclizing the fragment to yield a first didemnin analog having the following structure.

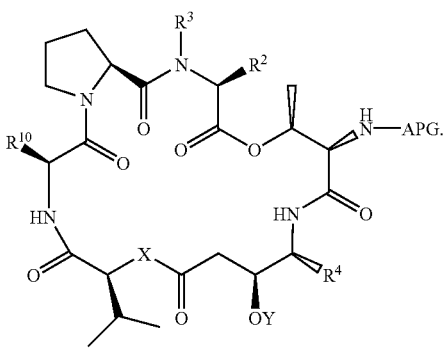

The APG group (which can, for example, be a carbobenzyloxy moiety or a tert-butyloxycarbonyl moiety) can be removed from the first didemnin analog to yield a second didemnin analog having the structure

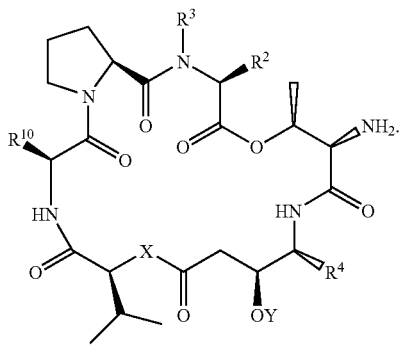

This second didemnin analog can be coupled with a fourth reagent having the structure

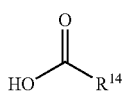

to yield a third didemnin analog having the structure

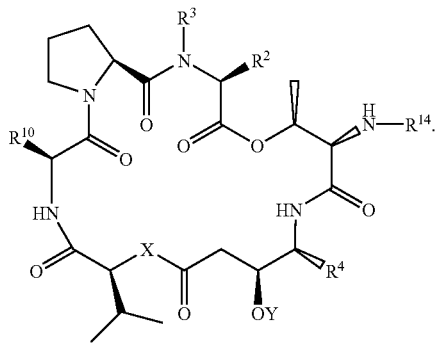

In these structures, $R^{14}$ is can be one of
—leucine,
—(N-methyl)leucine,
—(N-methyl)leucine-(S)proline,
—(N-methyl)leucine-(S)proline-pyruvate,
—(N-methyl)leucine-(S)proline-(S)lactate,
—(N-methyl)leucine-(S)proline-(S)lactate-(a first fluorophore),
—(N-methyl)leucine-(S)proline-(S)lactate-(S)glutamine-(S)pyroglutamate,
—(N-methyl)leucine-(S)proline-(S)lactate-(S)glutamine-(S)cyclopentanoate,
—(N-methyl)leucine-(S)proline-(S)alanine-(S)leucine-(S)pyroglutamate, and
—(N-methyl)leucine-(S)proline-(N-methyl-S-alanine)-(S)-leucine-(S)pyroglutamate, or it can be one of these moieties coupled with an enzyme-cleavable moiety that is cleavable by an enzyme such as one of a carboxypeptidase, a beta-lactamase, a beta-galactosidase, a penicillin V-amidase, a cytosine deaminase, a nitroreductase, an alkaline phosphatase, a beta-glucuronidase, and a catalytic antibody. If Y is a hydroxyl protecting group, then that can be removed from the third didemnin analog (either before or after addition of $R^{14}$) to yield a fourth didemnin analog having the structure

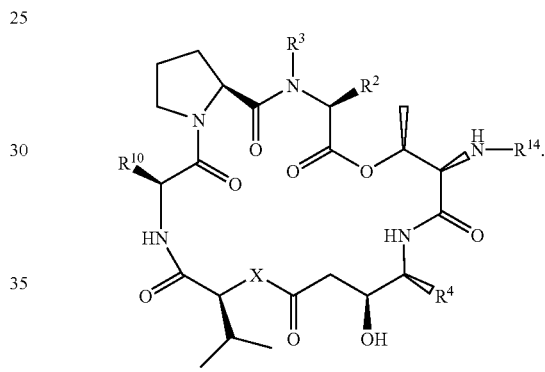

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

FIG. 1, comprising FIGS. 1A and 1B, depicts the structure of tamandarin A (i.e. {(2S)HIV²}didemnin B). FIG. 1A is the structure of (−) tamandarin A (compound 101). FIG. 1B is the structure of a diastereomer (compound 102) of (−) tamandarin A. The chiral center at which these two molecules differ is indicated with an arrow.

FIG. 2, comprising FIGS. 2A and 2B, depicts the structure of tamandarin M (i.e. {(2S)HIV²}didemnin M). FIG. 2A is the structure of (−) tamandarin M (compound 103). FIG. 2B is the structure of a diastereomer (compound 104) of (−) tamandarin M. The chiral center at which these two molecules differ is indicated with an arrow.

FIG. 3, comprising FIGS. 3A and 3B, depicts the structure of tamandarin B (i.e. {(2S)HIV²}didemnin B). FIG. 3A is the structure of (−) tamandarin B (compound 105).

FIG. 3B is the structure of a diastereomer (compound 106) of (−) tamandarin B. The chiral center at which these two molecules differ is indicated with an arrow.

FIG. 4, comprising FIGS. 4A, 4B, 4C, and 4D, depicts the structure of several fluorescent tamandarin-type didemnin analogs. FIG. 4A is the structure of compound 107. FIG. 4B is the structure of compound 108. The chiral center at which compounds 107 and 108 differ is indicated with an arrow. FIG. 4C is the structure of compound 109. FIG. 4D is the structure of compound 110. The chiral center at which compounds 109 and 110 differ is indicated with an arrow.

FIG. 5, comprising FIGS. 5A and 5B, depicts a class of immobilizable tamandarin-type didemnin analogs. FIG. 5A is the structure of a didemnin analog of formula I herein, wherein $R^{10}$ is a lysine side chain. FIG. 5B is the structure of the didemnin analog of FIG. 5A bound with a solid support (SS).

FIG. 6, comprising FIGS. 6A and 6B, depicts another class of immobilizable tamandarin-type didemnin analogs. FIG. 6A is the structure of didemnin analog of formula I herein, wherein $R^1$ is -leucine. FIG. 6B is the structure of the didemnin analog of FIG. 6A bound with a solid support (SS).

FIG. 7 is the structure of compound 115.
FIG. 8 is the structure of compound 116.
FIG. 9 is the structure of compound 117.
FIG. 10 is the structure of compound 118.
FIG. 11 is the structure of compound 119.
FIG. 12 is the structure of compound 120.
FIG. 13 is the structure of compound 121.
FIG. 14 is the structure of compound 122.
FIG. 15 is the structure of compound 123.
FIG. 16 is the structure of compound 124.
FIG. 17 is the structure of compound 125.
FIG. 18 is the structure of compound 126.
FIG. 19 is the structure of compound 127.
FIG. 20 is the structure of compound 128.
FIG. 21 is the structure of compound 129.
FIG. 22 is the structure of compound 130.

FIG. 23 depicts enzymatic cleavage of the cephalosporin moiety of didemnin analog 131 by beta-lactamase to yield compound 101.

FIG. 24 depicts enzymatic cleavage of the glucoside moiety of didemnin analog 132 by beta-glucuronidase to yield compound 101.

FIG. 25, comprising FIGS. 25A and 25B, is a pair of structures which illustrates the structural difference between tamandarin A (101; FIG. 25A, and didemnin B (201; FIG. 25B. The macrocyclic core of 101 differs from that of 201 in that 101 contains an alpha-hydroxyisovaleryl (Hiv) moiety, and 201 contains an alpha-(alpha-hydroxyisovaleryl)-propionyl (Hip) moiety at the analogous position, as indicated by the brackets and dotted lines in each of the figures.

FIG. 26, comprising FIGS. 26A–26E, depicts a synthetic method for generating didemnin analogs described herein.

FIG. 27, is the structure of (−) Tamandarin A (i.e. {(2S) $HIV^2$} didemnin B), illustrating the numbering convention used herein and in Sakai et al. (1996, J. Med. Chem. 39:2819–2834) for didemnin analogs.

FIG. 28, comprising FIGS. 28A and 28B, depicts the structure of a dehydrotamandarin-type didemnin analog (i.e. {(2S)$HIV^2$}dehydrodidemnin B). FIG. 28A is the structure of (−) dehydrotamandarin (compound 133). FIG. 28B is the structure of a diastereomer of (−) dehydrotamandarin (compound 134). The chiral center at which these two molecules differ is indicated with an arrow. The position at which dehydrotamandarin-type didemnin analogs differ from tamandarin-type didemnin analogs is indicated with an asterisk.

FIG. 29 is the structure of a fluorescent dehydrotamandarin-type didemnin analog. "FL" is a fluorophore.

FIG. 30 is the structure of compound 136.
FIG. 31 is the structure of compound 137.
FIG. 32 depicts a dehydrotamandarin-type didemnin analog bound with a solid support (SS).
FIG. 33 is the structure of compound 139.
FIG. 34 is the structure of compound 140

FIG. 35, comprising FIGS. 35A and 35B, depicts the structure of dehydrotamandarin B, also designated {(2S) $Hiv^2$, Norsta$^1$}didemnin B. FIG. 35A is the structure of (−) dehydrotamandarin B (compound 141). FIG. 35B is the structure of a diastereomer of (−) dehydrotamandarin B (compound 142). The chiral center at which these two molecules differ is indicated with an arrow.

FIG. 36 is the structure of compound 143

FIG. 37, comprising FIGS. 37A and 37B, depicts a synthetic method for generating (−) dehydrotamandarin (i.e. {(2S)$HIV^2$}dehydrodidemnin B, compound 133).

FIG. 38, comprising FIGS. 38A, 38B, and 38C, depicts a synthetic method for generating fluorescent didemnin analogs described herein.

DETAILED DESCRIPTION OF THE INVENTION

The invention relates to didemnin analogs, compositions comprising such analogs, and methods for making and using these analogs. The didemnin analogs described herein include tamandarin-type, dehydrotamandarin-type didemnin analogs, and fragments of these analogs. These analogs and fragments are useful for, among other things, inhibiting protein synthesis, cell growth, cell proliferation, and tumorigenesis. The analogs of the invention can also exhibit anti-viral, anti-tumor, apoptosis-inducing, and immunosuppressive activities in animals, including in humans.

The invention includes compositions comprising a didemnin analog having the structure

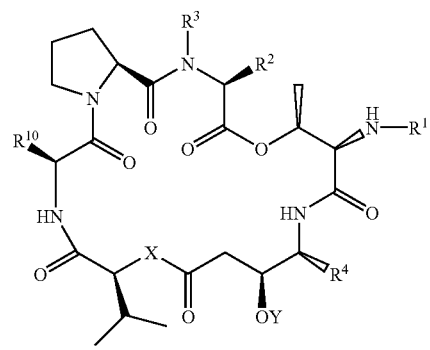

wherein $R^1$, $R^2$, $R^3$, $R^4$, $R^{10}$, X, and Y have the identities described herein. Examples of didemnin analogs according to this formula are shown in the figures.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, amino acid residues are represented by the full name thereof, by the three letter code corresponding thereto, or by the one-letter code corresponding thereto, as indicated by the following:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "amino acid side chain" refers to a moiety comprising all of the atoms of an amino acid excluding the alpha-carbon atom, a hydrogen atom bound with the alpha-carbon, the atoms of the alpha-carboxyl moiety and the alpha-amine moiety. By way of example, an "alanine side chain" refers to a methyl group, and a "valine side chain" refers to a 2-propyl group.

"Inhibition" of a process in a cell (e.g. inhibition of protein synthesis, inhibition of cell growth, inhibition of cell cycle progression, inhibition of cell proliferation, or inhibition of tumorigenesis) means reduction (e.g. by at least 10%, 25%, 50%, 75%, 90%, 95%, or even 100%) of the rate at which the process proceeds, reduction (e.g. by at least 10%, 25%, 50%, 75%, 90%, 95%, or even 100%) of the rate at which the process is initiated, or both.

"Enhancement" of a process in a cell (e.g. enhancement of apoptosis) means increasing (e.g. by at least 10%, 25%, 50%, 75%, 90%, 95%, or even 100%) the rate at which the process proceeds, increasing (e.g. by at least 10%, 25%, 50%, 75%, 90%, 95%, or even 100%) the rate at which the process is initiated, or both.

As used herein, the term "pharmaceutically acceptable carrier" means a chemical composition with which a didemnin analog or fragment, as described herein, can be combined and which, following the combination, can be administered to a subject (e.g. a human or other animal).

As used herein, the term "physiologically acceptable" ester or salt means an ester or salt form of a didemnin analog or fragment, as described herein, which is compatible with other ingredients of a pharmaceutical composition and which is not deleterious to a subject to which the composition is to be administered.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration can include, but is not limited to, subcutaneous, intraperitoneal, intramuscular, intrasternal injection, and kidney dialytic infusion techniques.

As used herein, the term "anti-viral activity" means preventing replication of a virus in the cell, preventing infection of the cell by a virus, or reversing a physiological effect of infection of the cell by a virus. An anti-viral agent a composition of matter which, when delivered to a cell, exhibits anti-viral activities. Anti-viral agents are well known and described in the literature. By way of example, AZT (zidovudine, RETROVIR Glaxo Wellcome Inc., Research Triangle Park, N.C.) is an anti-viral agent which is thought to prevent replication of HIV in human cells.

As used herein, the term "anti-viral activity" means preventing replication of a virus in the cell, preventing infection of the cell by a virus, or reversing a physiological effect of infection of the cell by a virus. An anti-viral agent a composition of matter which, when delivered to a cell, exhibits anti-viral activities. Anti-viral agents are well known and described in the literature. By way of example, AZT (zidovudine, RETROVIR Glaxo Wellcome Inc., Research Triangle Park, N.C.) is an anti-viral agent which is thought to prevent replication of HIV in human cells.

Description

The present invention relates to a didemnin analogs (including tamandarin-type and dehydrotamandarin-type analogs, as described herein) and to particular fragments of such analogs, which exhibit potent pharmacological properties when administered to humans and other mammals. By way of example, these compounds can inhibit protein synthesis and cell growth and proliferation. These compounds can also enhance apoptosis in cells. These properties render the compounds useful for treating a variety of disorders which are characterized by one or more of aberrant protein synthesis, aberrant cell growth, aberrant proliferation of cells, and aberrant apoptosis. Examples of such disorders include tumorigenesis, tumor growth, tumor metastasis, infection of a cell by a virus, replication of a virus within a cell.

Among the compositions of the inventions are those which comprise a didemnin analog having the structure of formula I

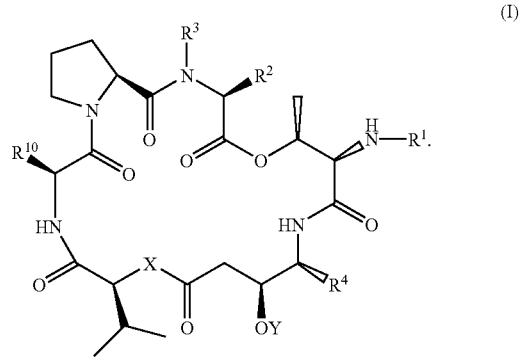

The $R^1$ substituent of formula I can, for example, be a hydrogen atom or an amine protecting group suitable for protection of amino acids. Such protecting groups are known in the art and referred to throughout this disclosure. Examples of suitable protecting groups can be found in references such as Green and Wutz (1999, Protecting Groups in Organic Synthesis, Wiley, New York) and Bodansky (1993, Principles of Peptide Synthesis, Springer, Berlin). Alternatively, the $R^1$ substituent can be an amino acid residue (e.g. a leucine residue) or a polypeptide comprising two or more amino acid residues. Examples of such polypeptides include
—(N-methyl)leucine,
—(N-methyl)leucine-proline,
—(N-methyl)leucine-proline-lactate,
—(N-methyl)leucine-proline-pyruvate,
—(N-methyl)leucine-proline-lactate-glutamine-pyroglutamate,
—(N-methyl)leucine-proline-lactate-glutamine-cyclopentanoate,
—(N-methyl)leucine-proline-lactate-leucine-pyroglutamate,
—(N-methyl)leucine-proline-alanine-leucine-pyroglutamate, and
—(N-methyl)leucine-proline-(N-methyl)alanine-leucine-pyroglutamate.

Additional examples of alternative $R^1$ substituents include peptides which comprise a fluorophore, and an amino acid residue, a polypeptide, or another chemical moiety bound (e.g. covalently attached) with a support (e.g. a glass or silica plate, an agarose or other polymeric bead, etc.). When $R^1$ comprises an N-methyl-leucine residue, the alpha-carbon atom of that residue can have either (R) or (S) stereochemistry. Other amino acid residues within $R^1$ can have either (R) or (S) stereochemistry, but they preferably have (S) stereochemistry at their alpha-carbon atom. When $R^1$ comprises a lactate residue, the lactate residue is preferably an (S)lactate residue. In a preferable embodiment, every amino acid residue within $R^1$ other than the leucine (or N-methyl-leucine) residue (if present) attached directly to the nitrogen atom of the ring of formula I has (S) stereochemistry.

$R^3$ can be either of —$CH_3$ and —H. Alternatively, $R^3$ can, together with $R^2$, be a single substituent.

The $R^2$ substituent can be an amino acid side chain such as an isoleucine side chain (i.e. a 2-butyl moiety, preferably having (R) stereochemistry), a valine side chain (i.e. a 2-propyl moiety), an alanine side chain (i.e. a methyl moiety), a norleucine side chain (i.e. a 1-butyl moiety), a norvaline side chain (i.e. a 1-propyl moiety), a leucine side chain (i.e. an isobutyl moiety, preferably having (S) stereochemistry), a phenylalanine side chain (i.e. a phenylmethyl moiety), a histidine side chain (i.e. a 4-methyl-imidazole moiety), a tryptophan side chain (i.e. a 3-methyl-indole moiety), a tyrosine side chain (i.e. a 4-hydroxy-phenylmethyl moiety), an arginine side chain (i.e. a 4-guanidinyl-butyl moiety), and a lysine side chain (i.e. a 4-aminobutyl moiety).

An $R^2$ substituent can comprise a fluorophore (e.g. a fluorophore linked with one of the amino acid side chains described above). In addition, $R^2$ substituent can have the structure of formula III

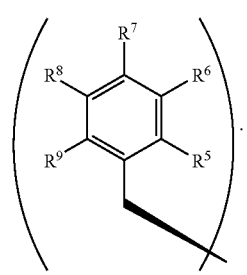

(III)

In an alternative embodiment, $R^2$ and $R^3$ together are a substituent having the structure of formula IV

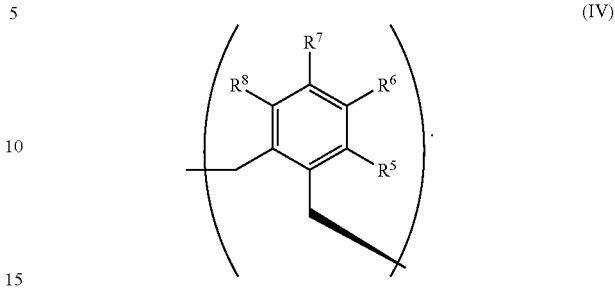

(IV)

In formulas III and IV, each of $R^5$, $R^6$, $R^7$, $R^8$, and $R^9$, independently, can be a substituent selected from the group consisting of —H, —OH, —$OCH_3$, —$CO(C_6H_5)$, —Br, —I, —F, —Cl, —$CH_3$, and —$CH_2CH_3$.

$R^4$ can be an isoleucine side chain or a valine side chain.

X can be —O— or —(NH)—.

Y can be —H or a hydroxyl protecting group. Examples of hydroxyl protecting groups which can be present at Y include an alkyl-substituted silyl moiety, an aryl-substituted silyl moiety, or a silane substituted with both alkyl- and aryl-moieties. An example of a useful hydroxyl protecting group is a triisopropylsilyl moiety. Other hydroxyl protecting groups which can be used at Y in formula I are described in references such as Green and Wutz (1999, Protecting Groups in Organic Synthesis, Wiley, New York).

$R^{10}$ can be an amino acid side chain such as a leucine side chain or a lysine side chain. Alternatively, $R^{10}$ can be an amino acid or other chemical moiety which is bound with (e.g. covalently attached to) a support (e.g. a solid support). An example of a support with a didemnin analog having the structure of formula I bound therewith is depicted in FIG. 5B.

Another group of compositions included within the invention are those which comprise a didemnin analog having the structure of formula II

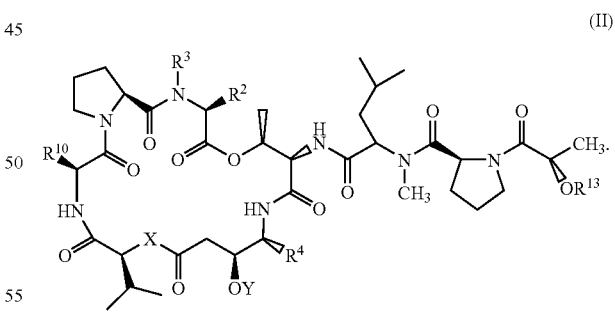

(II)

Each of $R^2$, $R^3$, $R^4$, $R^{10}$, X, and Y has the same meaning in formula II that it has in formula I.

In formula II, $R^{13}$ can be hydrogen or a chemical moiety which can be enzymatically cleavable (i.e. an enzyme-cleavable moiety). As used herein, an enzyme-cleavable moiety can include any chemical moiety which can be cleaved (i.e. chemically detached from) in the presence of a specific enzyme. Examples of enzymes capable of chemically detaching an enzyme-cleavable moiety include carboxypeptidases, beta-lactamase, beta-galactosidase, penicillin V-amidase, cytosine deaminase, nitroreductase, alkaline phosphatase, beta-glucuronidase, and catalytic antibodies. Examples of enzyme-cleavable moieties which can be incorporated in a compound described herein include cephalosporins, beta-glucosides, phosphate, pyrophosphate, beta-D-galactosides, nitrobenzamidine, cytosine, carbamates, peptides, and amino acids. Alternatively, $R^{13}$ can be an enzyme-cleavable moiety such as a di-peptide linked with glutamine-pyroglutamate, or a moiety having the structure of formula V or formula VI

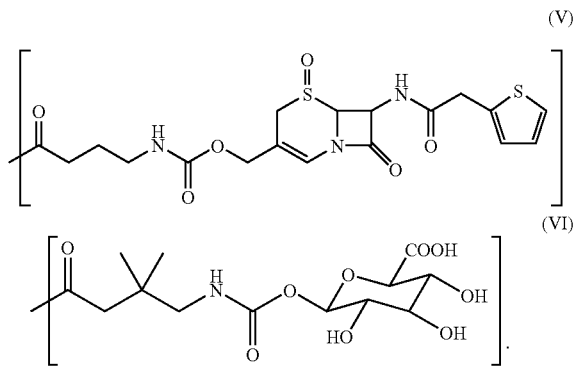

By way of illustration, in compound 131, depicted in FIG. 23, $R^{13}$ is an enzyme-cleavable moiety having the structure of formula V (i.e. a cephalosporin moiety). The cephalosporin moiety of compound 131 can be cleaved by contact with the enzyme, beta-lactamase, to generate compound 101. An $R^{13}$ substituent having the structure of formula VI can, for example, be in the form of a sodium or potassium salt.

After cleavage of an enzyme-cleavable moiety by an enzyme, the resulting didemnin analog can exhibit one or more of the physiological activities described herein. A didemnin analog having the structure of formula II, wherein $R^{13}$ is an enzyme-cleavable moiety, can, optionally, exhibit these activities before the cleavage of the enzyme-cleavable moiety. However, in a preferred embodiment, the analog exhibits therapeutic activity only following cleavage of the enzyme-cleavable moiety therefrom.

As described above, a didemnin analog having the structure of formula I or formula II can be bound with a support. The identity of the support is not critical. The support can be substantially any material with which such an analog can be bound (e.g. by covalent attachment through one of the $R^{10}$ or $R^1$ moieties). Examples of support materials include bonded silicates, cross-linked agarose, polyacrylamide, dextran, and allyl dextran. Such support materials can be chemically modified using reactive chemical moieties in order to facilitate covalent attachment of the analog with the support. Chemical modifications of this type are known in the art, and can, for example, include modification of a support with cyanogen bromide groups, epoxide groups, tresyl groups, and carboxyhexyl groups. Protocols for preparation of a support and subsequent attachment of a compound to the support are available in the art, and can be modified by one skilled in the art for use with a didemnin analog described herein.

Examples of didemnin analogs having the structure of formula I or formula II, include, compound 21, and compounds 101–143, some of which are depicted in one or more of FIGS. 1–39.

In compound 21, $R^1$ is -(tert-butyloxycarbonyl), $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is -(triisopropylsilyl).

In tamandarin A ({(2S)Hiv$^2$}didemnin B; compound 101), $R^1$ is —(N-methyl-R-leucine)-proline-lactate, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is —H.

In tamandarin M ({(2S)Hiv$^2$}didemnin M; compound 103), $R^1$ is —(N-methyl-R-leucine)-proline-lactate-glutamine-pyroglutamate, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucin side chain, $R^{10}$ is a leucine side chain, X is —O—, and Y is —H.

In tamandarin B ({(2S)Hiv$^2$, Norsta$^1$}didemnin B; compound 105), $R^1$ is —(N-methyl-R-leucine)-proline-lactate, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is a valine side chain, $R^{10}$ is a leucine side chain, X is —O—, and Y is —H.

In compound 107, $R^1$ is —(N-methyl-R-leucine)-glycine-(7-dimethylcoumarin-4-acetate), $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is —H.

In compound 109, $R^1$ is —(N-methyl-R-leucine)-proline-lactate-rhodamine, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is —H.

In compound 111, $R^1$ is —(N-methyl-R-leucine)-proline-lactate, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a lysine side chain, X is —O—, and Y is —H.

In compound 113, $R^1$ is —(N-methyl-R-leucine), $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is —H.

In compound 115, $R^1$ is —(N-methyl-R-leucine)-proline-lactate, $R^2$ is a lysine side chain, $R^3$ is —CH$_3$, $R^4$ is an isoleucine side chain, $R^{10}$ is a leucine side chain, X is —O—, and Y is —H.

In compound 123, $R^1$ is —(N-methyl-R-leucine)-proline-lactate, $R^2$ and $R^3$ together are a tetrahydroisoquinoline substituent having the structure of formula IV, $R^5$, $R^6$, and $R^8$ are each —H, $R^7$ is —OCH$_3$, $R^4$ is a valine side chain, $R^{10}$ is a leucine side chain, X is —O—, and Y is —H.

In compound 124, $R^1$ is —(N-methyl-R-leucine)-proline-lactate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, X is —(NH)—, and Y is —H.

In compound 128, $R^1$ is —(N-methyl-R-leucine)-proline-lactate-glutamine-cyclopentanoate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, X is —O—, and Y is —H.

In compound 129, $R^1$ is —(N-methyl-R-leucine)-proline-(N-methyl-S-alanine)-leucine-pyroglutamate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, X is —O—, and Y is —H.

In compound 131, $R^1$ is —(N-methyl-R-leucine)-proline-lactate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, $R^{13}$ is a cephalosporin moiety cleavable by the enzyme, beta-lactamase, X is —O—, and Y is —H.

In compound 132, $R^1$ is —(N-methyl-R-leucine)-(S)proline-(S)lactate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, $R^{13}$ is a beta-glucoside moiety cleavable by the enzyme, beta-glucuronidase, X is —O—, and Y is —H.

In compound 134, $R^1$ is —(N-methyl-S-leucine)-(S)proline-pyruvate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, X is —O—, and Y is —H.

In compound 137, $R^1$ is —(N-methyl-R-leucine)-(S)proline-pyruvate, $R^2$ and $R^3$ together are a tetrahydroisoquinoline substituent having the structure of formula IV, $R^5$, $R^6$, and $R^8$ are each —H, $R^4$ is an isoleucine side chain, $R^{10}$ is a leucine side chain, X is —O—, and Y is —H.

In compound 138, $R^1$ is —(N-methyl-R-leucine)-(S)proline-pyruvate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a lysine side chain, covalently attached to a support, X is —O—, and Y is —H.

In compound 142, $R^1$ is —(N-methyl-S-leucine)-(S)proline-pyruvate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is a valine side chain, $R^{10}$ is a leucine side chain, X is —O—, and Y is —H.

In compound 143, $R^1$ is —(N-methyl-R-leucine)-(S)-proline-pyruvate, $R^2$ is an O-methyl-tyrosine side chain (i.e. $R^5$, $R^6$, $R^8$, and $R^9$ are each —H and $R^7$ is —OCH$_3$), $R^3$ is —CH$_3$, $R^4$ is an isoleucine side chain, $R^{10}$ is a leucine side chain, X is —NH—, and Y is —H.

The structural similarity of didemnin B and tamandarin A (i.e. {(2S)Hiv$^2$}didemnin B; compound 101), is illustrated in FIG. 25. The primary structural difference, indicated by brackets and dotted lines, is in the macrocycle portion of these compounds. Tamandarin A, shown in FIG. 25A, contains an alpha-hydroxyisovaleryl (Hiv) moiety, and didemnin B, shown in FIG. 25B, contains an alpha-(alpha-hydroxyisovaleryl)-propionyl (Hip) moiety. The simpler macrocycle structure of tamandarin A, and of any compound having the structure of formula I or formula II, can be synthesized more readily than the macrocyclic structure of didemnin B. Compounds which have the structure of either of formula I and formula II can be more easily (and generally more inexpensively) prepared than compounds which are identical but for the presence of an Hip moiety in place of the Hiv moiety.

Another group of compounds that can exhibit the physiological activities described herein and which are included in the invention are compounds which correspond to fragments of didemnin analogs having the structure of formula I or formula II. Fragments which exhibit this activity have the structure of formula VII

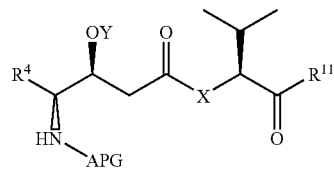

(VII)

In formula VII, X, Y, and $R^4$ have the identities described for formulas I and II, and APG is an amine protecting group. Examples of amine protecting groups which can be present in the active fragments include carbobenzyloxy (CBZ) and a tert-butyloxycarbonyl (BOC) moieties. Other useful amine protecting groups are described in references such as Green and Wutz (1999, Protecting Groups in Organic Synthesis, Wiley, New York) and Bodansky (1993, Principles of Peptide Synthesis, Springer, Berlin).

$R^{11}$ in formula VII can be any of —OH, —NH$_2$, —(O-allyl), and —(O-pentafluorophenyl). Alternatively $R^{11}$ can be a substituent having the structure shown in formula VIII

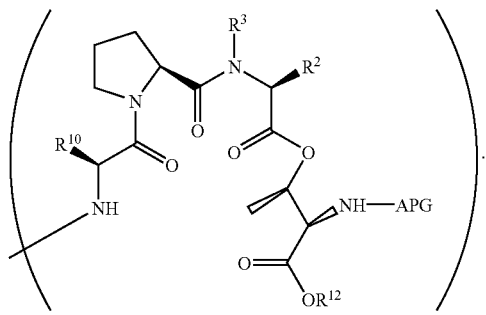

(VIII)

In formula VIII, $R^2$, $R^3$, and $R^{10}$ have the identities described for formulas I and II, and APG is an amine protecting group as described for formula VII (although it need not be the same APG as in formula VII). $R^{12}$ can be either —H or a hydroxyl protecting group, as described herein. Compounds having the structure of formula VII that can be made and used as described herein, and include the compounds designated 6, 17, 19, and 20 in FIG. 26.

Methods of Using Compounds Described Herein

Didemnin analogs and physiologically active fragments thereof, as disclosed herein, such as compounds having the structure of one of formulas I, II, and VII, can be used to affect a variety of physiological processes. Each of these types of compounds can be used to inhibit protein synthesis. Furthermore, the compounds can be used to inhibit progression of a cell through the cell cycle. While not being bound by any particular theory of operation, it is believed that the cell cycle-inhibiting activity of the compounds can be attributed to inhibition of protein synthesis and possibly also to inhibition of other cellular activities associated with DNA replication or cell division. Didemnin analogs and their active fragments also induce apoptosis in cells. The physiological activities attributable to didemnin analogs and fragments make these compounds useful for alleviating a variety of disorders in which one or more of cell growth, proliferation, and survival are aberrant. Examples of such disorders include cancers at various stages (e.g. tumorigenesis, tumor growth, and metastasis) and viral infections at various stages (e.g. infection of cells with virus particles, production of virus particles within a cell, and survival of virus-infected cells).

While still not being bound by any particular theory of operation, it is believed that the physiological activities attributable to the didemnin analogs and fragments described herein result from one or more interactions between such analogs or fragments and at least one cellular component. This interaction(s) leads, directly or indirectly, to the observed cellular response. Accordingly, the invention encompasses use of compounds having the structure of one of formulas I, II, and VII to identify one or more cellular components which contributes to a disorder phenotype in an individual. Identification of such a cellular component can indicate an effective course of treatment for alleviating the disorder. Examples of compounds useful for this purpose include didemnin analogs and fragments which have the structure of one of formulas I, II, and VII and which comprise a fluorescent substituent (e.g. at $R^1$ or $R^2$), photoreactive chemical moiety, such as a moiety having the structure

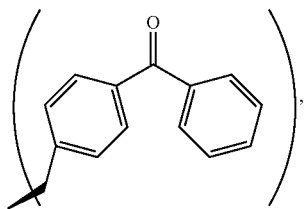

or a moiety bound with a support.

Fluorescent and other detectably labeled didemnin analogs described herein (as well as their physiologically active fragments) can be used to identify cells in which those analogs and fragments can exert their physiological effects. For example, cells which absorb or bind with a fluorescent compound having the structure of one of formula I, II, and VII can be identified or isolated. Identification or isolation of such cells can be used to diagnose a disorder associated with the presence of such cells. Identification or isolation of these cells can also indicate which of the didemnin analogs and fragments are efficacious for treating a disorder involving the cells.

The didemnin analogs and fragments described herein (i.e. those having the structure of one of formulas I, II, and VII) can be used for anti-proliferative, anti-tumor, anti-viral, and immunosuppressive purposes. For example, these compounds can be used in a pharmaceutical preparation or medicament to be administered to a patient afflicted with a disorder in which one or more of protein synthesis, cell growth, proliferation, and survival are aberrant. Such medicaments can be used to treat disorders such as cancers (e.g. breast cancer), viral, fungal, parasitic, and bacterial infections, auto-immune disorders, allergies, other hyper-immune disorders, and atherosclerosis.

Examples of anti-tumor activities that can be exhibited by the compounds described herein include inhibition of tumorigenesis, inhibition of metastasis, inhibition of tumor cell growth, inhibition of tumor cell proliferation, and enhancement of tumor cell apoptosis. Dehydrodidemnin exhibits activity against cell lines derived from several human solid tumor types, including non-small cell lung cancer and colon tumor cell lines, and exhibits selective anti-tumor activity against non-small cell lung cancer, melanomas, ovarian cancer, and colorectal cancer (Depenbrock et al., 1998, Brit. J. of Cancer 78(6): 739–744). The didemnin analogs and fragments described herein exhibit anti-tumor activities in cells of one or more of these lines, as well as in cells of the corresponding tumor type in vivo. Determination of the effectiveness of any particular didemnin analog or fragment described herein against any particular tumor type can be made using standard methods involving, for example, one or more of the 60 standard tumor cell lines maintained in the U.S. National Cancer Institute drug screening program.

Examples of anti-viral activities that can be exhibited by the didemnin analogs and fragments described herein include inhibition of binding of a virus with a cellular target, inhibition of infection of a cell by a virus, inhibition of cellular synthesis of virus components, inhibition of intracellular assembly of virus particles, inhibition of release of virus particles from an infected cell, inhibition of growth of a cell infected by a virus, inhibition of proliferation of a cell infected by a virus, and induction of death (i.e. apoptosis) of a cell infected by a virus. The anti-viral activity of the compounds described herein can, for example, be used to treat or prevent viral infections of mammals and associated symptoms. By way of illustration, a didemnin analog or fragment described herein can be used to treat or prevent infections by viruses such as Rift Valley Fever virus, Dengue virus, or any of the equine encephalitis viruses.

Examples of immunosuppressive activities that can be exhibited by the didemnin analogs and fragments described herein include inhibition of a cellular immune response to an immunogen (e.g. an infectious agent, or a transplanted cell or tissue) and inhibition of a humoral immune response to an immunogen. Examples of disorders in which immunosupression can be desirable include autoimmune disorders, transplant rejection disorders (e.g. rejection of a solid tissue or bone marrow transplant), development of an immune response to an implanted device (e.g. a stent or a heart valve), immune hypersensitivity, and anaphylaxis.

The didemnin analogs and fragments described herein can be administered in vitro to a cell or tissue (e.g. a cultured cell or tissue, or a cell or tissue harvested from one animal prior to introduction into the same or a different animal). Alternatively, the agents can be administered to the cell or tissue in vivo by administering the agent or a pharmaceutical composition comprising the agent to an animal (e.g. a mammal such as a human) that comprises the cell or tissue.

In one embodiment of the treatment methods described herein, a didemnin analog described herein and having an enzyme-cleavable group attached thereto (e.g. a compound having the structure of formula II) is administered to an animal. Upon cleavage of the enzyme-cleavable group, the compound is transformed from an inactive (or less active) form to an active (or more active) form, as shown in FIGS. 23 and 24. Thus, the didemnin analog can be selectively activated at a body location at which the enzyme activity occurs.

The enzyme which is used to cleave a didemnin analog having an enzyme-cleavable moiety attached can be an enzyme which naturally occurs at a body location in an animal. Alternatively, the enzyme can be provided to the animal, for example as a composition comprising the enzyme or a nucleic acid which encodes the enzyme. As another example, the enzyme can be coupled (e.g. covalently, using a cross-linking agent or by expression as an enzyme-antibody fusion protein) with an antibody that specifically binds with a tissue (e.g. cancerous cells such as leukemic cells or cells of a solid tumor) at a body location in the animal, and the antibody-enzyme complex can be administered to an animal. Administration of a didemnin analog having an attached enzyme-cleavable group to the same animal results in preferential activation of the compound at the tissue or body location. The physiological effect of the compound can thereby be localized at the tissue or body location, and any side effect attributable to the activated compound can thereby be reduced or minimized.

A support-bound didemnin analog (or a support-bound fragment of a didemnin analog which exhibits a corresponding physiological activity; e.g. a fragment having a structure according to formula VII) can be used to identify cells which comprise, on their surfaces or elsewhere, receptor proteins, glycoproteins, and the like, which are capable of interacting or binding with the analog. As an example, a didemnin analog having the structure of formula I and attached to a support can, by virtue of its interaction with a particular cellular receptor, be used to identify or physically isolate cells of a particular type (e.g. tumor cells) which are characterized by the presence of the particular receptor.

Methods of Making Compounds Described Herein

The present invention include methods of making didemnin analogs and fragments described herein. Preferably, the method that is used results in the stereoselective synthesis of a compound described herein. For example, synthesis of (−) tamandarin A ({(2S)Hiv²}didemnin B; compound 101) is exemplified herein at Example 1.

In reference to methods of making the analogs and fragments described herein, the substituents $R^2$, $R^3$, $R^4$, $R^5$, $R^6$, $R^7$, $R^8$, $R^9$, $R^{10}$, X, and Y, have the same meanings as used above.

As used in the present disclosure, a protection reaction can include any reaction whereby one or more chemical moieties are covalently (but reversibly) attached to one of a nitrogen atom, an oxygen atom, and a sulfur atom of a molecule. Such attachment prevents the atom or atoms from participating in non-desired chemical reactions, i.e. becoming covalently attached to other chemical moieties, and donating or accepting either of protons and electrons to other chemical moieties. A chemical moiety thus attached is referred to as "a protecting group." By way of example, the nitrogen atom of a compound having the structure of formula IX, such as D-allo-isoleucine, can be protected using a reagent such as carbobenzyloxy-succinimide(CBZ-succinimide). Use of this reagent in a standard protocol yields a protected D-allo-isoleucine, i.e. $N^{(alpha)}$-CBZ-D-allo-isoleucine, having the structure of compound 8 in FIG. 26A. In compound 8, the CBZ moiety acts as an amine protecting group, and the nitrogen atom to which it is attached cannot readily undergo additional chemical reactions. Further by way of example, when X is —(NH)—, a protected amine group (e.g. —N(CBZ)—) can be used in the reactions described herein. As an alternative example, the hydroxyl moiety of compound 11 in FIG. 26A, can be protected using a reagent such as triisopropylsilyltriflate (TIPSOTf) to yield compound 12 in FIG. 26A. In this compound, Y is a triisopropylsilyl (TIPS) moiety and acts as a hydroxyl protecting group, preventing chemical reactions with the oxygen atom to which this moiety is attached.

Protocols for performing protection reactions and comprehensive information about chemical moieties can be used as protecting groups is found in references such as Green and Wutz (1999, Protecting Groups in Organic Synthesis, Wiley, New York) or Bodansky (1993, Principles of Peptide Synthesis, Springer, Berlin).

Didemnin analogs and fragments can be made by converting a compound having the structure of formula IX

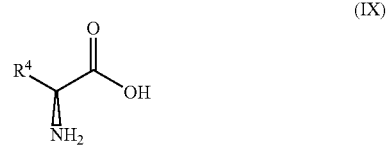

(IX)

to a compound having the structure of formula X

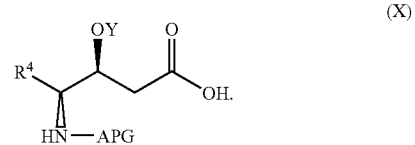

(X)

Such a series of reactions can include, but is not limited to, a protection reaction, an activation reaction, an esterification reaction, and an ester hydrolysis reaction. The amine group of formula IX is preferably protected prior to performing the esterification and hydrolysis reactions. A specific example of making a compound having the structure of formula X is given in Example 1. In formulas X–XVIII, "APG" refers to an amine protecting group such as carbobenzyloxy (CBZ) moiety or tert-butyloxycarbonyl (BOC) moiety. Alternative amine protecting groups can also be used, as described herein and in the art.

An example of an activation reaction included in the method of making a compound having the structure of formula X is depicted in FIG. 26A, reaction B. Activation of a compound such as compound 8 can involve a reagent such as pentafluorophenol (PFPOH) to yield compound 9. Compound 9 is an example of an activated intermediate that more readily undergoes subsequent reactions, such as esterification, at the carbonyl carbon of its PFP ester moiety. Esterification reactions which do not require an activated intermediate can also be employed to make a compound having the structure of formula X.

Any method of ester hydrolysis known in the art that does not comprise harsh conditions which favor racemization and can be used to make a compound having the structure of formula X. By way of example, a compound having the structure

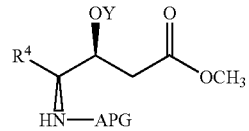

can be hydrolyzed using a strong base in a solvent mixture, as exemplified in FIG. 26A, reaction F. Reagents and conditions suitable for ester hydrolysis under milder conditions (i.e. including conditions which do not favor racemization) can be readily selected by one skilled in the art.

A compound having the structure

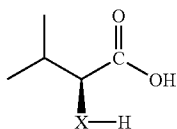

can be esterified with, for example, allyl bromide (e.g. as described in Example 1), to yield a compound having the structure of formula XI

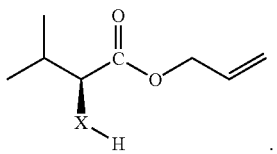
(XI)

A compound having the structure of formula IX and a compound having the structure of formula XI can be coupled (e.g. esterified) to yield a compound having the structure of formula XII

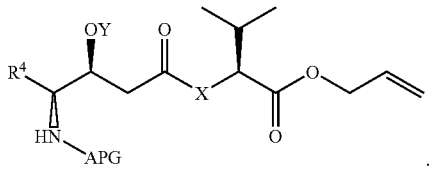
(XII)

(e.g. reaction I of FIG. 26B). Optionally, such a reaction can be performed using a catalyst, a coupling reagent, or an esterification reagent. Reagents and conditions useful for this type of reaction are known in the art and exemplified in Example 1. Didemnin fragments having the structure of formula XII exhibit one or more of the pharmacological activities described herein.

A compound having the structure of formula XII can be hydrolyzed to yield a compound having the structure of formula XIII

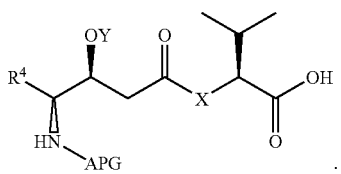
(XIII)

As described elsewhere herein, reaction conditions and reagents suitable for ester hydrolysis are known in the art, and can be readily applied by a skilled artisan. An example of this type of hydrolysis is depicted in FIG. 26B, reaction J. Didemnin fragments having the structure of formula XIII exhibit one or more of the pharmacological activities described herein.

The carboxyl group of a compound having the structure of formula XIII can be activated to yield a compound having the structure of formula XIV

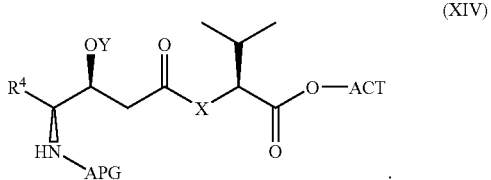
(XIV)

In formula XIV, "ACT" refers to an activating group, such as a pentafluorophenyl (PFP) moiety. Another example of an activating group is an N-hydroxysuccinimide moiety. Chemical activation can be performed using reagents such as an activating reagent, a catalyst, an activating group donor, or the like. By way of example, compound 6, depicted in FIG. 26C, is activated by covalent attachment of a PFP group to yield compound 19. Protocols for activating a compound in the manner disclosed herein are known in the art. Didemnin fragments having the structure of formula XIV exhibit one or more of the pharmacological activities described herein.

The activated compound having the structure of formula XIV can be coupled with a third reactant having the structure of formula XV

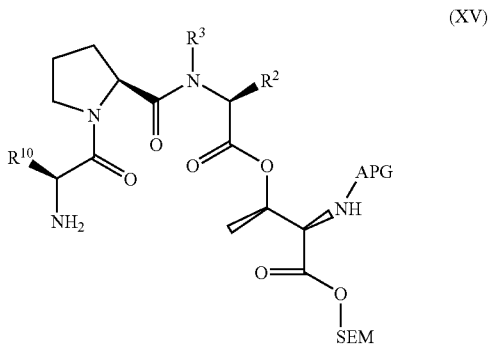
(XV)

to yield a compound having the structure of formula XVI

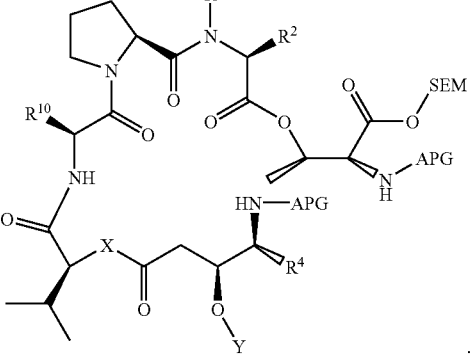
(XIV)

In formulas XV and XVI, SEM refers to 2-(trimethylsilyl) ethoxycarbonyl. An example of this reaction is depicted in reaction M of FIG. 26C, in which compound 19 is coupled with compound 18 to yield compound 20. The reagents and conditions necessary for preparation of a protected peptide such as compound 18 are described, for example, in Li et al.

(1990, J. Am. Chem. Soc. 112: 7659–7672). Didemnin analogs having the structure of formula XVI exhibit one or more of the pharmacological activities described herein.

A didemnin analog having one or more of the pharmacological activities described herein can be made by removing one of the amino protecting groups and the carbonyl hydroxyl protecting group of a compound having the structure of formula XVI and cyclizing the compound to yield a PSI having the structure of formula XVII

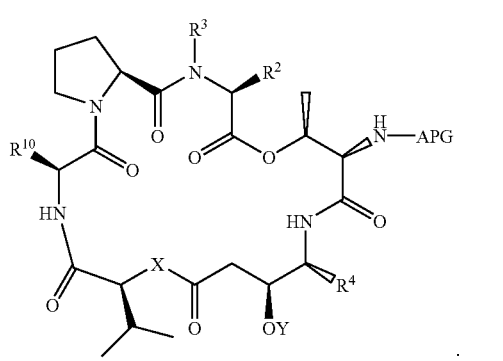

(XVII)

An example of reactions of this type is shown in step N of FIG. 26D. Chemically de-protecting a compound such as one having the structure of formula XVI can be accomplished by reacting the compound with one or more reagents to remove a protecting group of the compound. Exemplary de-protection reactions are disclosed herein, for example for compound 20, as shown in FIG. 26D. Other protocols for de-protecting a compound are known in the art, and can be readily applied by a skilled artisan to de-protection of a compound having the structure of formula XVI. Cyclization of a de-protected compound otherwise having the structure of the formula XVI can be accomplished using any method known in the art for macrocyclization of peptides. For example, the macrocyclization conditions can be similar or identical to those used in the cyclization that yields compound 21, depicted in FIG. 26D and described in Example 1. Didemnin analogs having the structure of formula XVII exhibit one or more of the therapeutic activities described herein.

One or more of the protecting groups of a compound having the structure of the formula XVII can be removed to yield a compound having the structure of formula XVIII

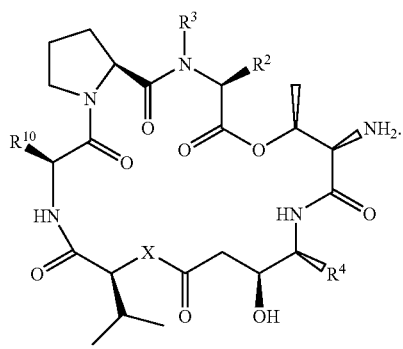

(XVIII)

This type of de-protection is exemplified in reaction O of FIG. 26E. Didemnin analogs having the structure of formula XVIII exhibit one or more of the therapeutic activities described herein.

Yet another active compound can be made by coupling a compound having the structure of formula XVIII and a reagent having the structure of formula XIX

(XIX)

to yield a PSI having the structure of formula XX

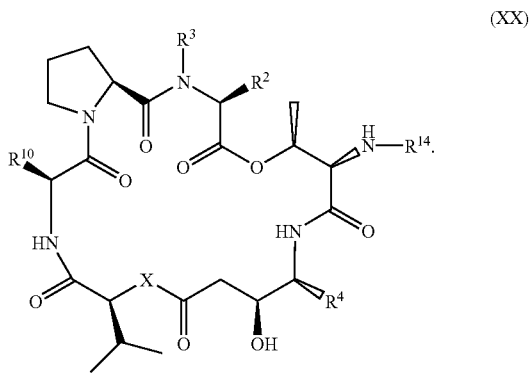

(XX)

This reaction is exemplified in reaction N of FIG. 26E. $R^{14}$ can, for example, be any of the moieties described above as $R^1$. The $R^{14}$ substituent group can comprise an enzyme cleavable moiety, preferably at or near the distal end thereof (relative to the macrocycle). Such a moiety can be cleavable by an enzyme, for example, a carboxypeptidase, a beta-lactamase, a beta-galactosidase, a penicillin V-amidase, a cytosine deaminase, a nitroreductase, a alkaline phosphatase, a beta-glucuronidase, and a catalytic antibody. An example of an $R^{14}$ moiety which comprises an enzyme-cleavable moiety is —(N-methyl)leucine-(S)proline-(S)lactate-(S)glutamine-(S)pyroglutamate. Other examples of enzyme-cleavable moieties are described herein. By way of illustration, compounds 131 and 132, depicted in FIGS. 23 and 24, respectively, can be prepared using the methods described herein. Didemnin analogs and fragments which have an enzyme cleavable moiety attached thereto and which otherwise have the structure of one of formulas XII–XVIII upon cleavage of the enzyme-cleavable group therefrom exhibit one or more of the therapeutic activities described herein.

Variation of the substituents of the didemnin analogs and fragments can require slight modifications in the general methods described herein. It is understood that the invention includes such modifications, as they could be readily designed by one of ordinary skill in the art of synthetic chemistry.

Pharmaceutical Compositions

The invention encompasses pharmaceutical compositions comprising at least one of the didemnin analogs and the physiologically active fragments described herein. Such compositions can comprise the analog/fragment and a pharmaceutically acceptable carrier. By way of example, a pharmaceutical composition can comprise a pharmaceutically acceptable carrier and a didemnin analog having the structure of either formula I or formula II as an active agent. As a further example, a pharmaceutical composition can comprise a pharmaceutically-acceptable carrier and one or more of the compounds depicted in the figures in this disclosure.

Such pharmaceutical compositions can be used, for example, in the methods described herein for and for inhibiting one or more of protein synthesis, cell cycle progression, tumorigenesis, growth, and proliferation in a cell. In addition, such compositions can be used in the methods described herein for enhancing apoptosis in a cell.

Pharmaceutical compositions that are useful in the methods of the invention can be administered systemically in oral solid formulations, ophthalmic, suppository, aerosol, topical or other similar formulations. In addition to the active agent, such pharmaceutical compositions can contain pharmaceutically-acceptable carriers and other ingredients known to enhance and facilitate drug administration. Other possible formulations, such as nanoparticles, liposomes, resealed erythrocytes, and immunologically based systems can also be used to administer the active agent according to the methods of the invention.

The invention encompasses pharmaceutical compositions which consist of the active agent, in a form suitable for administration to a subject, or the pharmaceutical composition can comprise the active agent and one or more pharmaceutically acceptable carriers, one or more additional ingredients, or some combination of these. The active agent can be present in the pharmaceutical composition in the form of a physiologically acceptable ester or salt, such as in combination with a physiologically acceptable cation or anion, as is well known in the art.

The formulations of the pharmaceutical compositions described herein can be prepared by any method known or hereafter developed in the art of pharmacology. In general, such preparatory methods include the step of bringing the active agent into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals including commercially relevant mammals such as cattle, pigs, horses, sheep, cats, and dogs.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active agent, and immunologically-based formulations.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active agent. The amount of the active agent is generally equal to the dosage of the active agent which would be administered to a subject or a convenient fraction of such a dosage such as, for example, one-half or one-third of such a dosage.

In addition to the active agent, a pharmaceutical composition of the invention can further comprise one or more additional pharmaceutically active agents such as, other tumor therapy agents, other anti-infective agents, and the like.

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including, but not limited to, a tablet, a hard or soft capsule, a cachet, a troche, or a lozenge, each containing a predetermined amount of the active agent. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active agent may, for example, be made by compressing or molding the active agent, optionally with one or more additional ingredients. Compressed tablets can be prepared by compressing, in a suitable device, the active agent in a free-flowing form such as a powder or granular preparation, optionally mixed with one or more of a binder, a lubricant, an excipient, a surface active agent, and a dispersing agent. Molded tablets can be made by molding, in a suitable device, a mixture of the active agent, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginate. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearate, silica, and talc.

Tablets can be non-coated or they can be coated using known methods to achieve delayed disintegration in the gastrointestinal tract of a subject, thereby providing sustained release and absorption of the active agent. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active agent can be made using a physiologically degradable composition, such as gelatin. Such hard capsules comprise the active agent, and can further comprise additional ingredients including, for example, an inert solid diluent such as calcium carbonate, calcium phosphate, or kaolin.

Soft gelatin capsules comprising the active agent can be made using a physiologically degradable composition, such as gelatin. Such soft capsules comprise the active agent, which can be mixed with water or an oil medium such as peanut oil, liquid paraffin, or olive oil.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active agent in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxy-cetanol, polyoxyethylene sorbitol monooleate, and polyoxyethylene sorbitan mono-oleate, respectively). Known emulsifying agents include, but are not limited to, lecithin and acacia. Known preservatives include, but are not limited to, methyl, ethyl, or n-propyl-para-hydroxybenzoates, ascorbate, and sorbate. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active agent in aqueous or oily solvents can be prepared in substantially the same manner as liquid suspensions, the primary difference being that the active agent is dissolved, rather than suspended in the solvent. Liquid solutions of the pharmaceutical composition of the invention can comprise each of the components described with regard to liquid suspensions, it being understood that suspending agents will not necessarily aid dissolution of the active agent in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition of the invention can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the invention can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active agent with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

Retention enema preparations or solutions for rectal or colonic irrigation can be made by combining the active agent with a pharmaceutically acceptable liquid carrier. As is well known in the art, enema preparations can be administered using, and can be packaged within, a delivery device adapted to the rectal anatomy of the subject. Enema preparations can further comprise various additional ingredients including, but not limited to, antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation can be made by combining the active agent with a pharmaceutically acceptable liquid carrier. As is well known in the art, douche preparations can be administered using, and can be packaged within, a delivery device adapted to the vaginal anatomy of the subject. Douche preparations can further comprise various additional ingredients including, but not limited to, antioxidants, antibiotics, anti-fungal agents, and preservatives.

Formulations of a pharmaceutical composition suitable for parenteral administration can comprise the active agent combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In one embodiment of a formulation for parenteral administration, the active agent is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active agent, additional ingredients such as the dispersing agents, wetting agents, or suspending agents described herein. Such sterile injectable formulations can be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active agent in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active agent, although the concentration of the active agent can be as high as the solubility limit of the active agent in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active agent and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active agent dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active agent can constitute 0.1 to 20% (w/w) of the composition. The propellant can further comprise additional ingredients such as a liquid non-ionic or solid anionic surfactant or a solid diluent (preferably having a particle size of the same order as particles comprising the active agent).

Pharmaceutical compositions of the invention formulated for pulmonary delivery can also provide the active agent in the form of droplets of a solution or suspension. Such formulations can be prepared, packaged, or sold as aqueous or dilute alcoholic solutions or suspensions, optionally sterile, comprising the active agent, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active agent and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active agent, and can further comprise one or more of the additional ingredients described herein.

A pharmaceutical composition of the invention can be prepared, packaged, or sold in a formulation suitable for buccal administration. Such formulations may, for example, be in the form of tablets or lozenges made using conventional methods, and may, for example, 0.1 to 20% (w/w) active agent, the balance comprising an orally dissolvable or degradable composition and, optionally, one or more of the additional ingredients described herein. Alternately, formulations suitable for buccal administration can comprise a powder or an aerosolized or atomized solution or suspension comprising the active agent. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition of the invention can be prepared, packaged, or sold in a formulation suitable for ophthalmic administration. Such formulations may, for example, be in the form of eye drops including, for example, a 0.1–1.0% (w/w) solution or suspension of the active agent in an aqueous or oily liquid carrier. Such drops can further comprise buffering agents, salts, or one or more other of the additional ingredients described herein. Other ophthalmically-administrable formulations which are useful include those which comprise the active agent in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; anti-fungal agents; stabilizing agents; and pharmaceutically acceptable polymeric or hydrophobic materials. Other "additional ingredients" which can be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The relative amounts of the active agent, the pharmaceutically acceptable carrier, and any additional ingredients in a pharmaceutical composition of the invention will vary, depending upon the identity, size, and the type and severity of condition of the subject treated and further depending upon the route by which the composition is to be administered. By way of example, the composition can comprise between 0.1% and 100% (w/w) active agent.

Typically dosages of the active agent which can be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the active agent will vary from about 1 milligram to about 10 g per kilogram of body weight of the animal. More preferably, the dosage will vary from about 10 milligram to about 1 gram per kilogram of body weight of the animal. Alternatively, the dosage can be determined in units of square meters of the body surface of an animal (i.e. milligrams or kilograms per square meter, mg/m$^2$ or kg/m$^2$). Preferably, this dosage will vary from about 0.1 milligram to about 5 grams per square meter of body surface of the animal. More preferably, the dosage will vary from about 1 milligram to about 1 gram per square meter of body surface of the animal.

The active agent can be administered to an animal as frequently as several times daily, or it can be administered less frequently, such as once a day, once a week, once every two weeks, once a month, or even lees frequently, such as once every several months or even once a year or less. The frequency of the dose is determinable by the skilled artisan and depends upon various factors including, but not limited to, the type and severity of the disease being treated, the type and age of the animal, etc.

The invention is now described with reference to the following Examples. These Examples are provided for the purpose of illustration only and the invention is not limited to these Examples, but rather encompasses all variations which are evident as a result of the teaching provided herein.

EXAMPLES

The reagents and procedures which were used in Examples 1–5 are now presented.

Unless otherwise stated, all reactions were conducted in the presence of an inert atmosphere (e.g. argon or nitrogen). All solvents were reagent grade (e.g. distilled solvents, chromatography solvents, and reaction work-up solvents) or HPLC grade (i.e. reaction solvents). Anhydrous diethyl ether and tetrahydrofuran (THF) were distilled from sodium and benzophenone. The boiling point range of the hexane used was 38–55° C. Methylene chloride ($CH_2Cl_2$), benzene, toluene, and N,N-dimethyl formamide (DMF) were distilled from calcium hydride ($CaH_2$). Organic acids and bases were reagent grade. Triethylamine ($Et_3N$), diisopropylethylamine (DIPEA), morpholine, and N-methylmorpholine (NMM) were distilled from calcium hydride ($CaH_2$). All other reagents, including dimethylaminophenol and diethyl 1,3-acetonedicarboxylate, were the highest purity commercial available. Analytical thin-layer chromatography (TLC) was performed using EM Separations Tech./Merck silica gel (60-F254) plates (0.25 millimeter) pre-coated with a fluorescent indicator. Visualization was effected using ultraviolet light (254 nanometers), phosphomolybdic acid (7% w/v) in 95% ethanol. Melting points (mp) were determined using a Thomas-Hoover capillary melting point apparatus and are reported without correction. Proton and carbon magnetic resonance spectra ($^1$H- and $^{13}$C-NMR, respectively) were recorded on a Bruker AM-500 (500 MHz) Fourier transform spectrometer, and chemical shifts were expressed in parts per million (ppm) relative to $CHCl_3$ as an internal reference (7.24 ppm for $^1$H and 77.0 for $^{13}$C). Multiplicities are designated as singlet (s), doublet (d), doublet of doublets (dd), doublet of triplets (dt), triplet (t), quartet (q) multiplet (m), and broad singlet (s). Infrared spectra (IR) were obtained using a Perkin-Elmer Model 1600 FT-IR spectrophotometer. Absorptions are reported in wave number (cm$^-$$_1$). Optical rotations (in degrees) were measured using a Perkin-Elmer Model 341 polarimeter. High resolution mass spectra (HRMS) were obtained using either a VG 70–70HS, or a Micromass AutoSpect. Elemental Analyses were performed using a Perkin-Elmer 2400 Series II CHNS/O Analyzer. Flash column chromatography was performed using Merck silica gel 60 (240–400 mesh) using the solvent systems indicated for individual experiments.

Example 1

Total Synthesis of (−) Tamandarin A

A method of synthesizing (−) Tamandarin A is described in this example. The method is illustrated in FIG. 26. The method is initiated with the synthesis of compound 13, depicted in FIG. 26A.

Reaction A of FIG. 26A: Synthesis of Compound 8

A solution comprising 5.13 milliliters (36.9 millimoles) of $Et_3N$ was added drop-wise to a solution comprising 1.56 grams (11.9 millimoles) of compound 7, D-allo-isoleucine, and 50 milliliters of freshly distilled $CH_2Cl_2$ at 0° C. To the resulting mixture was added 3.114 grams (12.5 millimoles) of carbobenzyloxy succinimide (Cbz-succinimide). This reaction was stirred at 0° C. for 1 hour, and maintained with stirring at room temperature overnight. The reaction mixture was concentrated, diluted with 20 milliliters of a saturated solution of $NaHCO_3$, and washed twice with 10 milliliters aliquots of ether. The combined ether layers were extracted with 10 milliliters of a saturated solution of sodium bicarbonate ($NaHCO_3$). The combined aqueous layers were cooled to 0° C., acidified to pH 2 by drop-wise addition of 1 normal $KHSO_4$, and extracted three times with 20 milliliters of ethyl acetate (EtOAc). The EtOAc layers were combined, washed with 20 milliliters of a saturated solution of NaCl, and dried in the presence of anhydrous sodium sulfate ($Na_2SO_4$). The resulting solution was filtered and concentrated under reduced pressure to yield 3.13 grams of compound 8 (99% yield). Compound 8 was obtained as a colorless oil and used directly in the next step without purification. Analytical data for compound 8 were as follows: $R_f$ 0.08 (20:80-ethyl acetate:hexane); $^1$H NMR (500 MHz, $CDCl_3$) δ0.86–0.90 (m, 3H), 0.93–0.97 (m, 3H), 1.20–1.27 (m, 1H) and 1.42–1.47 (m, 1H), 1.98–2.09 (m, 1H), 4.47–4.50 (dd, $J_1$=9.1 Hz, $J_2$3.4 Hz, 1H), 5.10 (s, 2H), 5.17–5.19 (d, J=9.1 Hz, 1H), 7.29–7.35 (m, 5H); $^{13}$C NMR (250 MHz, $CDCl_3$) δ 11.69, 14.35, 26.20, 37.42, 56.9,6, 67.20, 128.14, 128.24, 128.55, 135.06, 156.42, 177.41; IR ($CHCl_3$) 2470–3540, 3440, 2980, 2950, 2890, 1720, 1510, 1455, 1405, 1385, 1325–1355, 1230–1280, 1165, 1095, 1040, 1005, 910 $cm^{-1}$.

Reactions B and C of FIG. 26A: Synthesis of Compound 10

A solution comprising 3.534 grams (13.3 millimoles) of compound 8 (i.e. crude Cbz-D-allo-isoleucine) 50 milliliters of anhydrous $CH_2Cl_2$ was cooled in an ice bath to 0° C. Each of the following was added in solid form to the cooled solution: 2.574 grams (14.0 millimoles) pentafluorophenol (PFPOH), 3.064 grams (16.0 millimoles) of 1-ethyl-3-(3-dimethylaminopropyl)carbodiimide hydrochloride (EDAC.HCl), and 0.325 gram (2.7 millimoles) 4-dimethylaminopyridine (DMAP). The resulting mixture was maintained at 0° C. for half an hour with stirring, and at room temperature for an additional 4 hours. The mixture was diluted with 50 milliliters of $CH_2Cl_2$. The $CH_2Cl_2$ layer was washed once using 25 milliliters of a 10% solution of hydrochloric acid (HCl), once using 25 milliliters of a 5% solution of $NaHCO_3$, and once using 25 milliliters of a saturated solution of NaCl. The washed $CH_2Cl_2$ layer was dried in the presence of $Na_2SO_4$, filtered, and concentrated under reduced pressure. The resulting PFP ester, compound 9 (5.70 grams), was obtained as a colorless oil and used in the next step without purification. The following analytical data were obtained for compound 9: $R_f$ 0.52 (20:80 EtOAc:hexane); $^1$H NMR (500 MHz, $CDCl_3$) δ 0.90–1.12 (m, 6H), 1.29–1.39 (m, 1H) and 1.45–1.52 (m, 1H), 2.05–2.15 (m, 1H), 4.79–4.84 (m, 1H), 5.10 (s, 2H), 5.12–5.14 (d, J=9.1 Hz, 1H), 7.29–7.37 (m, 5H); $^{13}$C NMR (250 MHz, $CDCl_3$) δ 11.68, 14.25, 26.24 37.64, 57.09 67.45, 128.20, 128.35, 128.59, and 135.95, 136.9, 139.0, 140.0 and 142.0, 156.13, 168.87.

A solution comprising 5.70 grams of compound 9 and 25 milliliters of anhydrous THF was cooled to –78° C. An enolate solution comprising the lithium enolate of methyl acetate was prepared by cooling a solution comprising 49.2 millimoles of lithium dialdehyde and 25 milliliters anhydrous THF in a dry ice bath at –78° C., adding to the solution 3.92 milliliters (49.2 millimoles) of methyl acetate by syringe, and maintaining the resulting solution with stirring at –78° C. for 1 hour. The resulting enolate solution was added drop-wise to the solution comprising compound 9, and the resulting mixture was maintained with stirring for 0.75 hours at –78° C. The reaction was quenched at –78° C. by adding 50 milliliters of a saturated solution of aqueous ammonium chloride ($NH_4Cl$). The quenched reaction was brought to room temperature, and THF was removed under reduced pressure. The resulting aqueous solution was extracted 3 times with 25 milliliters aliquots of $CH_2Cl_2$. The combined $CH_2Cl_2$ layers were washed once using 25 milliliters of a 10% solution of hydrochloric acid (HCl), once using 25 milliliters of a 5% solution of $NaHCO_3$, and once using 25 milliliters of a saturated solution of NaCl. The washed $CH_2Cl_2$ layer was dried in the presence of $Na_2SO_4$, filtered, and concentrated under reduced pressure. This reaction yielded a yellow oil which was purified by flash column chromatography. The yellow oil was applied to a column of silica gel and eluted with a solution comprising EtOAc and hexane in a ratio of 10 to 95, respectively. The product obtained from chromatography was 3.42 grams of a colorless oil corresponding to the beta-keto ester, compound 10. The yield of compound 10 was 80%, as calculated for both Reactions B and C. The following analytical data were obtained for compound 10: $R_f$ 0.42 (35:65, EtOAc:hexane); $^1$H NMR (500 MHz, $CDCl_3$) δ 0.75–0.79 (m, 3H), 0.90–0.98 (m, 3H), 1.26–1.30 (m, 1H) and 1.42–1.46 (m, 1H), 1.97–1.99 (m, 1H), 3.53 (s, 2H), 3.72 (s, 3H), 4.56–4.58 (d, J=7.6 Hz, 1H), 5.10 (s, 2H), 5.26–5.28 (d, J=6.4 Hz, 1H), 7.30–7.36 (m, 5H); $^{13}$C NMR (250 MHz, $CDCl_3$) δ 11.83, 13.79, 26.83, 36.12, 46.56, 52.46, 63.00, 67.19, 128.10, 128.24, 128.56, 136.16, 156.42, 166.96, 201.68; IR ($CHCl_3$) 3349.1, 2964.4, 1748.3, 1712.9, 1520.6, 1454.8, 1328.2, 1232.1 $cm^{-1}$; HRMS m/z calculated for$C_{17}H_{23}NO_5Na$ ($M^+Na^+$): 344.1498, found 344.1490; $[α]D^{26}$ –27.85 (c 0.53, $CHCl_3$); Anal. Calculated for$C_{17}H_{23}NO_5$: C, 63.52; H, 7.22, N, 4.36. Found: C, 63.32; H, 7.15, N, 4.24.

Reaction D of FIG. 26A: Synthesis of Compound 11

A solution comprising 2.797 grams (8.7 millimoles) of compound 10 and 30 milliliters of HPLC-grade methanol (MeOH) was cooled to –78° C., and 1.644 grams (30.5 millimoles) of potassium borohydride ($KBH_4$) was added in portions. The resulting mixture was initially maintained with stirring at –78° C. for 10 minutes. The reaction vessel was next warmed to –20° C. and maintained with stirring for 30 minutes, following which, the reaction vessel was warmed to 0° C. and maintained with stirring for 10 minutes. The resulting mixture was quenched at 0° C. by adding a solution comprising glacial acetic acid in a drop-wise manner until the pH of the aqueous layer was not less pH 6 when tested with litmus paper. The resulting neutralized, bilayer solution was concentrated under reduced pressure, and 50 milliliters of a solution comprising EtOAc and $H_2O$ in a ratio of 1 to 1, was added. The organic layer was separated from the aqueous layer and washed with 10 milliliters of a saturated solution of NaCl. The washed organic layer was dried in the presence of $Na_2SO_4$, filtered, and concentrated under reduced pressure. The crude product thus obtained was 2.786 grams of a colorless oil comprising an 11:1 ratio of compound 11 and its stereoisomer, respectively. Crystallization of the colorless oil in a solution comprising ether and hexane afforded pure compound 11 as a white crystalline solid in 99% yield. The following analytical data were obtained for compound 11: $R_f$ 0.29 (35:65, EtOAc:hexane); $^1$H NMR (500 MHz, CDCl$_3$) δ 0.83–0.85 (m, 3H), 0.89–0.92 (m, 3H), 1.19–1.23 (m, 1H) and 1.32–1.34 (m, 1H), 1.91–1.93 (m, 1H), 2.45–2.51 (dd, J$_1$=16.7 Hz, J$_2$=9.1 Hz, 1H) and 2.58–2.62 (dd, J$_1$=16.7 Hz, J$_2$=2.7 Hz, 1H), 3.12–3.14 (d, J=4.5 Hz, 1H), 3.68 (s, 3H), 3.90–3.91 (m, 1H), 4.62–4.65 (d, J=10.0 Hz, 1H), 5.07–5.08 (d, J=5.1 Hz, 2H), 7.29–7.35 (m, 5H); $^{13}$C NMR (250 MHz, CDCl$_3$) δ 12.10, 13.64, 27.52, 34.28, 38.74, 52.25, 57.57, 67.39, 69.43, 128.50, 128.61, 128.97 and 136.82, 157.08, 174.09; IR (CHCl$_3$) 3421, 3316, 2951, 1709, 1537, 1443, 1229 cm$^{-1}$; HRMS m/z calculated for C$_{17}$H$_{25}$NO$_5$Na (M$^+$Na$^+$): 346.1630, found 346.1645; [α]D$^{20}$ −10.9 (c 0.595, CHCl$_3$); Anal. Calculated for C$_{17}$H$_{25}$NO$_5$: C, 63.12; H, 7.80, N, 4.33. Found: C, 63.23; H, 7.85, N, 4.06.

Reaction E of FIG. 26A: Synthesis of Compound 12

A solution comprising 0.8636 gram (2.67 millimoles) of compound 11 as a colorless oil and 10 milliliters of CH$_2$Cl$_2$ was placed under an argon atmosphere and cooled to 0° C. A solution comprising 0.778 milliliters (6.68 millimoles) of 2,6-lutidine was added, followed by addition of a solution comprising 1.08 milliliters (4.01 millimoles) of triisopropylsilyl triflate (i-Pr$_3$SiOTf). The reaction mixture was initially maintained with stirring at 0° C. for 30 minutes, following which, the reaction mixture was maintained at room temperature for 2 hours. The resulting mixture was diluted with 20 milliliters of CH$_2$Cl$_2$. The CH$_2$Cl$_2$ layer was washed once using 15 milliliters of a 10% solution of hydrochloric acid (HCl), once using 15 milliliters of a 5% solution of NaHCO$_3$, and once using 15 milliliters of a saturated solution of NaCl. The resulting washed CH$_2$Cl$_2$ layer was dried in the presence of anhydrous Na$_2$SO$_4$, filtered, and concentrated under pressure. The concentrated residue was purified by flash column chromatography, eluting with solutions comprising ether and hexane in a ratio of from 2 to 98, respectively, to 15 to 85, respectively. Chromatography yielded 1.204 grams (94% yield) of compound 12 as the major isomer in the form of a colorless oil. The following analytical data were obtained for compound 12: $R_f$ 0.65 (35:65, EtOAc:hexane); $^1$H NMR (500 MHz, CDCl$_3$) δ 0.84–0.91 (m, 6H), 0.99–1.05 (m, 21H), 1.12–1.34 (m, 2H), 1.81–1.84 (m, 1H), 2.54–2.62 (m, 2H), 3.54 (s, 3H), 3.73–3.75 (m, 1H), 4.34–4.36 (m, 1H), 4.69–4.71 (d, J=10.5 Hz, 1H), 5.01–5.04 (d, J=12.3 Hz, 1H) and 5.09–5.11 (d, J=12.3 Hz, 1H), 7.28–7.34 (m, 5H); $^{13}$C NMR (250 MHz, CDCl$_3$) δ 12.50, 12.74, 13.97, 18.08, 27.44, 34.40, 40.45, 51.54, 58.62, 66.67, 70.49, 128.03, 128.08, 128.46 and 136.67, 156.51, 172.00; IR (CHCl$_3$) 3450, 3359, 2944, 2863, 1728, 1510, 1459, 1434, 1384, 1308, 1232, 1171, 1090 cm$^{-1}$; HRMS m/z calculated for C$_{26}$H$_{45}$NSiO$_5$Na (M$^+$Na$^+$): 480.3145, found 480.3128; [α]D$^{20}$ +15.88 (c 0.57, CHCl$_3$); Anal. Calculated for C$_{17}$H$_{25}$NO$_5$: C, 65.09; H, 9.46, N, 2.92. Found: C, 64.80; H, 9.41, N, 2.69.

Reaction F of FIG. 26A: Synthesis of Compound 13

A solution comprising 1 normal NaOH (20 milliliters, 11 millimoles) was added to a solution comprising 0.84 gram (1.753 millimoles) of compound 12, 10 milliliters of THF, and 10 milliliters of MeOH, which was cooled to 0° C. This reaction mixture was maintained with stirring at 0° C. for 2 hours. The reaction mixture was then maintained with stirring at room temperature overnight. The reaction mixture was concentrated under reduced pressure and diluted with 10 milliliters of H$_2$O. The resulting mixture was cooled to 0° C. in an ice bath, acidified to pH 2 by adding a solution comprising 1 normal KHSO$_4$, and extracted 3 times with 10 milliliters aliquots of EtOAc. The EtOAc layers were combined, washed with 10 milliliters of a saturated solution of NaCl, dried in the presence of anhydrous Na$_2$SO$_4$, filtered, and concentrated. This reaction yielded 0.7709 gram (95% yield) of compound 13 in the form of a white foam. Compound 13 was used in the subsequent reaction without purification. Analytical data for compound 13 were as follows: $R_f$ 0.08 (35:65-ethyl acetate:hexane); $^1$H NMR (500 MHz, CDCl$_3$) δ 0.86–1.00 (m, 6H), 1.06–1.08 (m, 21H), 1.19–1.24 (m, 1H) and 1.64–1.72 (m, 1H), 1.85–1.92 (m, 1H), 2.50–2.80 (m, 2H), 3.60–3.80 (m, 1H), 4.28–4.33 (m, 1H), 4.86–4.88 (d, J=10.4 Hz, 1H), 5.06–5.22 (m, 2H), 7.29–7.45 (m, 5H).

Reaction G of FIG. 26B: Synthesis of Compound 15

Synthesis of a protected form of (2S)-α-hydroxyisovaleryl-isostatine (6) is depicted in FIG. 26B. In reaction G of FIG. 26B, L-valine (14), was dissolved in a solution comprising sodium nitrite (NaNO$_2$) and 1 normal sulfuric acid (H$_2$SO$_4$). The reaction was carried out using a standard method as described, for example, in Green and Wutz (1999, Protecting Groups in Organic Synthesis, Wiley, New York) or Bodansky (1993, Principles of Peptide Synthesis; Springer, Berlin). This reaction yielded alpha-hydroxy valine (15).

Reaction H of FIG. 26B: Synthesis of Compound 16

In reaction H, 2.46 grams (17.78 millimoles) of anhydrous potassium carbonate (K$_2$CO$_3$), and 1.25 grams (3.4 millimoles) of tetrabutyammonium iodide (Bu$_4$NI) were added to a solution comprising 2 grams (16.93 millimoles) of alpha-hydroxy valine (15) and 20 milliliters of re-distilled DMF, followed by drop-wise addition of 5.86 milliliters (67.72 millimoles) of allyl bromide. The resulting solution was stirred at room temperature for 1 hour. The reaction mixture was concentrated under reduced pressure, diluted with 20 milliliters of H$_2$O, and extracted three times with 20 milliliters aliquots of ether. The combined organic layers were washed once using 15 milliliters of a 10% solution of hydrochloric acid (HCl), once using 15 milliliters of a 5% solution of NaHCO$_3$, and once using 15 milliliters of a saturated solution of NaCl. The resulting washed organic layers were dried in the presence of Na$_2$SO$_4$, filtered, and concentrated under reduced pressure. This reaction yielded 2.53 grams (96% yield) of compound 16 in the form of an orange oil. Compound 16 was used in the subsequent reaction without purification. The following analytical data were obtained for compound 16: $R_f$ 0.50 (25:75, EtOAc: hexane); $^1$H NMR (500 MHz, CDCl$_3$) δ 0.71–0.86 (d, J=6.8 Hz, 3H), 0.92–1.00 (d, J=7.0 Hz, 3H), 2.04–2.10 (m, 1H), 2.65–2.66 (d, J=6.1 Hz, 1H), 4.03–4.05 (dd, J$_1$=5.9 Hz, J$_2$=3.5 Hz, 1H), 4.62–4.70 (m, 2H), 5.24–5.27 (dd, J$_1$=10.4 Hz, J$_2$=1.1 Hz, 1H) and 5.31–5.35 (dd, J$_1$=17.2 Hz, J$_2$=3.5 Hz, 1H), 5.86–5.94 (m, 1H); $^{13}$C NMR (250 MHz, CDCl$_3$) δ 15.93, 18.76, 32.17, 66.04, 75.03, 119.12, 131.48, 174.62; IR (CHCl$_3$) 3521–3458, 2964, 2880, 1735, 1646, 1462, 1367, 1257, 1204, 1136, 1073, 1026, 983, 931 cm$^{-1}$.

Reaction I of FIG. 26B: Synthesis of Compound 17

A solution comprising 0.6827 gram (1.47 millimoles) of compound 13 and 2.5 milliliters of freshly distilled toluene, was placed under an inert atmosphere and cooled to 0° C. A solution comprising 0.232 gram (1.47 millimoles) of compound 16 and 2.5 milliliters of toluene was added drop-wise to the cooled solution of compound 13, followed by the addition of 0.333 gram (1.61 millimoles) of dicyclohexyl-carbodiimide (DCC) and 0.036 gram (0.29 millimole) of DMAP. The reaction mixture was stirred at 0° C. for 2 hours and maintained at room temperature overnight. The reaction was quenched by adding 2 milliliters of a solution comprising MeOH and acetic acid (AcOH) in a ratio of 1:2, and EtOAc, and stirred for 20 minutes at room temperature. The resulting mixture was concentrated under reduced pressure. The residue which remained after this procedure was dissolved in 10 milliliters of ether, which resulted in the formation of a solid, which was removed by filtration. The filtrate was washed once using 10 milliliters of a 10% solution of citric acid, once using 10 milliliters of a 5% solution of NaHCO$_3$, and once using 10 milliliters of brine solution (i.e. a saturated NaCl solution). The organic layer was dried in the presence of anhydrous Na$_2$SO$_4$, filtered, and concentrated. The resulting residue was purified by flash column chromatography, eluting with a solvent mixture comprising ether and hexane in a ratio of from 2 to 98, respectively, to 12 to 88, respectively. Concentration of the eluant under reduced pressure yielded 0.5774 gram (65% yield) of compound 17 in the form of a colorless oil. The following analytical data were obtained for compound 17: Rf 0.55 (20:80-ethyl acetate:hexane); $^1$H NMR (500 MHz, CDCl$_3$) δ 0.85–1.08 (m, 33H), 1.16–1.19 (m, 1H), 1.34–1.36 (m, 1H), 1.80–1.82 (m, 1H), 2.18–2.21 (m, 1H), 2.68–2.73 (m, 2H), 3.78–3.82 (m, 1H), 4.37–4.42 (m, 1H), 4.55–4.64 (m, 2H), 4.77–4.78 (d, J=4.4 Hz, 1H), 4.86–4.88 (d, J=10.7 Hz, 1H), 5.07 (s, 2H), 5.21–5.23 (dd, J$_1$=9.4 Hz, J$_2$=0.9 Hz, 1H), 5.28–5.32 (dd, J$_1$=17.0 Hz, J$_2$=1.2 Hz, 1H), 5.83–5.87 (m, 1H), 7.27–7.34 (m, 5H); $^{13}$C NMR (250 MHz, CDCl$_3$) δ 12.69, 12.93, 14.14, 17.25, 18.12, 18.78, 26.33, 29.98, 34.48, 40.28, 58.15, 66.69, 68.67, 70.66, 76.74, 118.82, 128.01, 128.40, 128.47, 136.75, 131.63, 156.48, 169.13, 170.78; IR (CHCl$_3$) 3380, 2964, 2867, 1743, 1508, 1463, 1374, 1201, 1129, 994, 882 cm$^{-1}$; HRMS m/z calculated for C$_{33}$H$_{55}$NSiO$_7$Na (M$^+$Na$^+$): 628.364552, found 628.365878; Anal. Calculated for C$_{33}$H$_{55}$NSiO$_7$: C, 65.41; H, 9.16. Found: C, 65.09; H, 9.05.

Reaction J of FIG. 26B: Synthesis of Compound 6

In reaction J, tetrakis-(triphenylphosphine)palladium (Pd (PPh$_3$)$_4$, 0.044 grams, 0.038 millimole) was added to a solution comprising 0.2315 gram (0.38 millimole) of the isostatine-Hiv-allyl ester, compound 17, and 3 milliliters of freshly distilled THF. Freshly distilled morpholine (0.33 milliliters, 3.8 millimoles) was added drop-wise to the resulting mixture. The addition of reagents was performed in a dark hood, and the reaction mixture was maintained with stirring at room temperature and in a dark hood for at least 8 hours. The reaction mixture was concentrated under reduced pressure and diluted with 5 milliliters of CH$_2$Cl$_2$. The solution obtained from this procedure was washed once with 5 milliliters of a solution comprising 1 normal HCl and once using 5 milliliters of H$_2$O. The washed organic layer was dried in the presence of anhydrous Na$_2$SO$_4$, filtered, and concentrated under reduced pressure. The residue was dissolved in 5 milliliters of ether, filtered, and concentrated again under reduced pressure. The residue which remained after these procedure was a white foam corresponding to compound 6 (0.218 grams, quantitative yield). Compound 6 was used in the subsequent reaction without purification.

The synthesis of a linear hexapeptide compound (20) is depicted in FIG. 26C. Compound 5 was prepared as described (Li et al., 1990, J. Am. Chem. Soc. 112:7659–7672).

Reaction K of FIG. 26C: Synthesis of Compound 18

A solution comprising 0.6653 gram (0.74 millimole) of compound 5 and 10 milliliters of MeOH was added to a suspension comprising 0.1996 gram of 10% Palladium on carbon (Pd/C), 10 milliliters of MeOH, and 10 milliliters of EtOAc. The reaction mixture was agitated using a Parr apparatus for 5 hours at room temperature. The resulting slurry was filtered through Celite® and the Celite® was washed with an excess of a solvent mixture comprising MeOH and EtOAc in a ratio of 1 to 1. The filtrate was dried in the presence of anhydrous Na$_2$SO$_4$, filtered, and concentrated under reduced pressure to yield compound 18 (0.552 grams, 98% yield). Compound 18 (i.e. Leucylprolyl-N,O-dimethyltyrosine-N-Boc-O-SEM-threonine) was obtained in the form of a white solid using this procedure, and was used in the subsequent reaction without purification. The following analytical data were obtained for compound 18: Rf 0.03 (40:60, acetone:hexane); $^1$H NMR (500 MHz, CDCl$_3$) δ −0.001 (s, 9H), 0.64–0.86 (m, 2H), 0.88–0.96 (m, 6H), 1.19–1.21 (d, J=6.3 Hz), 1.33–1.34 (d, J=6.3 Hz, 3H, RI), 1.44 (s, 9H), 1.63–1.92 (m, 3H), 1.92–2.01, 2.08–2.24 (m, 4H), 2.73 (s, 3H), 2.86–2.96 (m,), 3.10–3.19 (m, 2H), 3.45–3.72 (m, 4H), 3.75 (s, 3H), 4.34–4.69 (m, 3H), 4.78–4.81 (dd, J$_1$=8.0 Hz, J$_2$=3.3 Hz, 1H), 5.01–5.10 (m, 1H), 5.17–5.52 (m), 7.58–7.60 (d, J=9.7 Hz, 3H), 6.77–6.83 (m, 2H), 7.00–7.10 (m, 2H); $^{13}$C NMR (250 MHz, CDCl$_3$) δ −1.46, 16.87, 17,96, 22.00, 23.19, 23.76, 25.14, 28.16, 29.31, 33.65, 39.31, 47.34, 50.54, 55.37, 55.46, 58.66, 62.25, 68.16, 72.36, 81.15, 89.83, 114.39, 128.75, 128.75, 130.47, 157.04, 158.84, 168.15, 168.95, 169.57, 173.13; IR (CHCl$_3$) 3285, 2951, 1740, 1709, 1641, 1511, 1448, 1365, 1250, 1161 cm$^{-1}$; HRMS m/z calculated for C$_{37}$H$_{63}$N$_4$SiO$_{10}$ (M$^+$H$^+$): 751.4314, found 751.4343; [α]D$^{20}$ −44.68 (c 1.03, CHCl$_3$); Anal. Calculated for C$_{37}$H$_{62}$N$_4$SiO$_{10}$: C, 59.17; H, 8.33; N, 7.46. Found: C, 59.17; H, 8.35; N, 7.26.

Reaction L of FIG. 26C: Synthesis of Compound 19

In reaction L, the entire yield of compound 6 from reaction J was dissolved in 1 milliliter of freshly distilled CH$_2$Cl$_2$ and cooled to 0° C. To this solution was added 0.074 gram (0.40 millimole) of PFPOH, (0.088 grams, 0.46 millimole) of EDAC.HCl, and 0.0093 gram of DMAP (0.076 millimole). The resulting mixture was stirred at 0° C. for 30 minutes. The reaction mixture was maintained at room temperature for an additional 4 hours and diluted with 10 milliliters of CH$_2$Cl$_2$. The organic layer was washed once using 5 milliliters of a 10% solution of HCl, once using 5 milliliters of a 5% solution of NaHCO$_3$, and once using 5 milliliters of a saturated solution of NaCl. The CH$_2$Cl$_2$ layer was dried in the presence of anhydrous Na$_2$SO$_4$, filtered, and concentrated under reduced pressure. The resulting residue was purified by flash column chromatography, eluting with a solvent mixture comprising ether and hexane in a ratio of from 3 to 97, respectively, to 7 to 93, respectively. Concentration of the eluate under reduced pressure yielded 0.2315 gram of a colorless oil corresponding to the PFP ester, compound 19 (83% yield for reaction J of FIG. 26B and reaction L of FIG. 26C). The following analytical data were obtained for compound 19: Rf 0.57 (20:80, EtOAc:hexane); $^1$H NMR (500 MHz, CDCl$_3$) δ 0.86–1.09 (m, 33H), 1.18–1.20 (m, 1H), 1.27–1.29 (m, 1H), 1.84–1.86 (m, 1H), 2.31–2.36 (m, 1H), 2.69–2.72 (m, 1H), 2.80–2.85 (m, 1H), 3.79–3.82 (m, 1H), 4.38–4.42 (m, 1H), 4.78–4.80 (d, J=10.7 Hz, 1H), 4.97–4.98 (d, J=4.4 Hz, 1H), 5.00–5.06 (m, 2H), 7.25–7.29 (m, 5H); $^{13}$C NMR (250 MHz, CDCl$_3$) δ 12.72, 12.95, 14.07, 17.20, 18.09, 18.45, 27.52, 30.19, 34.40, 40.12, 58.17, 65.82, 66.74, 70.47, 127.92, 128.18, 128.33, 136.57, 138.83, 140.06, 140.65, 141.97, 156.56, 165.68, 170.76; IR (CHCl$_3$) 3480, 2962, 2868, 1793, 1730, 1516, 1464, 1381, 1214, 1094, 995, 880 cm$^{-1}$; HRMS m/z calculated for C$_{36}$H$_{50}$NF$_5$SiO$_7$Na (M$^+$Na$^+$): 754.3174, found 754.3191.

Reaction M of FIG. 26C: Synthesis of
Compound 20

A solution comprising 0.2855 gram (0.39 millimole) of compound 19 and 1.5 milliliters of CH$_2$Cl$_2$ was cooled to 0° C. in an ice bath. To this solution 0.17 milliliters (0.98 millimole) of DIEA was added drop-wise, and the resulting mixture was maintained with stirring at 0° C. for 20 minutes. A solution comprising 0.522 gram of compound 18, 0.0095 gram (0.078 millimole) of DMAP, and 1.5 milliliters of CH$_2$Cl$_2$ was added to the solution comprising compound 19 using a syringe. The resulting mixture was stirred at 0° C. for 1 hour and maintained at room temperature for an additional 1 hour. The reaction was quenched at 0° C. by adding 3 milliliters of a saturated solution of NH$_4$Cl and diluting the reaction with 10 milliliters of CH$_2$Cl$_2$. The resulting mixture was separated at room temperature. The aqueous layer was extracted 3 times using 10 milliliters aliquots of CH$_2$Cl$_2$, and the combined organic layers were washed once using 10 milliliters of a 10% solution of HCl, once using 10 milliliters of a 5% solution of NaHCO$_3$, and once using 10 milliliters of a saturated NaCl solution. The washed organic layer was dried in the presence of anhydrous Na$_2$SO$_4$, filtered, and concentrated under reduced pressure. This reaction yielded 0.4861 gram (96% yield) of the fully protected hexapeptide precursor, compound 20. Compound 20 were obtained in the form of a white foam using this procedure, and was used in the subsequent reaction without further purification. Analytical data for hexapeptide 20 was as follows: Rf 0.47 (05:95-acetone:CH$_2$Cl$_2$); $^1$H NMR (500 MHz, CDCl$_3$) δ −0.0008 (s, 9H), 0.73–0.83 (m, 2H), 0.85–0.92 (m, 9H), 0.92–1.08 (m, 21H), 1.45 (s, 9H), 1.13–2.19 (m, 11H), 2.43–2.46 (m, 1H) and 2.54–2.58 (m, 1H), 2.64 and 2.88 (s, 3H, RI), 3.09–3.17 (m, 2H), 3.44–3.73 (m, 4H, 3.75 (s, 3H), 3.79–3.89 (m, 1H), 4.38–4.45 (m, 1H), 4.21–4.35 (m, 3H), 4.70–4.81 (m, 1H), 4.96–5.06 (m, 3H), 5.18–5.43 (m, 3H) and 8.32–8.34 (d, J=9.0 Hz, 3H), 5.46–5.48 (d, J=6.1 Hz, 1H), 6.74–6.83 (m, 2H), 6.95–7.11 (m, 2H), 7.25–7.38 (m, 5H), 7.75–7.77 (d, J=8.5 Hz) and 8.85–8.87 (d, J=10.1 Hz, 2H); $^{13}$C NMR (250 MHz, CDCl$_3$) δ−1.45, 11.73, 12.73, 14.47, 16.54, 17.73, 17.99, 18.14, 18.92, 21.40, 23.54, 24.42, 25.13, 28.21, 28.27, 29.20, 29.67, 30.13, 33.59, 34.86, 39.58, 39.73, 46.87, 49.04, 55.13, 55.39, 56.90, 58.94, 62.24, 66.42, 68.12, 70.96, 72.25, 78.71, 80.39, 89.85, 113.92, 114.37, 127.70, 127.76, 127.86, 128.35, 128.45, 128.81, 128.91, 137.01, 130.44, 130.86, 156.39, 158.40, 158.82, 169.20, 169.75, 169.97, 170.58, 171.77, 173.85; IR (CHCl$_3$) 3275, 2952, 2868, 1735, 1704, 1636, 1511, 1454, 1380, 1365, 1250, 1167, 1110, 1047 cm$^{-1}$; HRMS m/z calculated for C$_{67}$H$_{111}$N$_5$Si$_2$O$_{16}$Na (M$^+$Na$^+$): 1320.7462, found 1320.7520; [α]D$^{20}$ −44.56 (c 1.13, CHCl$_3$); Anal. Calculated for C$_{67}$H$_{111}$N$_5$Si$_2$O$_{16}$: C, 61.95; H, 8.62; N, 5.40. Found: C, 61.75; H, 8.59; N, 5.15.

Cyclization of hexapeptide 20 to yield compound 21 is depicted in FIG. 26D.

Reaction N of FIG. 26D: Synthesis of
Compound 21

A solution comprising 0.3505 gram (0.27 millimole) of compound 20 and 5 milliliters of CH$_2$Cl$_2$ was cooled to 0° C., and 0.21 gram (0.81 millimole) of magnesium bromide etherate (MgBr$_2$.Et$_2$O) was added. The resulting mixture was stirred at 0° C. for 2 hours and maintained at room temperature for an additional 4 hours. The reaction mixture was diluted by adding 10 milliliters of CH$_2$Cl$_2$, and washed once using 10 milliliters of a 10% solution of HCl, and once using 10 milliliters of a saturated NaCl solution. The CH$_2$Cl$_2$ layer was dried in the presence of anhydrous Na$_2$SO$_4$, filtered, and concentrated under reduced pressure. The white foam obtained as a product of this de-protection reaction was used in the subsequent hydrogenolysis reaction without purification. The entire yield of white foam (0.3195 grams) was dissolved in 10 milliliters of MeOH and subjected to hydrogenolysis as described for preparation of compound 18. This hydrogenolysis reaction yielded 0.296 gram of a white foam which was used in the subsequent coupling reaction without purification. The hydrogenolysis product was dissolved in 27 milliliters of freshly-distilled DMF and cooled to 0° C. To the cooled solution was added 0.123 gram (0.32 millimole) of 2-(1H-9-azobenzotriazole-1-yl)-1,1,3,3-tetramethyluronium hexafluorophosphate (HATU), followed by drop-wise addition of 0.141 milliliters (0.81 millimole) of DIEA. The resulting mixture was stirred at 0° C. for 1 hour and maintained with stirring at room temperature for at least 8 hours. The reaction mixture was concentrated under reduced pressure, diluted with 10 milliliters of EtOAc, and washed once using 10 milliliters of a 10% solution of HCl, once using 10 milliliters of a 5% solution of NaHCO$_3$, and once using 10 milliliters of a saturated NaCl solution. The CH$_2$Cl$_2$ layer was dried in the presence of anhydrous Na$_2$SO$_4$, filtered, and concentrated under reduced pressure. The crude residue obtained from this procedure was purified by flash column chromatography using a solvent mixture comprising acetone and hexane in a ratio of from 5 to 95, respectively, to 15 to 85, respectively. The resulting eluate was concentrated under reduced pressure to yield 0.173 gram of the protected macrocycle, compound 21, in the form of a white foam. The yield of compound 21 represents a 63% yield for the three reactions starting with compound 20 (i.e. the de-protection, hydrogenolysis, and coupling reactions). The following analytical data were obtained for compound 21: Rf 0.55 (30:70, acetone:hexane); $^1$H NMR (500 MHz, CDCl$_3$) δ 0.78–1.07 (m, 39H), 1.21–1.48 (m, 17H), 1.56–1.92 (m, 4H), 1.95–2.11 (m, 2H), 2.43–2.44 (m, 1H), 3.11–3.17 (m, 1H), 2.53 (s, 3H), 2.89–3.02 (m, 1H), 3.30–3.34 (m, 1H), 3.49–3.52 (m, 1H), 3.60–3.62 (m, 1H), 3.66–3.70 (m, 1H), 3.77 (s, 3H), 4.14–4.19 (m, 1H), 4.37–4.43 (m, 1H), 4.46–4.48 (d, J=7.6 Hz, 1H), 4.55–4.86 (m, 1H), 4.88–4.91 (m), 7.60–7.66 (m, 4H), 6.82–6.83 (d, J=8.5 Hz, 2H), 7.06–7.07 (d, J=8.5 Hz, 2H), 7.41–7.48 (m, 2H); $^{13}$C NMR (250 MHz, CDCl$_3$) δ 12.24, 12.66, 14.21, 15.11, 15.61, 17.98, 18.60, 18.74, 19.31, 21.10, 23.92, 25.24, 27.21, 28.42, 30.48, 34.87, 37.92, 39.00, 41.65, 47.10, 48.52, 55.67, 56.16, 57.25, 63.26, 66.33, 68.65, 71.78, 80.46, 81.66, 114.50, 130.31, 130.82, 156.40, 159.01, 169.13, 170.90, 171.34, 172.78, 176.75; IR (CHCl$_3$) 3330, 2952, 2876, 1735, 1629, 1508, 1447, 1243, 1168, 1024, 843 cm$^{-1}$; HRMS m/z calculated for C$_{53}$H$_{89}$N$_5$SiO$_{12}$Na (M$^+$Na$^+$): 1038.6175, found 1038.6166.

The final reactions in the total synthesis of (−) Tamandarin A, 101, are depicted in FIG. 26E. Compound 4 was prepared in the manner previously reported in Li et al. (1990, J. Am. Chem. Soc. 112:7659–7672).

Reaction O of FIG. 26E: Synthesis of Compound 22

A solution comprising 167 milligrams (0.165 millimole) of protected macrocycle (21) and 20 milliliters of EtOAc was cooled to −30° C. Gaseous HCl was introduced into the solution, and the temperature of the reaction mixture was maintained between −10° C. to −20° C. during introduction of HCl. The reaction mixture was stirred and maintained at a temperature of between −10° C. to −20° C. for an additional 30 minutes. The reaction mixture was warmed to 0° C. and maintained at 0° C. for 1 hour. The reaction vessel was purged with N$_2$ gas for at least 30 minutes while the temperature of the vessel was maintained at 0° C. The purged solution was warmed to room temperature and concentrated under reduced pressure. The residue remaining after concentration of the reaction was triturated and washed by decanting using three 5 milliliter aliquots of a solvent mixture comprising tert-butylmethyl ether and hexane in a ratio of 1 to 4, respectively. The solid which was produced by this procedure was collected by filtration and dried under reduced pressure to provide 127.5 milligrams (quantitative yield) of the hydrochloride salt of compound 22. Compound 22 was obtained as a white solid, and was used in the final coupling reaction without purification.

Reaction P of FIG. 26E: Synthesis of (−) Tamandarin A (Compound 101)

A solution comprising 63.3 milligrams (0.082 millimole) of compound 22, 37.7 milligrams (0.12 millimole) of compound 4, and 0.50 milliliters of CH$_2$Cl$_2$ was cooled to 0° C. in an ice bath. To this cooled solution was added 53.1 milligrams (0.12 millimole) of benzotriazole-1-yl-oxy-tris (dimethylamino)-phosphonium hexafluorophosphate (BOP) and 0.035 milliliters (0.32 millimole) of NMM. The reaction mixture was stirred for 30 minutes at 0° C. and allowed to warm to room temperature. The reaction mixture was maintained with stirring at room temperature for at least an additional 8 hours. The resulting solution was diluted with 2 milliliters of a saturated solution of NaCl and extracted with 10 milliliters of EtOAc. The extracted organic layer was washed once using 10 milliliters of a 10% solution of HCl, once using 10 milliliters of a 5% solution of NaHCO$_3$, and once using 10 milliliters of a saturated solution of NaCl. The washed organic layer was dried in the presence of anhydrous Na$_2$SO$_4$, filtered, and concentrated under reduced pressure. The crude residue was purified by flash column chromatography using a solvent mixture comprising MeOH and CH$_2$Cl$_2$ in a ratio of from 2 to 98, respectively, to 5 to 95, respectively. This procedure yielded 0.0471 gram of tamandarin A (101) in the form of a yellow-greenish solid. The yield of compound 101 was 56%, as calculated for both reactions O and P, and 12% as calculated for reactions A-F, I, J, and L-P (i.e. starting with D-allo-isoleucine). The following analytical data were obtained for tamandarin A (101): Rf 0.57 (10:90-MeOH:CH$_2$Cl$_2$); $^1$H NMR (500 MHz, CDCl$_3$) δ 0.86–1.08 (m, 24H), 1.19–2.30 (dd, J$_1$=17.1 Hz, J$_2$=7.9 Hz, 1H), 3.29–3.33 (d, J=17.0 Hz, 1H), 2.62 (s, 3H), 3.14 (s, 3H), 3.16–3.21 (dd, J$_1$=14.4 Hz, J$_2$=11.1 Hz, 1H), 3.41–3.45 (m, 1H), 3.59–3.80 (m, 5H), 3.82 (s, 3H), 3.90–3.95 (m, 1H), 4.03–4.08 (m, 1H), 4.29–4.30 (m, 1H), 4.37–4.42 (m, 1H), 4.67–4.69 (m, 1H), 4.74–4.77 (m, 1H), 4.89–4.93 (m, 1H), 5.06 (d, J=4.3 Hz, 1H), 5.31–5.35 (q, J$_1$=11.6 Hz, J$_2$=3.3 Hz, 1H), 5.44–5.46 (m, 1H), 6.86–6.88 (d, J=8.3 Hz, 2H), 7.09–7.11 (d, J=8.3 Hz, 2H), 7.37–7.39 (d, J=9.1 Hz, 1H), 7.48–7.50 (d, J=5.1 Hz, 1H), 7.78–7.80 (d, J=9.7 Hz, 1H); $^{13}$C NMR (250 MHz, CDCl$_3$) δ 11.78, 14.07, 16.52, 17.55, 18.93, 20.28, 20.90, 21.32, 23.47, 23.79, 24.83, 24.90, 25.98, 27.33, 27.96, 28.40, 30.11, 31.26, 33.55, 33.93, 35.73, 38.70, 39.41, 39.65, 46.66, 47.02, 48.28, 54.91, 55.27, 56.71, 56.97, 57.90, 66.07, 66.22, 68.98, 70.70, 78.87, 114.08, 130.07, 130.33, 156.62, 168.52, 169.57, 170.11, 170.35, 170.59, 171.09, 172.67, 173.84, 174.53; IR (CHCl$_3$) 3330, 2952, 2876, 1735, 1629, 1508, 1447, 1243, 1168, 1024, 843 cm$^{-1}$; HRMS m/z calculated for C$_{54}$H$_{85}$N$_7$O$_{14}$Na (M$^+$Na$^+$): 1078.6052, found 1078.6044; [α]$_D^{20}$ −43.93 (c 1.05, CHCl$_3$).

The inventors believe that the series of reactions disclosed above represent the first stereoselective synthesis of (−) Tamandarin A.

Example 2

Biological Activity of Tamandarin A

The experiments described in this example demonstrate that tamandarin A is an effective protein synthesis inhibitor and anti-tumor agent. Initial results are shown in Table 2 for inhibition of protein biosynthesis (column 1), cytotoxicity (column 2), and anti-tumor activity (column 3) of tamandarin A, as compared to the related anti-tumor compound didemnin B. The results in Table 2 are given in units of concentration of the selected compound.

TABLE 2

| Compound | Protein Synthesis | Cytotoxicity (NCI-60 Mean) | | Anti-tumor activity (Assay Mean) |
|---|---|---|---|---|
| Tamandarin A | 1.3 μM | GI$_{50}$ = 10.4 μM | LC$_{50}$ = 4.8 μM | 1.31 nM |
| Didemnin B | 4 μM | GI$_{50}$ = 1.8 pM | LC$_{50}$ = 7.4 nM | 1.58 nM |

As used herein, "GI$_{50}$" refers to the dose of a compound which is capable of producing 50% inhibition of cell growth. GI$_{50}$ is assessed by comparing growth of cells to which a compound has been administered with growth of the same cells to which the compound has not been administered.

As used herein, "LC$_{50}$" refers to the dose of a compound which is capable of producing 50% lethality in cells. LC$_{50}$ is assessed by comparing death of cells in a population of cells to which a compound has been administered with the death of cells in a population of the same cells to which the compound has not been administered.

"NCI-60" refers to a 60 tumor cell line panel which from the National Cancer Institute (NCI, Frederick, MD). "NCI-60 Mean" is the average GI$_{50}$ or LC$_{50}$ for the panel treated with the selected compound.

These in vitro findings indicate that tamandarin A exhibits comparable potency to didemnin B, a known anti-cancer agent. Tamandarin A is significantly less cytotoxic in these assays than is didemnin B. The comparison indicate the usefulness of tamandarin A and other didemnin analogs as pharmacological agents having anti-cancer and other activities characteristic of didemnin B.

Example 3

Synthesis of (−)Dehydrotamandarin

A method of synthesizing (−) dehydrotamandarin is described in this example. The method involves the macrocyclic compound 22, which can be generated as described in Example 1. The method described in this Example is illustrated in FIG. 37, and begins with synthesis of compound 27, depicted in FIG. 37A.

Reaction Q of FIG. 37A: Synthesis of Compound 26

To a solution comprising 0.1084 gram (0.33 millimole) of compound 25 and 1 milliliter of freshly-distilled $CH_2Cl_2$ was added 0.182 g (0.43 millimole) of Dess-martin periodinane. The resulting mixture was stirred at room temperature for 4 hours. The reaction mixture was diluted with 10 milliliters of ether and poured into 6 milliliters of a saturated $NaHCO_3$ solution comprising 5% $Na_2S_2O_3$. Another 10 milliliter aliquot of ether was added to the bi-phasic mixture, and the layers were separated. The organic layer was washed once using 10 milliliters of a saturated $NaHCO_3$ solution, and once using 10 milliliters of water. The washed organic layer was dried in the presence of anhydrous $Na_2SO_4$, filtered, and concentrated under reduced pressure. The residue obtained by this procedure was purified by flash column chromatography, eluting with a solvent mixture comprising MeOH and $CH_2Cl_2$ in a ratio of 5 to 95, respectively, to yield 0.083 gram of purified compound 26 (77% yield) in the form of a white foam. The following analytical data were obtained for compound 26: $R_f$ 0.61 (10:90-MeOH:$CH_2Cl_2$); $^1$H NMR (500 MHz, $CDCl_3$) δ 0.86–1.05 (m, 6H), 1.41–1.54 (m, 1H), 1.70–1.74 (m, 2H), 1.87–1.89 (m, 3H) and 2.05–2.19 (m, 1H), 2.33 (s, 3H), 2.97 (s, 2H), 3.59–3.63 (m, 2H), 3.70 (s, 3H), 4.95–4.98 (t, J=7.97 Hz, 1H), 5.11–5.13 (m, 1H); HRMS m/z calculated for $C_{16}H_{26}N_2O_5$ (M$^+$H$^+$): 327.1920, found 327.1912; [α]$^{20}$D+1.14 (c 0.49, $CHCl_3$).

Reaction R of FIG. 37A: Synthesis of Compound 27

A solution comprising 0.0678 gram (0.21 millimole) of compound 26, 4 milliliters of distilled THF, and 4 milliliters of MeOH was cooled to 0° C. To this solution, 8 milliliters of a solution comprising 0.2 molar LiOH was added. The reaction mixture was initially maintained with stirring at 0° C. for 1 hour, after which the reaction mixture was warmed to room temperature and maintained with stirring for at least an additional 8 hours. The resulting mixture was concentrated under reduced pressure, cooled to 0° C., and acidified to pH 3 by adding 1 normal $KHSO_4$. The acidified mixture was extracted three times with 5 milliliters aliquots of EtOAc. The combined EtOAc layers were dried in the presence of anhydrous $Na_2SO_4$, filtered, and concentrated under reduced pressure to yield 0.042 gram (64% yield) of compound 27 in the form of a white solid. The following analytical data were obtained for compound 27: $^1$H NMR (500 MHz, $CDCl_3$) δ 0.86–1.03 (m, 6H), 1.35–1.50 (m, 1H), 1.70–1.77 (m, 2H), 1.85–1.93 (m, 2H) and 2.07–2.18 (m, 2H), 2.33 (s, 3H), 3.02 (s, 3H), 3.58–3.86 (m, 2H), 4.78–4.81 (m, 1H), 5.08–5.12 (m, 1H); $^{13}$C NMR (250 MHz, $CDCl_3$) δ 21.26 and 22.55, 23.21, 24.64, 26.36 and 28.17, 31.16, 37.09, 45.70, 56.79, 58.66, 163.32, 173.12, 174.59, 199.07.

Reaction S of FIG. 37B: Synthesis of (−)Dehydrotamandarin (Compound 133)

A solution comprising 19.7 milligrams (0.063 millimole) of compound 27, 33.4 milligrams (0.042 millimole) of compound 22, and 0.50 milliliters of $CH_2Cl_2$ was cooled to 0° C. in an ice bath. To this cooled solution was added 28 milligrams (0.063 millimole) of BOP and 0.0185 milliliters (0.17 millimole) of NMM. The reaction mixture was stirred for 30 minutes at 0° C. and allowed to warm to room temperature. The reaction mixture was maintained with stirring at room temperature for at least an additional 8 hours. The resulting solution was diluted with 2 milliliters of a saturated solution of NaCl and extracted with 10 milliliters/EtOAc. The extracted organic layer was washed once using 5 milliliters of a 10% solution of HCl, once using 5 milliliters of a 5% solution of $NaHCO_3$, and once using 5 milliliters of a saturated solution of NaCl. The washed organic layer was dried in the presence of anhydrous $Na_2SO_4$, filtered, and concentrated under reduced pressure. The crude residue was purified by flash column chromatography, eluting with a combination of solvent mixtures comprising MeOH and $CH_2Cl_2$ in ratios from 2 to 98, respectively, to 10 to 90, respectively, to yield 18.1 milligrams of dehydrotamandarin (133) in the form of a yellow-white solid. The yield of compound 133 was 41%, as calculated for both reaction O (i.e. the de-protection of compound 21 to yield compound 22 in Example 1) and reaction S. The following analytical data were obtained for dehydrotamandarin A: $R_f$ 0.48 (10:90-MeOH:$CH_2Cl_2$); $^1$H NMR (500 MHz, $CDCl_3$) δ 0.80–1.00 (m, 24H), 1.16–1.45 (m 11H), 1.51–2.25 (m, 10H), 2.38–2.48 and 3.19–3.30 (m, 2H), 2.52–2.53 (d, J=6.2 Hz, 3H), 2.57 (s, 3H), 3.04 and 3.08 (s, 3H, rotomers), 3.12–3.16 (m, 1H) and 3.31–3.35 (m, 1H), 3.53–3.72 (m, 5H), 3.77 (s, 3H), 3.81–4.03 (m, 1H), 4.05–4.10 (m, 1H), 4.25–4.26 (m, 1H), 4.61–4.65 (m, 1H), 4.68–4.71 (m, 1H), 4.85–4.88 (m, 1H), 5.00–5.01 (d, J=4.6 Hz, 1H), 5.15–5.20 (m, 1H), 5.28–5.31 (m, 1H), 6.81–6.83 (d, J=7.5 Hz, 2H), 7.05–7.07 (d, J=8.2 Hz, 2H), 7.28–7.30 (d, J=9.8 Hz, 1H) and 7.33–7.35 (d, J=10.2 Hz, 1H), 7.39–7.40 (d, J=5.5 Hz, 1H), 7.72–7.74 (d, J=9.7 Hz, 1H) and 7.78–7.80 (d, 9.7 Hz, 1H); $^{13}$C NMR (500 MHz, $CDCl_3$) δ 11.80, 14.11, 16.52, 17.63, 18.91, 20.87, 21.33, 22.32, 23.53, 24.89 (overlap), 24.83, 27.08, 27.35, 27.99, 29.62, 30.13, 31.00, 33.56, 34.04, 35.10, 35.84, 38.90, 39.65, 46.72, 48.29, 48.81, 54.78, 55.27 (overlap), 56.91, 57.46, 58.91, 66.10, 68.92, 70.90, 78.94, 114.12, 130.00, 130.36, 158.68, 161.50, 168.43, 169.59, 170.61, 171.00, 172.26, 173.00, 174.52, 197.36; IR (KBr) 3339, 2960, 2927, 2872, 1736, 1715, 1655, 1633, 1508, 1460, 1438, 1248, 1177, 1085, 1031, 830 cm$^{-1}$; HRMS m/z calculated for $C_{54}H_{83}N_7O_{14}Na$ (M+Na$^+$): 1076.5896, found 1076.5946; [α]$^{20}$D −35.29 (c 0.35, $CHCl_3$).

Example 4

Synthesis of Fluorescent Tamandarin Analogs

A method of synthesizing a fluorescent tamandarin, compound 108, is described in this example. As in Example 3, the method illustrated in this Example involves the macrocyclic compound 22, which can be generated as described in Example 1. The method described in this Example is illustrated in FIG. 38, and is initiated with synthesis of compound 206a, depicted in FIG. 38A.

Reaction T of FIG. 38A: Synthesis of Compound 205a.

A solution comprising 10.00 grams (49.5 millimoles) of diethyl 1,3-acetonedicarboxylate, 7.12 grams (51.9 millimoles) of m-dimethylaminophenol, 8.56 grams (62.8 millimoles) of zinc chloride, and 25 milliliters of absolute ethanol was maintained at reflux for 13 hours. The reaction mixture was diluted with 50 milliliters of EtOAc and washed using 25 milliliters of $H_2O$. The aqueous layer obtained from this procedure was extracted three times with 50 milliliters aliquots of EtOAc. The combined EtOAc layers were dried in the presence of anhydrous magnesium sulfate ($MgSO_4$), filtered, and concentrated under reduced pressure. The resulting crude solid was re-crystallized from absolute ethanol to yield 2.64 grams (20% yield) of compound 205a in the form of orange crystals. The following analytical data were obtained for compound 205a: mp 131–132° C.; $R_f$ ( ).20 (acetone/hexane 30:70); $^1$H NMR (500 MHz, $CDCl_3$) δ 1.22 (3H, t, J=7.1 Hz), 3.01 (6H, s), 3.64 (2H, s), 4.15 (2H, q, J=7.2 Hz), 6.02 (1H, s), 6.48 (1H, d, J=2.6 Hz), 6.58 (1H, dd, $J^1$=2.6 Hz, $J^2$=8.9 Hz), 7.37 (1H, d, J=8.9); $^{13}$C NMR (125 MHz, $CDCl_3$) δ 14.02, 38.16, 40.01, 61.49, 98.28, 108.45, 108.93, 110.63, 125.22, 148.39, 152.91, 155.89, 161.65, 169.01; IR (KBr) 2907 (w), 1720 (s), 1600 (2), 1534 (m), 1484 (m), 1427 (m), 1405 (s), 1371 (m), 1330 (m), 1232 (m) $cm^{-1}$; HRMS Calculated for$C_{15}H_{18}NO_4$ ($M^+H$): 2.76.1236, found 276.1244. Anal. Calculated for$C_{15}H_{17}NO_4$: C, 65.43; H, 6.23; N, 5.09. Found: C, 65.26; H. 6.36; N, 5.03.

Reaction U of FIG. 38A: Synthesis of Compound 205b.

A solution comprising 0.46 gram (11.0 millimoles) of lithium hydroxide hydrate (LiOH—$H_2O$) and 25 milliliters of $H_2O$ was added to a solution comprising 1.50 grams (5.5 millimoles) of compound 205a and 10 milliliters of THF. The reaction mixture was maintained with stirring at room temperature for 2.5 hours. The resulting solution was washed with 10 milliliters of ether and acidified to pH 2. A precipitate formed upon acidification and was collected by filtration. The precipitate comprised 0.364 gram of compound 205b in the form of yellow crystals. The following analytical data were obtained for compound 205b: mp 166–167° C., $^1$H NMR (500 MHz, $CDCl_3$/DMSO) δ 3.01 (6H, s), 3.62 (2H, s), 6.00 (1H, s), 6.44 (1H, d, J=2.3 Hz), 6.58 (1H, dd, $J^1$=2.4 Hz, $J^2$=8.9 Hz), 7.40 (1H, d, J=9.0 Hz); $^{13}$C NMR (125 MHz, $CDCl_3$/DMSO) δ 38.42, 40.25, 98.34, 108.89, 109.35, 110.67, 125.84, 149.59, 153.22, 156.15, 162.00, 171.33; IR (KBr) 2923 (m), 1690 (s), 1619 (s), 1534 (m), 1404 (m), 1248 (m), 1145 (m), 1055 (m) $cm^{-1}$; HRMS Calculated for$C_{13}H_{14}NO_4$ ($M^+H$): 248.0922, found 248.0929.

Reaction V of FIG. 38A: Synthesis of Compound 206a.

A solution comprising 0.364 gram (1.47 millimoles) of compound 205b and 5 milliliters of freshly-distilled $CH_2Cl_2$ was placed under an argon atmosphere and cooled to ° C. To this solution was added 0.282 gram (1.47 millimole) of EDAC.HCl and 0.035 gram (0.29 millimole) of DMAP. The resulting mixture was stirred for 10 minutes, and 0.246 gram (1.47 millimoles) of glycine tert-butyl ester was added. The reaction mixture was maintained with stirring at 0° C. for 2 hours, warmed to room temperature, and maintained at room temperature for at least 8 additional hours. The reaction mixture was diluted with $CH_2Cl_2$ and washed once using 10 milliliters of a 10% solution of HCl and once using 10 milliliters of a saturated NaCl solution. The combined, washed $CH_2Cl_2$ layers were dried in the presence of anhydrous $MgSO_4$, filtered, and concentrated under reduced pressure. The resulting residue was purified by flash column chromatography, eluting with a solvent mixture comprising equal amounts of EtOAc and $CH_2Cl_2$ to yield 0.250 gram (42% yield) of compound 206a in the form of a yellow solid. The following analytical data were obtained for compound 206a: $^1$H NMR (500 MHz, $CDCl_3$) δ 1.42 (s, 9H), 3.03 (s, 6H), 3.64 (s, 2H), 3.88 (d, J=5.12 Hz, 2H), 6.05 (s, 1H), 6.48 (brs, 1H), 6.58 (d, J=2.5 Hz, 1H), 6.60 (dd, $J^1$=2.6 Hz, $J^2$=8.9 Hz, 1H), 7.45 (d, J=8.9 Hz, 1H); $^{13}$C NMR (125 MHz, $CDCl_3$) δ 168.5, 167.8, 161.6, 156.0, 153.1, 149.2, 125.6, 110.5, 109.2, 108.3, 98.3, 82.5, 42.4, 40.3, 40.1, 27.9; IR ($CHCl_3$) 3450, 1679, 1618, 1530, 1405, 1370, 1230, 1157 $cm^{-1}$; HRMS (CI) m/z calculated for$C_{19}H_{24}N_2O_5$ ($M^+$): 360.1685, Found 360.1686. Anal. Calculated for$C_{19}H_{24}N_2O_5$: C, 63.30; H, 6.72; N, 7.78. Found: C, 62.99; H, 6.60; N, 7.52.

Reaction W of FIG. 38B: Synthesis of Compound 207a.

A solution comprising 0.250 gram (0.69 millimole) of Gly-DACA-tert-butyl ester, compound 206a, and $CH_2Cl_2$ was cooled to 0° C., and maintained for 10 minutes. To the cooled solution a solution comprising 10% trifluoroacetic acid (TFA) was added drop-wise. This addition was completed in 10 minutes. The resulting mixture was maintained with stirring at room temperature for at least 8 hours. The reaction mixture was evaporated to dryness using a rotary evaporator, and the resulting residue, comprising 0.033 gram (0.108 millimole) of compound 206b, was used in the subsequent reaction without further purification.

A solution comprising 0.033 gram (0.108 millimole) of compound 206b and $CH_2Cl_2$ was cooled to 0° C. To the cooled solution was added 0.027 gram (0.108 millimole) of BOP and 0.012 gram (0.108 millimole) of NMM. The resulting mixture was maintained for 30 minutes with stirring. An excess of the methyl ester of N-methyl-D-leucine was added to the stirred mixture, after which the reaction was maintained with stirring at 0° C. for at least 8 hours. The reaction mixture was diluted with $CH_2Cl_2$, and washed once using 10 milliliters of a 10% solution of HCl and once using 10 milliliters of a saturated NaCl solution. The combined, washed $CH_2Cl_2$ layers were dried in the presence of anhydrous $MgSO_4$, filtered, and concentrated under reduced pressure. The resulting residue was purified by flash column chromatography, eluting with a solvent mixture comprising equal amounts of EtOAc and $CH_2Cl_2$. Evaporation of the eluate yielded 0.030 gram (63% yield) of compound 207a in the form of a yellow solid. The following analytical data were obtained for compound 207a: $[\alpha]D^{20}$ +19.08 (c 0.865, $CHCl_3$); $^1$H NMR (500 MHz, $CDCl_3$) δ 0.87 (, J=6.52 Hz, 3H), 0.91 (d, J=6.79 Hz, 3H), 1.40 (m, 1H), 1.69 (m, 2H), 2.85 (s, 3H), 3.01 (s, 6H), 3.63 (s, 2H), 3.67 (s, 3H), 4.06 (m, 2H), 5.22 (dd, $J^1$=10.6 Hz, $J^2$=5.2 Hz, 1H), 6.04 (s, 1H), 6.47 (d, J=2.5 Hz, 1H), 6.57 (dd, $J^1$=2.5 Hz, $J^2$=8.9 Hz, 1H), 6.76 (brs, 1H), 7.42 (d, J=8.9 Hz, 1H); $^{13}$C NMR (125 MHz, $CDCl_3$) δ 171.7, 168.6 167.8, 161.6, 155.9, 152.9, 149.1, 125.4, 110.5, 109.1, 108.4, 98.3, 54.7, 52.3, 41.8, 40.1, 39.9, 37.1, 30.0, 24.8, 23.1, 21.3 cm$^{-1}$. HRMS m/z calculated for C$_{23}$H$_{31}$N$_3$O$_6$ (M$^+$Na$^+$): 468.21 11, Found 468.2133.

Reaction X of FIG. 38B: Synthesis of Compound 207b

A solution comprising 0.135 gram (0.304 millimole) of compound 207a and THF was cooled to 0° C., and a solution comprising 0.025 gram (0.606 millimole) of LiOH.H$_2$O in 2 milliliters of water was added. This addition was completed over a period of 5 minutes. The resulting mixture was maintained with stirring at 0° C. for 30 minutes and then warmed to room temperature. The reaction mixture was maintained at room temperature for 1.5 hours, and then washed twice using 4 milliliter aliquots of ether. The washed aqueous layer was evaporated to dryness under reduced pressure. The resulting residue, comprising compound 207b, was dissolved in a solution comprising 2 milliliters of water and 4 milliliters of EtOAc, cooled to 0° C., and acidified to pH 2 by adding a solution comprising 1 normal KHSO$_4$. The separated aqueous layer formed by this procedure was washed twice with 4 milliliters aliquots of EtOAc. The combined organic layers were dried in the presence of anhydrous MgSO$_4$, filtered, and concentrated to dryness under reduced pressure. The residue resulting from this procedure comprised 0.010 gram (0.023 millimole) of compound 207b, and was used in the subsequent reaction without purification.

Reaction Y of FIG. 38C: Synthesis of Compound 107

A solution comprising 0.010 gram (0.023 millimole) of compound 207b and CH$_2$Cl$_2$ was cooled to 0° C. To this cooled solution were added 0.010 gram (0.023 millimole) of BOP and 0.010 milliliter (0.092 millimole) of NMM. The resulting mixture was maintained with stirring at 0° C. for 10 minutes, and the hydrochloride salt of compound 22 (0.018 gram, 0.023 millimole) was added. The reaction was maintained at 0° C. for 1 hour and at room temperature for at least an additional 8 hours. The resulting solution was diluted with 1 milliliter of brine and extracted twice using 2 milliliter aliquots of EtOAc. The organic layer formed by extraction was washed once using 1 milliliter of a 10% solution of HCl and twice using 1 milliliter aliquots of water. The washed organic layer was dried in the presence of anhydrous MgSO$_4$, filtered, and concentrated under reduced pressure. The resulting residue was purified by flash chromatography, eluting with a solvent mixture comprising acetone and hexane in a ratio of 30 to 70, respectively. Evaporation of the eluate yielded 0.008 gram (30% yield) of fluorescent compound 107. The following analytical data were obtained for compound 107: [α]D$^{20}$ –160.1 (c 0.3, CHCl$_3$); $^1$H NMR (500 MHz, CDCl$_3$) δ 0.73–0.93 (m, 24H), 1.07–1.74 (m, 15H), 2.04 (m, 2H), 2.14 (s, 3H), 2.15 (m, 2H), 2.31 (m, 2H), 2.53 (s, 4H), 2.84 (s, 2H), 3.03 (s, 6H), 3.17 (brd, J=10.4 Hz, 2H), 3.35 (m, 1H), 3.57 (m, 2H), 3.68 (s, 2H), 3.78 (s, 3H), 3.99 (brd, 2H), 4.08–4.12 (m, 3H), 4.55–4.56 (m, 1H), 4.78–4.80 (m, 1H), 4.82–5.01 (m, 2H), 5.13–5.14 (brd, 1H), 6.08 (s, 1H), 6.51 (s, 1H), 6.61 (d, J=9.1 Hz, 1H), 6.83 (d, J=8.54 Hz, 2H), 7.07 (d, J=8.35 Hz, 2H), 7.24–7.41 (m, 3H), 7.51 (d, J=8.90 Hz, 1H), 7,81 (d, J=8.65 Hz, 1H); IR (KBr) 3462, 2953, 2358, 1732, 1658, 1632, 1555, 1538, 1456, cm$^{-1}$; HRMS m/z calculated for C$_{64}$H$_{92}$N$_8$O$_{16}$ (M$^+$Na$^+$): 1251, 6529, Found 1251.6528.

The disclosure of every patent, patent application, and publication cited herein is hereby incorporated herein by reference in its entirety.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of performing a function selected from the group consisting of

I) inhibiting protein synthesis in a cell,
II) inhibiting growth of a cell,
III) inhibiting proliferation of a cell,
IV) inhibiting tumorigenesis in a cell, and
V) enhancing apoptosis of a cell, the method comprising administering to the cell a didemnin analog having the structure

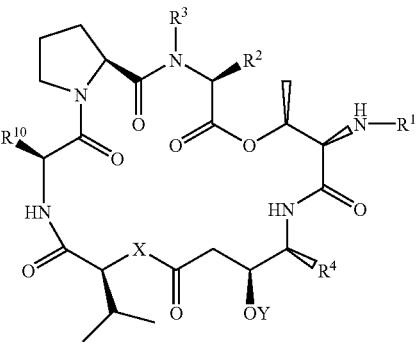

wherein:
i) R$^1$ is selected from the group consisting of
—H,
-(tert-butyloxycarbonyl),
-leucine,
—(N-methyl)leucine,
—(N-methyl)leucine-proline,
—(N-methyl)leucine-proline-lactate,
—(N-methyl)leucine-proline-pyruvate,
—(N-methyl)leucine-proline-lactate-(a first fluorophore),
—(N-methyl)leucine-proline-lactate-glutamine-pyroglutamate,
—(N-methyl)leucine-proline-lactate-glutamine-cyclopentanoate,
—(N-methyl)leucine-proline-alanine-leucine-pyroglutamate, and
—(N-methyl)leucine-proline-(N-methyl-alanine)-leucine-pyroglutamate;

ii) R$^2$ and R$^3$ are one of
(a) R$^2$ is selected from the group consisting of an isoleucine side chain, a valine side chain, an alanine side chain, a norleucine side chain, a norvaline side chain, a leucine side chain, a histidine side chain, a tryptophan side chain, an arginine side chain, a lysine side chain, a second fluorophore, and a substituent having the structure

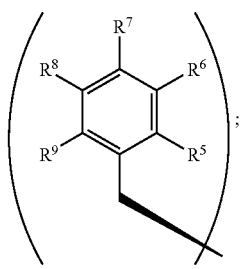

and R³ is selected from the group consisting of —CH₃ and —H; or (b) R² and R³ together form the structure

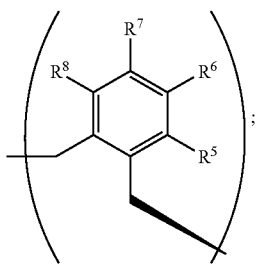

iii) each of R⁵, R⁶, R⁷, R⁸, and R⁹, when present, is independently selected from the group consisting of —H, —OH, —OCH₃, —CO(C₆H₅), —Br, —I, —F, —Cl, —CH₃, and —C₂H₅;

iv) R⁴ is selected from the group consisting of an isoleucine side chain and a valine side chain;

v) X is selected from the group consisting of —O— and —NH—;

vi) Y is selected from the group consisting of —H and a hydroxyl protecting group;

vii) R¹⁰ is selected from the group consisting of a leucine side chain and a lysine side chain; and viii) the molecule is not tamandarin A and is not tamandarin B (compound 105).

2. The method of claim 1, wherein R¹ is selected from the group consisting of
—H,
-(tert-butyloxycarbonyl),
-leucine,
—(N-methyl)leucine,
—(N-methyl)leucine-(S)proline,
—(N-methyl)leucine-(S)proline-(S)lactate,
—(N-methyl)leucine-(S)proline-pyruvate,
—(N-methyl)leucine-(S)proline-(S)lactate-(a first fluorophore),
—(N-methyl)leucine-(S)proline-(S)lactate-glutamine-pyroglutamate,
—(N-methyl)leucine-(S)proline-(S)lactate-glutamine-cyclopentanoate,
—(N-methyl)leucine-(S)proline-alanine-leucine-pyroglutamate, and
—(N-methyl)leucine-(S)proline-(N-methyl-alanine)-leucine-pyroglutamate.

3. The method of claim 1, wherein R¹ is selected from the group consisting of
—H,
-(tert-butyloxycarbonyl),
-leucine,
—(N-methyl)leucine,
—(N-methyl)leucine-(S)proline,
—(N-methyl)leucine-(S)proline-(S)lactate,
—(N-methyl)leucine-(S)proline-pyruvate,
—(N-methyl)leucine-(S)proline-(S)lactate-(a first fluorophore),
—(N-methyl)leucine-(S)proline-(S)lactate-(S)glutamine-(S)pyroglutamate,
—(N-methyl)leucine-(S)proline-(S)lactate-(S)glutamine-(S)cyclopentanoate,
—(N-methyl)leucine-(S)proline-(S)alanine-(S)leucine-(S)pyroglutamate, and
—(N-methyl)leucine-(S)proline-(N-methyl-S-alanine)-(S)leucine-(S)pyroglutamate.

4. The method of claim 1, wherein R₁ is —(N-methyl-R-leucine).

5. The method of claim 1, wherein R¹ is —(N-methyl)leucine-(S)proline-pyruvate.

6. The method of claim 1, wherein the didemnin analog is selected from the group consisting of (compound 133)

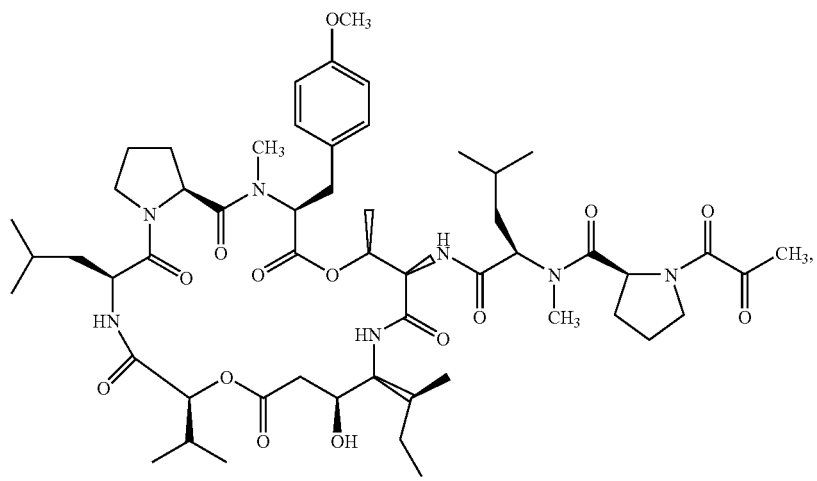

and
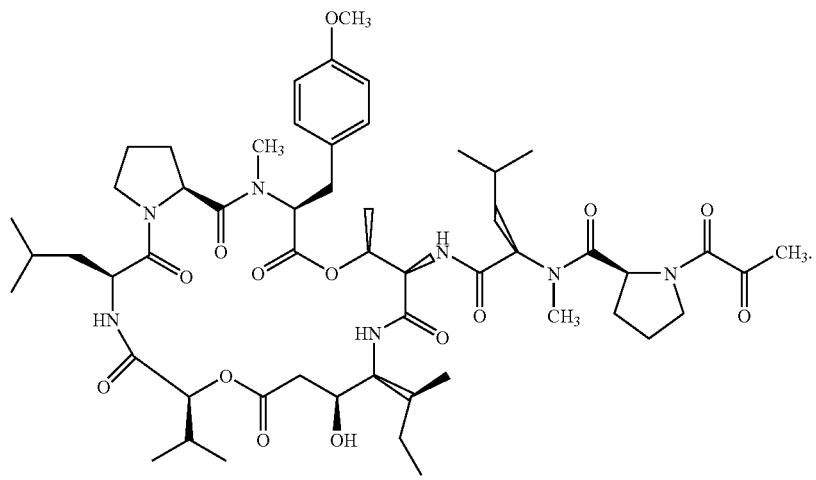
(compound 134)
7. The method of claim 1, wherein Y is —H, and wherein R² has the structure
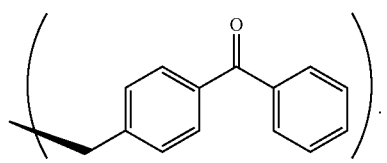
8. The method of claim 1, wherein R² is a lysine side chain and Y is —H.
9. The method of claim 1, wherein the didemnin analog is selected from the group consisting of
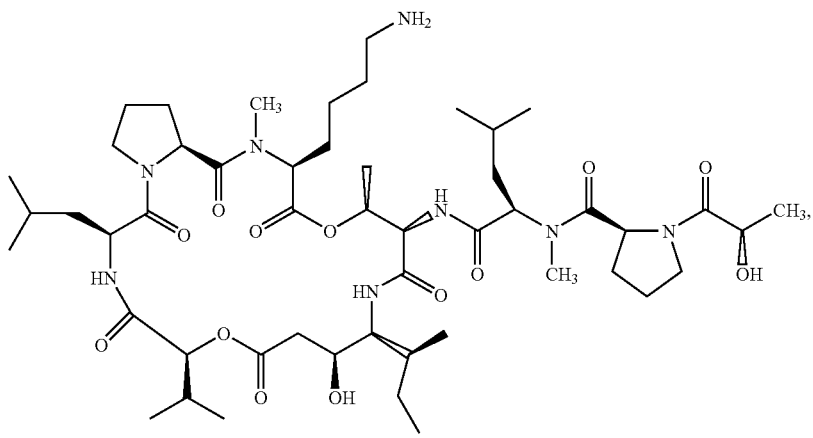
(compound 115)

-continued
(compound 117)
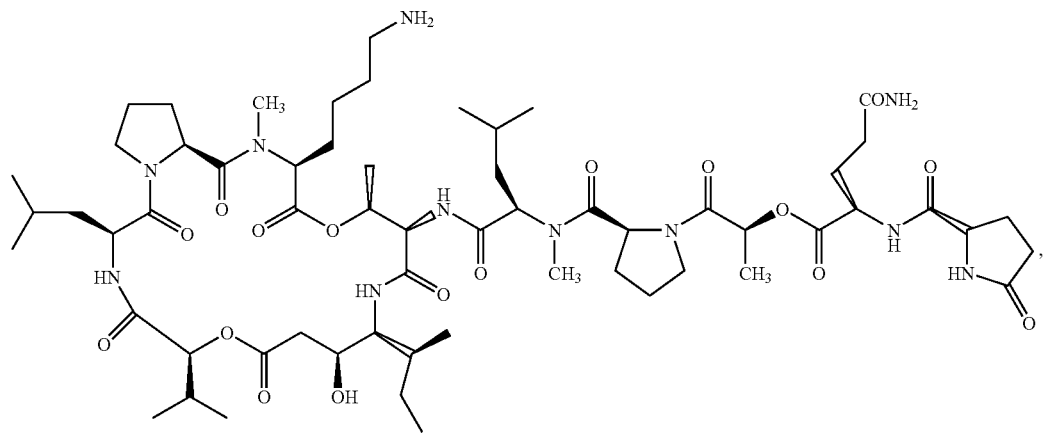
(compound 118)
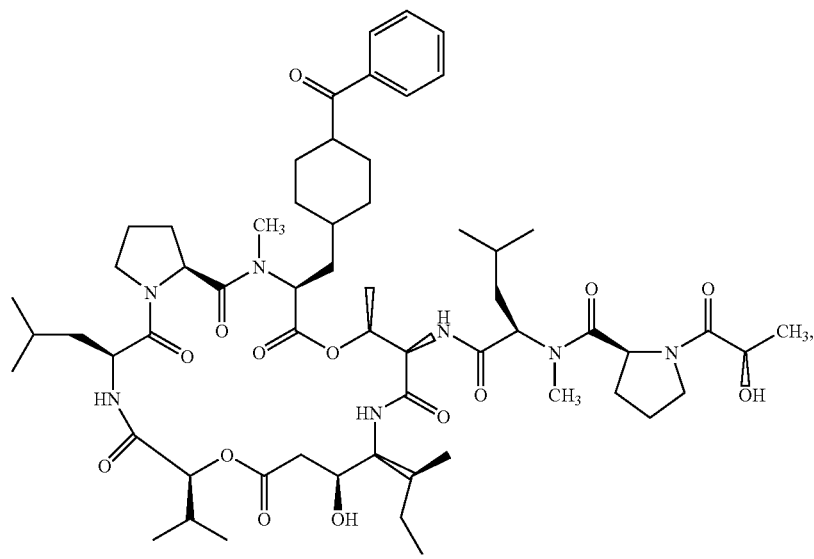
(compound 119)
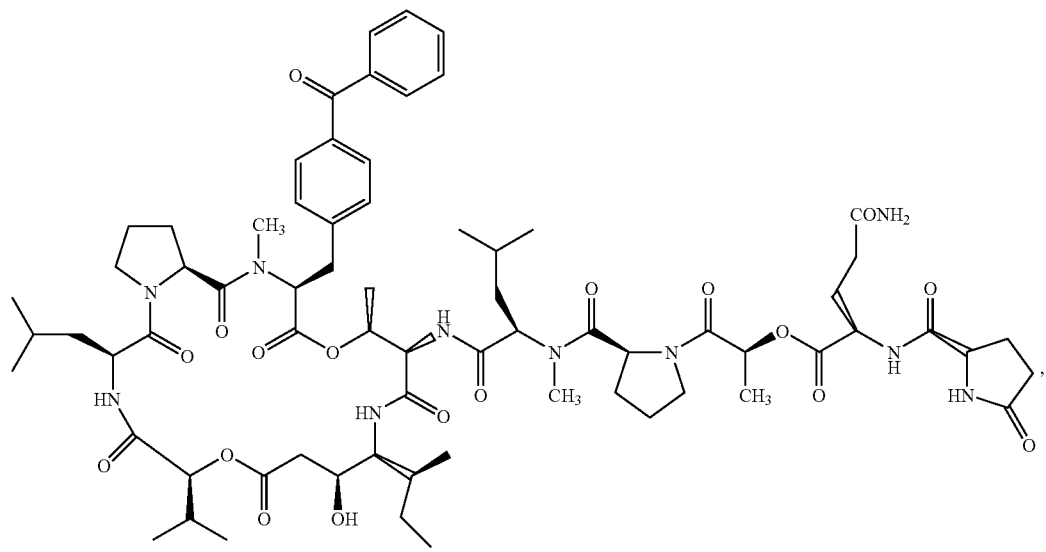

(compound 121)
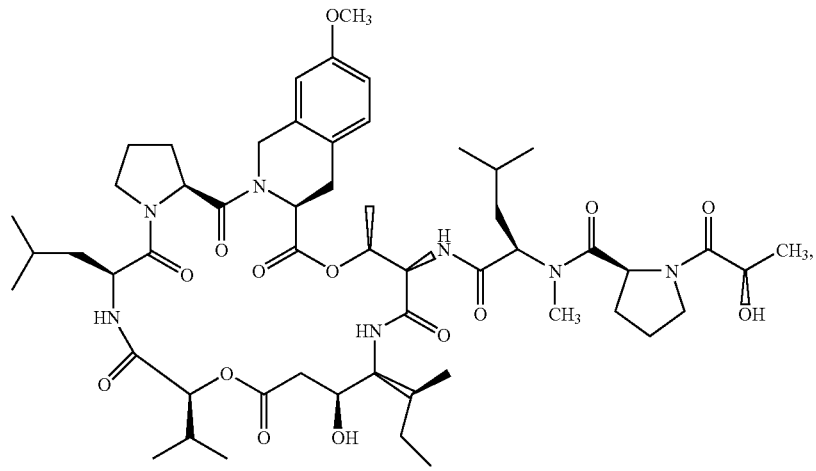
(compound 122)
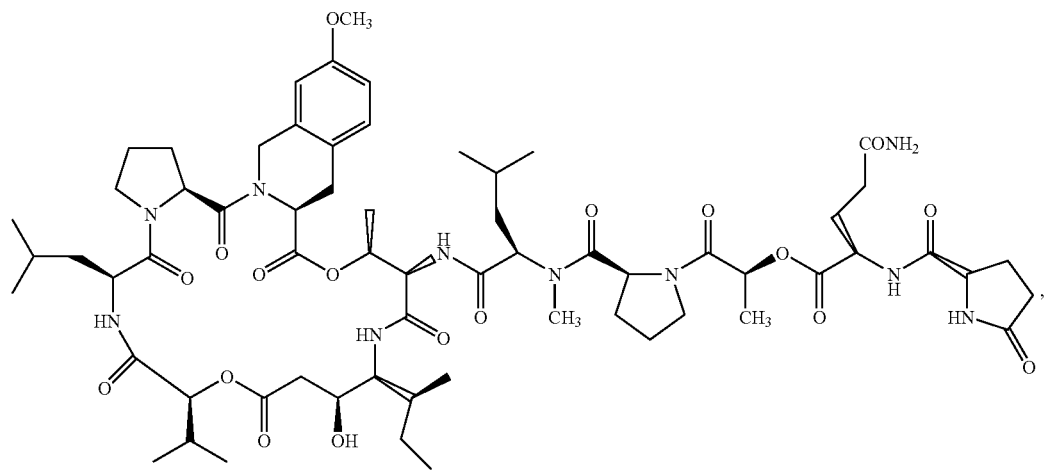
(compound 127)
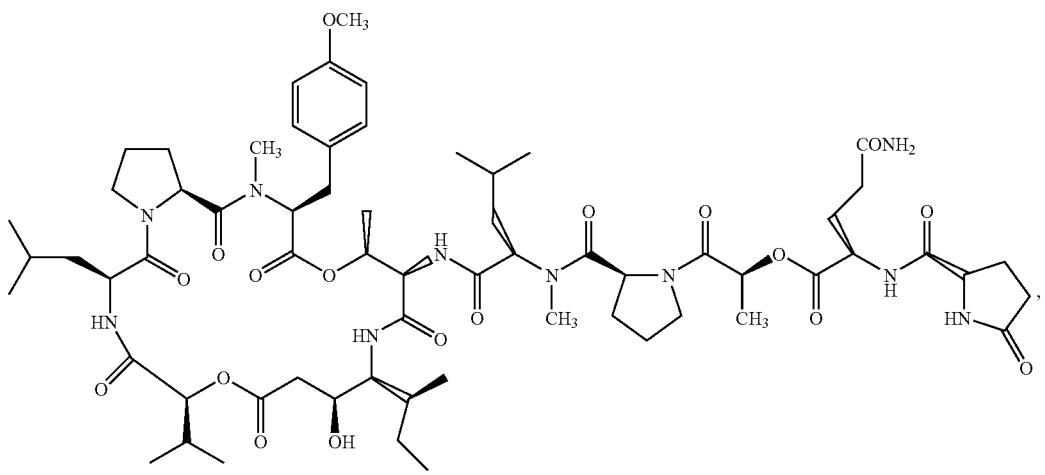

(compound 128)
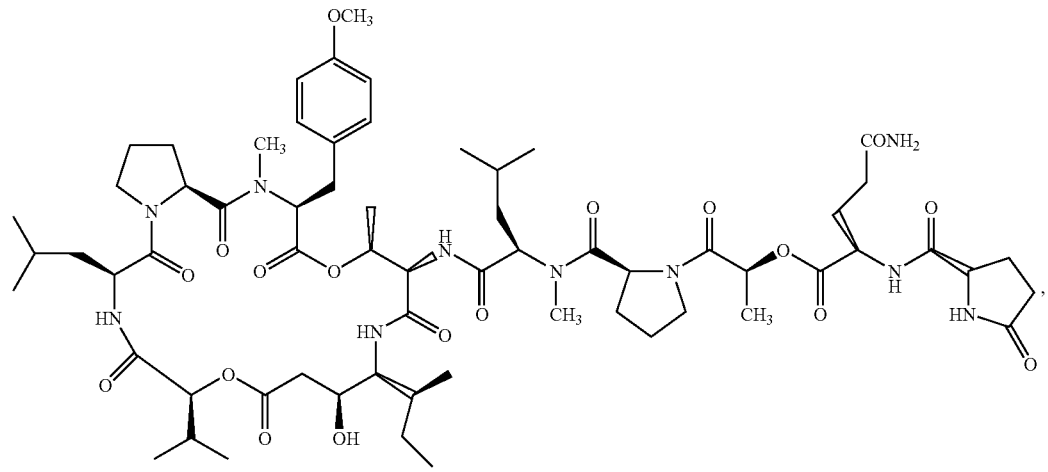
(compound 129)
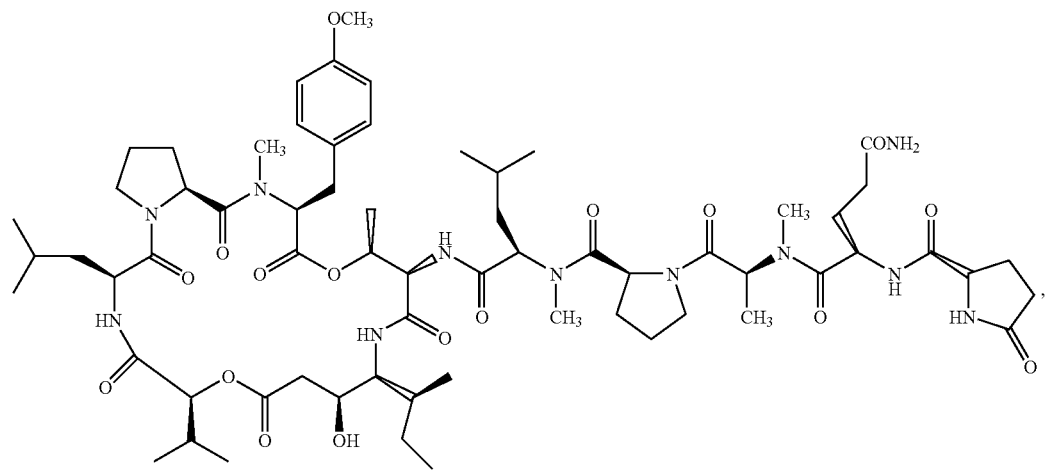
(compound 130)
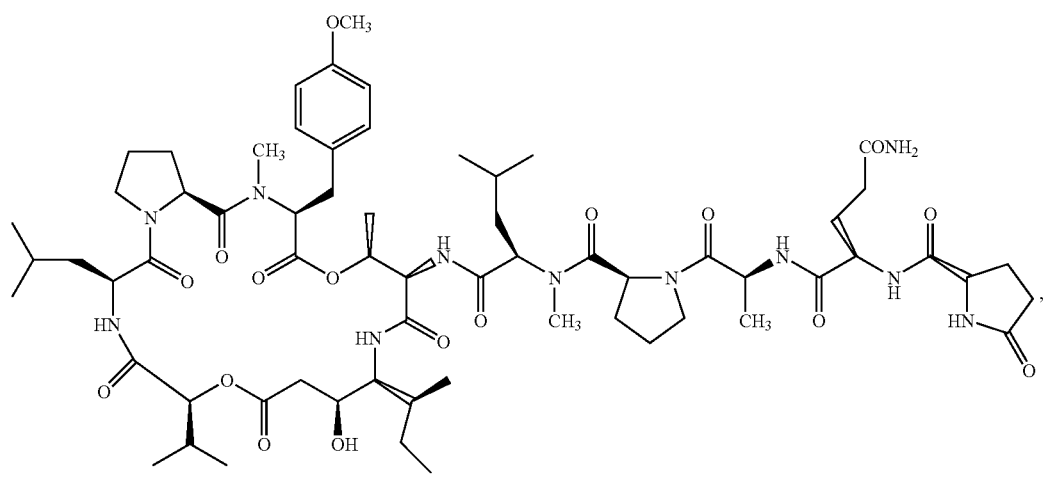

(compound 136)
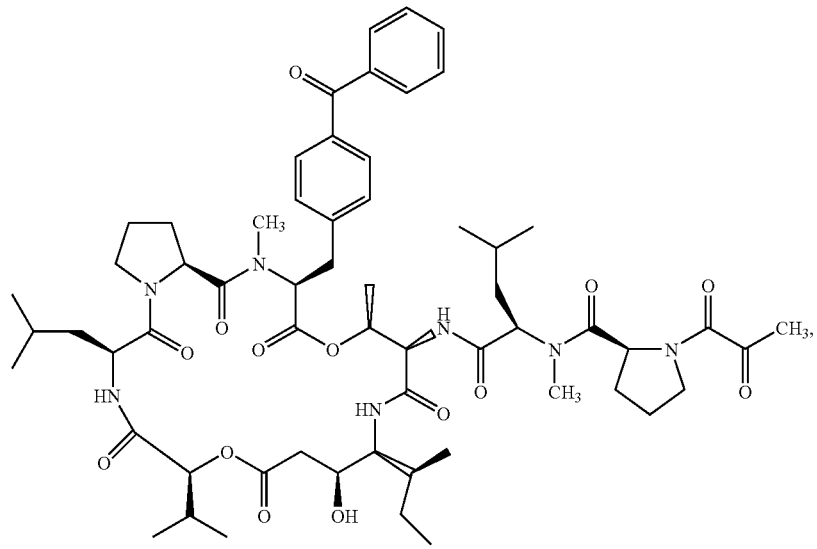
(compound 137)
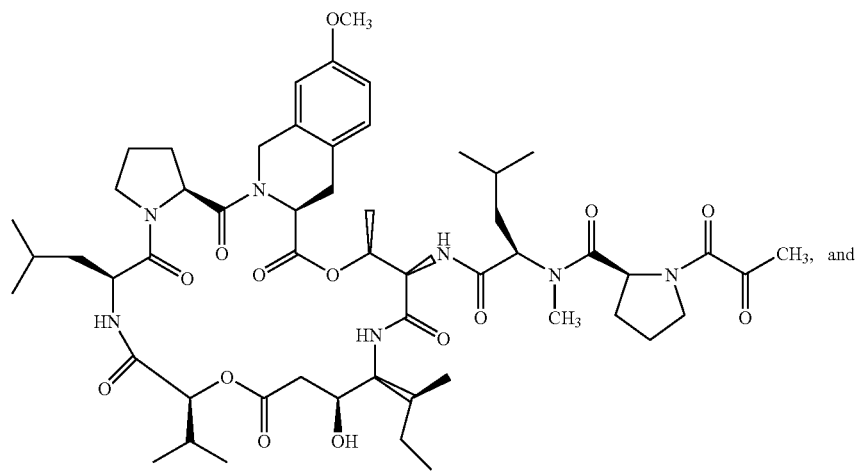
and
(compound 139)
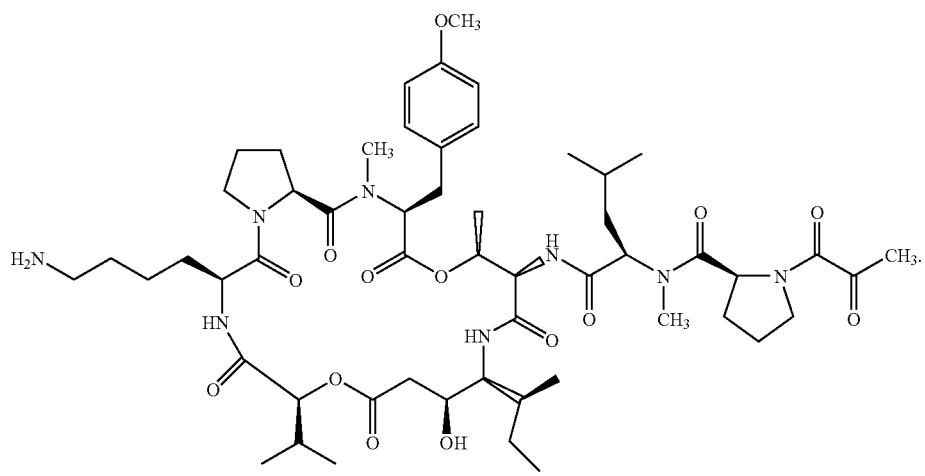

10. The method of claim 1, wherein the didemnin analog is administered as a composition further comprising a pharmaceutically acceptable carrier.

11. The method of claim 1, wherein Y is —H, X is —O—, and $R_1$ is —(N-methyl-R-leucine)-(S)proline-(S)glutamine-(S)pyroglutamate.

12. The method of claim 11, wherein the didemnin analog is selected from the group consisting of

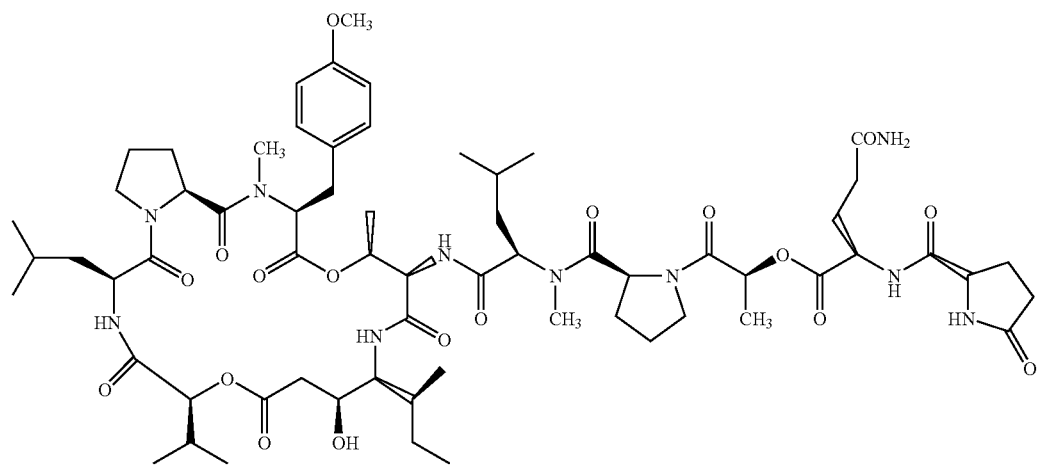

(compound 103)

and

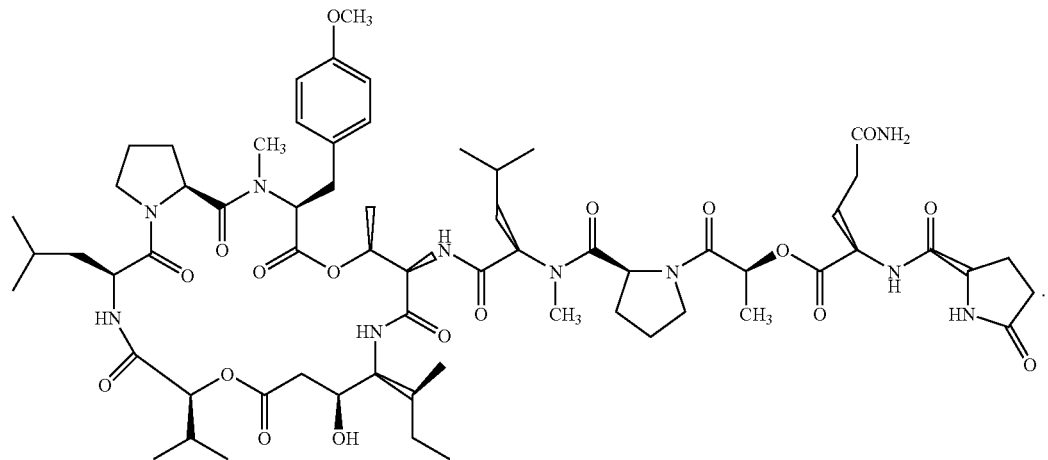

(compound 104)

13. The method of claim 1, wherein $R^4$ is a valine side chain, Y is —H, and X is —O—.

14. The method of claim 13, wherein the didemnin analog is selected from the group consisting of

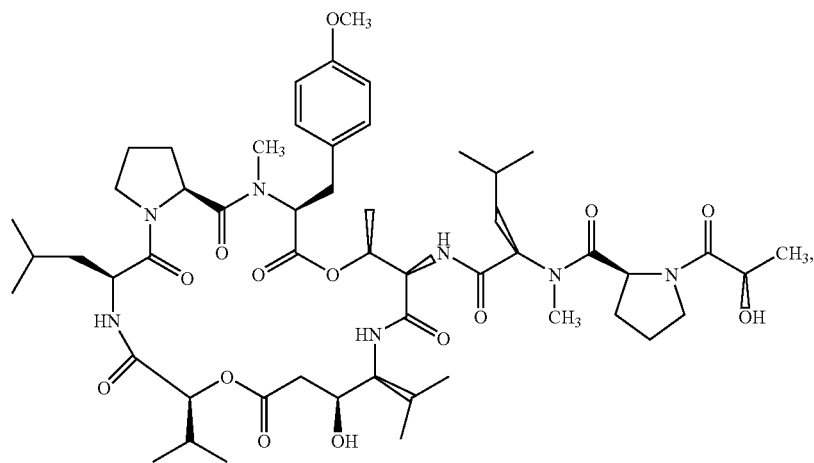
(compound 106)
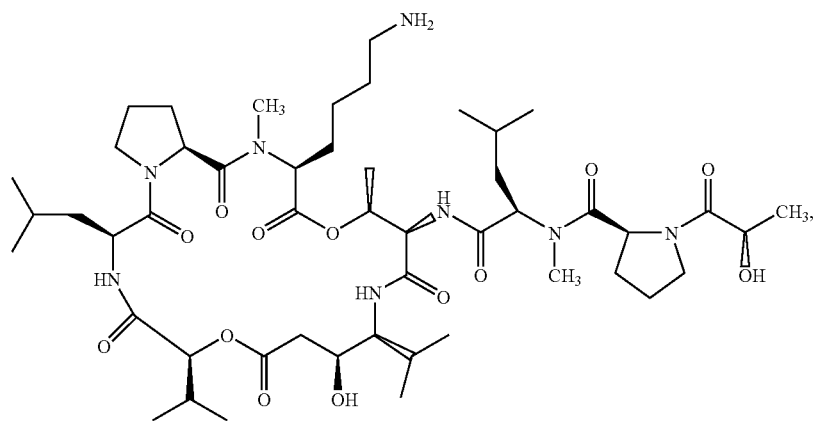
(compound 116)
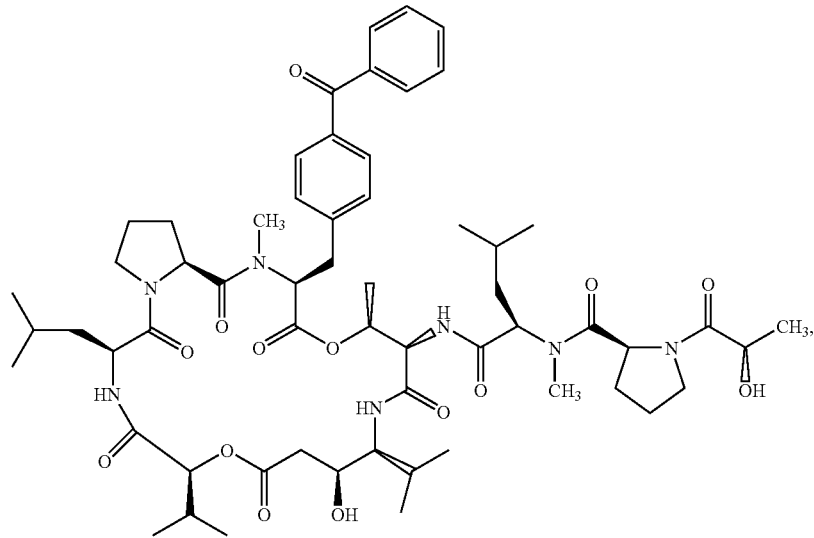
(compound 120)

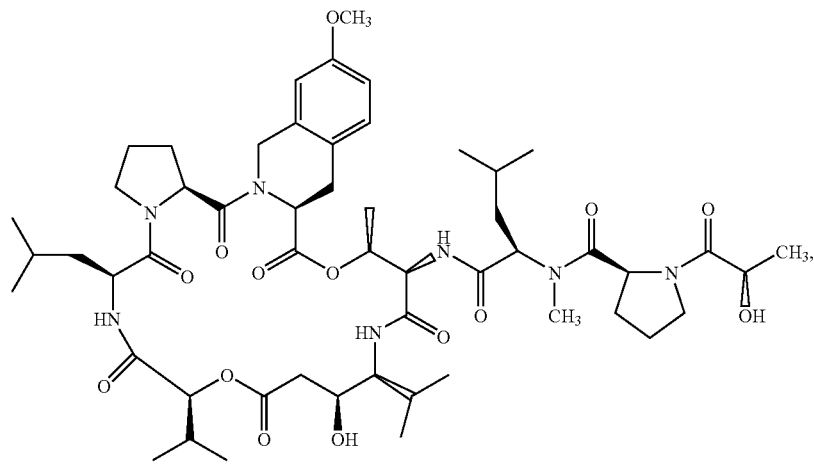
(compound 123)
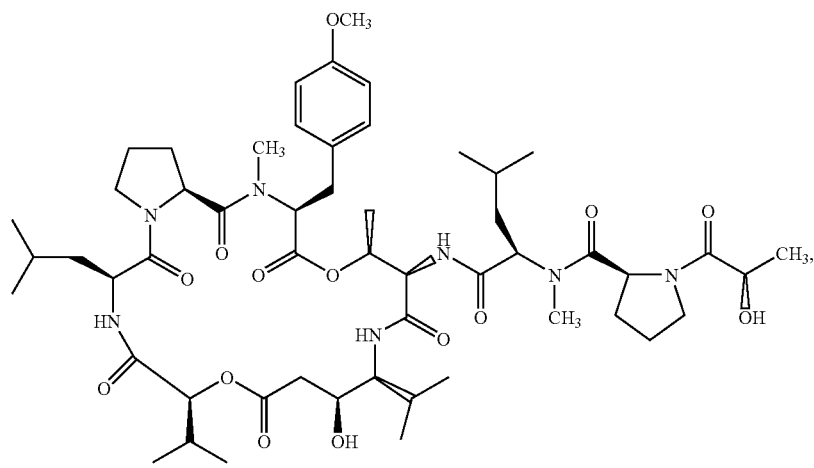
(compound 141)
and
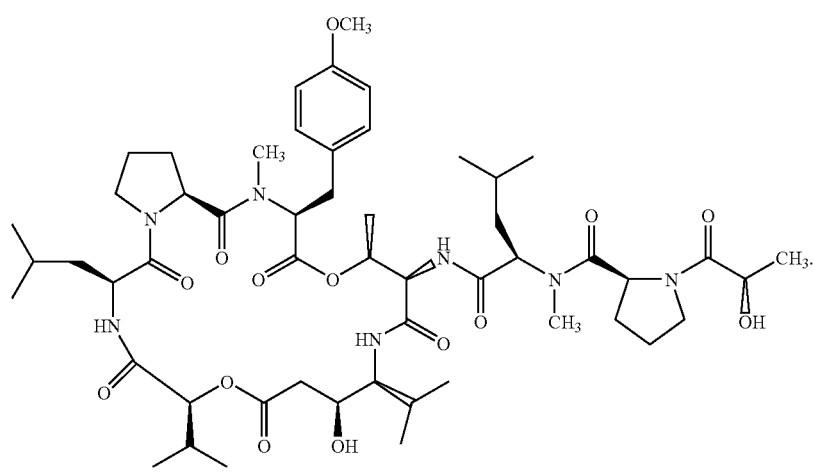
(compound 142)

15. The method of claim 1, wherein R is —(N-methyl)leucine-(S)proline-(S)lactate-(a first fluorophore).
16. The method of claim 15, wherein the didemnin analog is selected from the group consisting of
(compound 107)
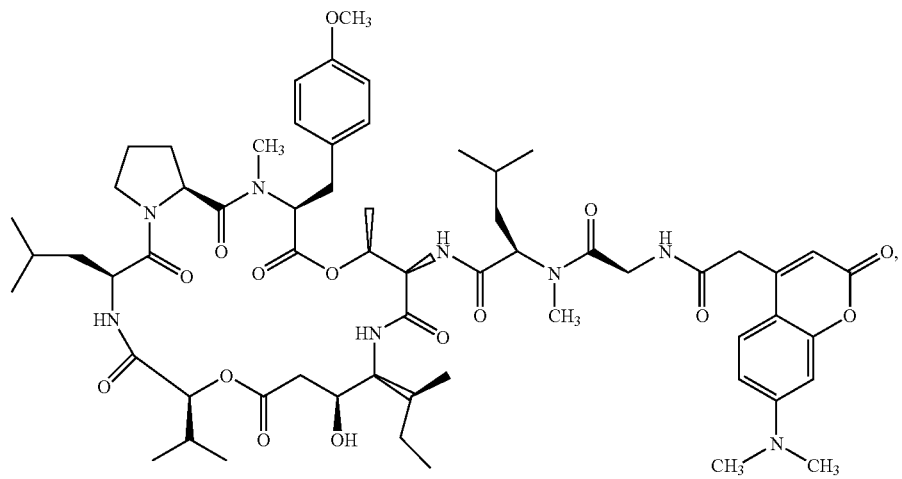
(compound 108)
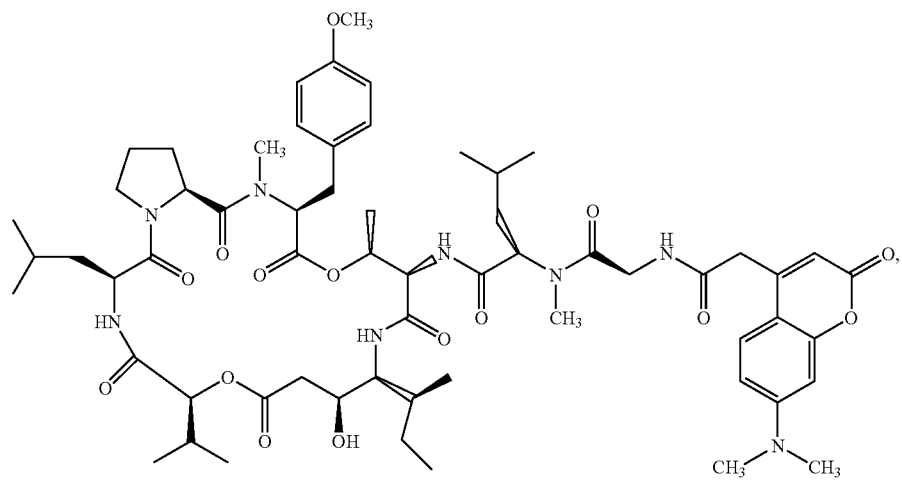
(compound 109)
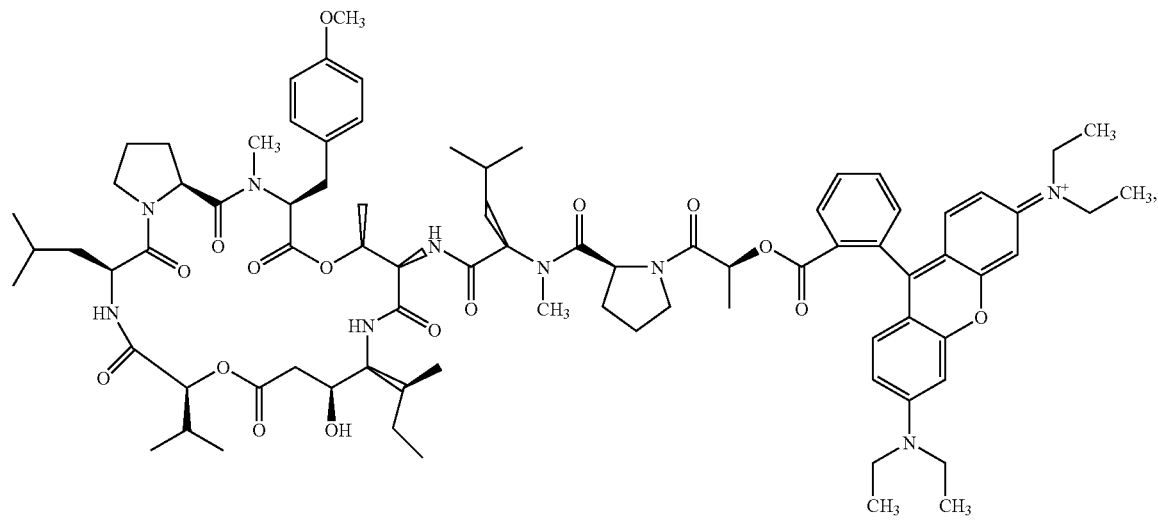
and (compound 110)
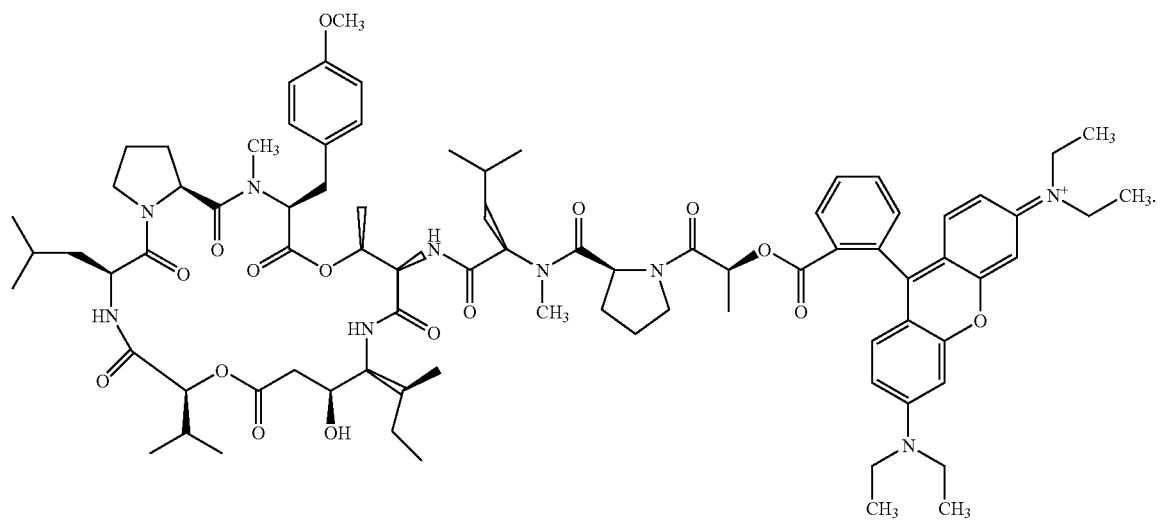
17. The method of claim 1, wherein R² is a second fluorophore and wherein Y is —H.
18. The method of claim 17, wherein the didemnin analog has the following structure, wherein FL is a fluorophore
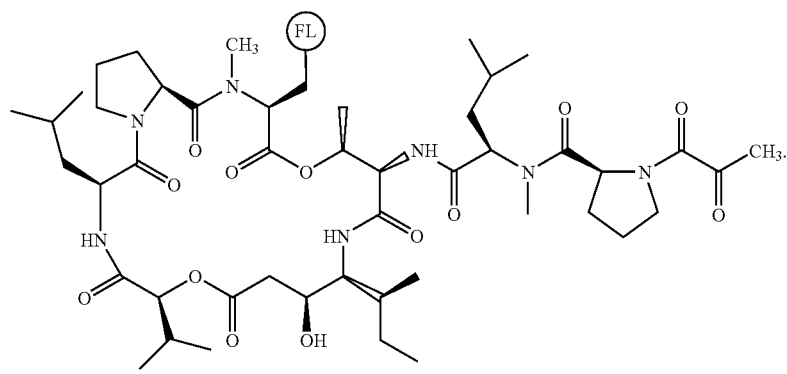
19. The method of claim 1, wherein X is —NH—.
20. The method of claim 19, wherein the didemnin analog is selected from the group consisting of
(compound 124)
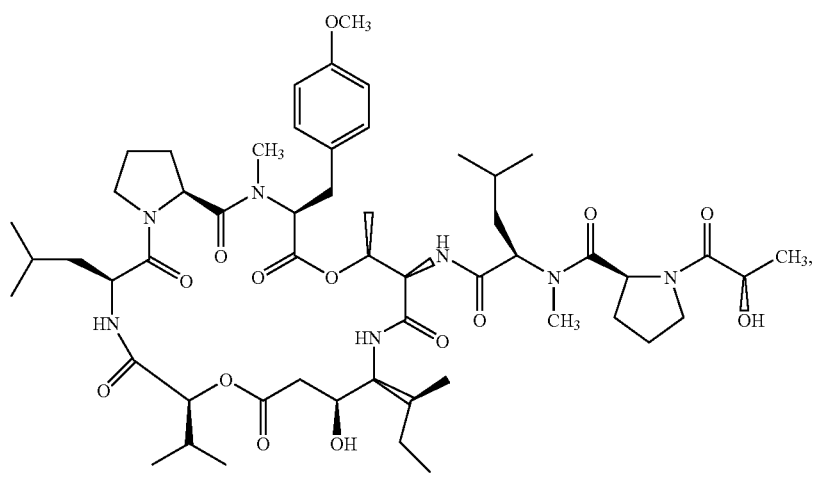

(compound 125)
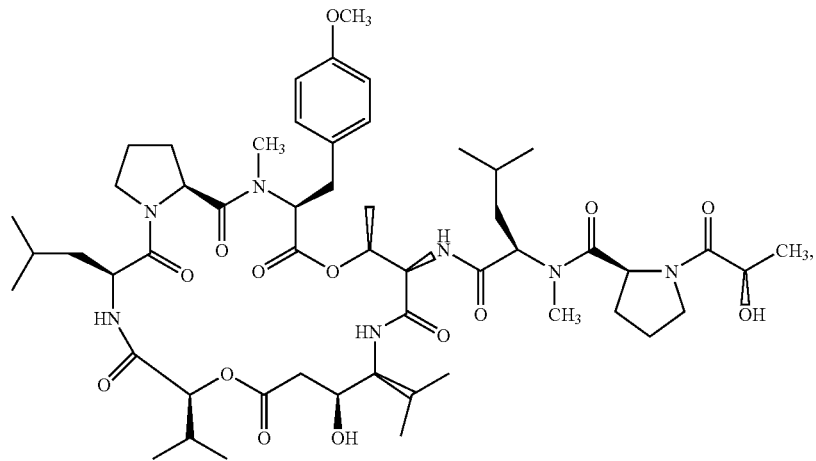
(compound 126)
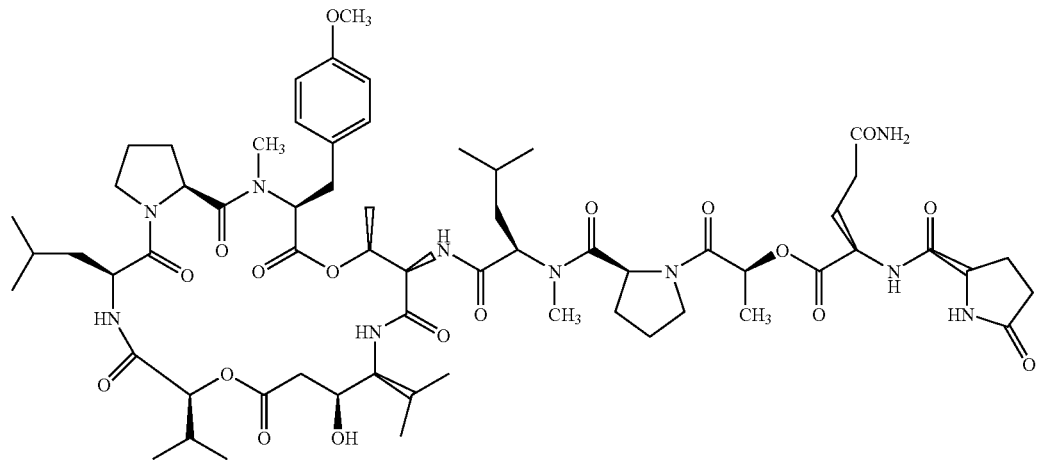
and
(compound 143)
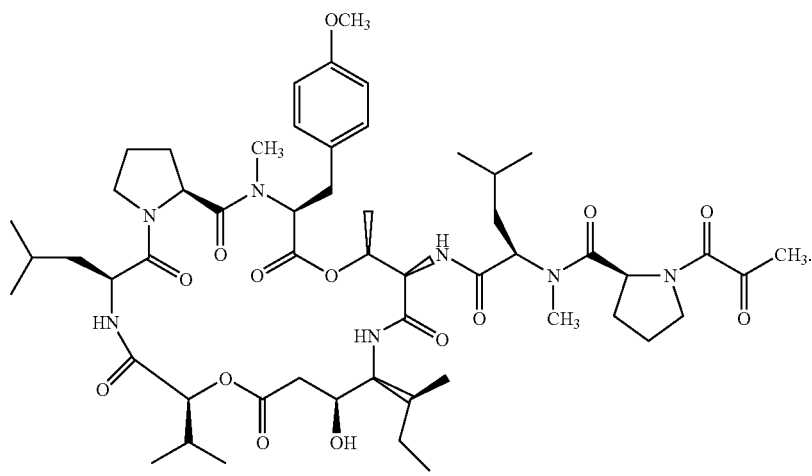

21. A method of performing a function selected from the group consisting of
I) inhibiting protein synthesis in a cell,
II) inhibiting growth of a cell,
III) inhibiting proliferation of a cell,
IV) inhibiting tumorigenesis in a cell, and
V) enhancing apoptosis of a cell,
the method comprising administering to the cell a composition comprising a didemnin fragment having the structure

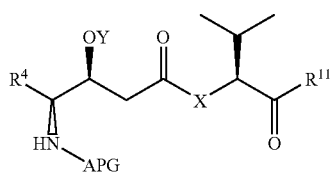

wherein:
i) Y is selected from the group consisting of —H and a hydroxyl protecting group;
ii) X is selected from the group consisting of —O— and —NH—;
iii) $R^4$ is selected from the group consisting of an isoleucine side chain and a valine side chain;
iv) APG is an amine protecting group; and
v) $R^{11}$ is selected from the group consisting of —OH, —NH$_2$, —O(allyl), —O(pentafluorophenyl), and a substituent having the structure

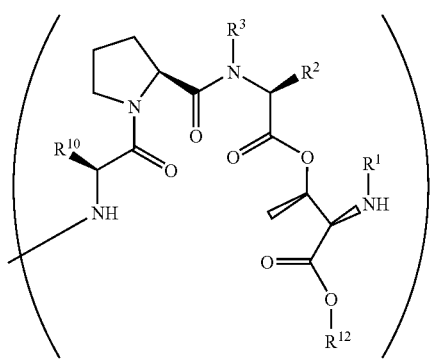

wherein:
a) $R^1$ is selected from the group consisting of —H, and an amine protecting group;
b) $R^2$ and $R^3$ are one of
(I) $R^2$ is selected from the group consisting of an isoleucine side chain, a valine side chain, an alanine side chain, a norleucine side chain, a norvaline side chain, a leucine side chain, a histidine side chain, a tryptophan side chain, an arginine side chain, a lysine side chain, a second fluorophore, and a substituent having the structure

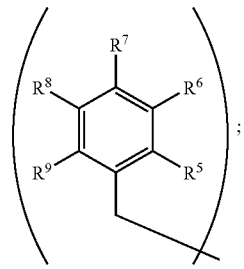

and $R^3$ is selected from the group consisting of —CH$_3$ and —H; or
(II) $R^2$ and $R^3$ together form having the structure

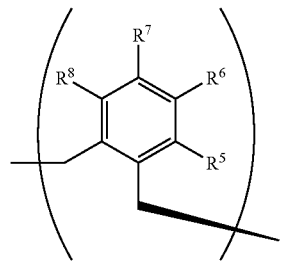

c) each of $R^5$, $R^6$, $R^7$, $R^8$, and $R^9$, when present, is independently selected from the group consisting of —H, —OH, —OCH$_3$, —CO(C$_6$H$_5$), —Br, —I, —F, —Cl, —CH$_3$, and —C$_2$H$_5$;
d) $R^{10}$ is selected from the group consisting of a leucine side chain, a lysine side chain, and a protected lysine side chain; and
e) $R^{12}$ is selected from the group consisting of —H, and -2-(trimethylsilyl).

22. A method of performing a function selected from the group consisting of
I) inhibiting protein synthesis in a cell,
II) inhibiting growth of a cell,
III) inhibiting proliferation of a cell,
IV) inhibiting tumorigenesis in a cell, and
V) enhancing apoptosis of a cell,
the method comprising administering to the cell a didemnin analog having the structure

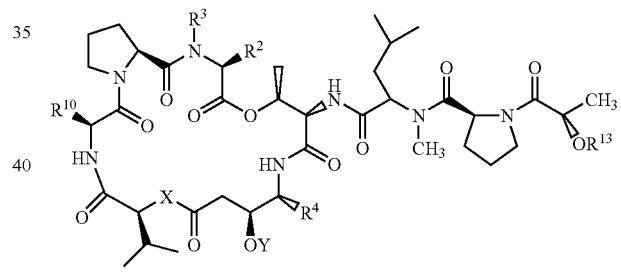

wherein:
i) $R^2$ and $R^3$ are one of
(a) $R^3$ is selected from the group consisting of —CH$_3$ and —H;
$R^2$ is selected from the group consisting of an isoleucine side chain, a valine side chain, an alanine side chain, a norleucine side chain, a norvaline side chain, a leucine side chain, a histidine side chain, a tryptophan side chain, an arginine side chain, a lysine side chain, a second fluorophore, and a substituent having the structure

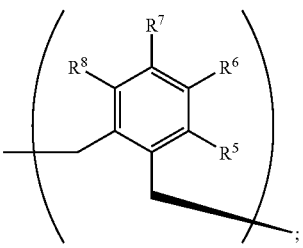

and R³ selected from the group consisting of —CH₃ and —H; or (b) R² and R³ together from the structure

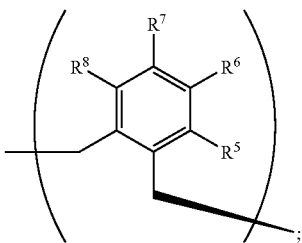

ii) each of R⁵, R⁶, R⁷, R⁸, and R⁹, when present, is independently selected from the group consisting of —H, —OH, —OCH₃, —CO(C₆H₅), —Br, —I, —F, —Cl, —CH₃, and —C₂H₅;
iii) R⁴ is selected from the group consisting of an isoleucine side chain and a valine side chain;
iv) X is selected from the group consisting of —O— and —NH—;
v) Y is selected from the group consisting of —H and a hydroxyl protecting group;
vi) R¹⁰ is selected from the group consisting of a leucine side chain and a lysine side chain; and
vii) R¹³ is an enzyme-cleavable moiety that is cleavable by an enzyme selected from the group consisting of a carboxypeptidase, a beta-lactamase, a beta galactosidase, a penicillin V-amidase, a cytosine deaminase, a nitroreductase, an alkaline phosphatase, a beta-glucuronidase, and a catalytic antibody.

23. The method of claim 22, wherein R¹³ has the structure

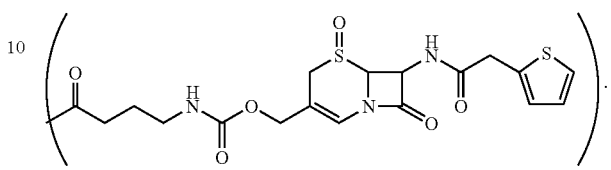

24. The method of claim 22, wherein R¹³ has the structure

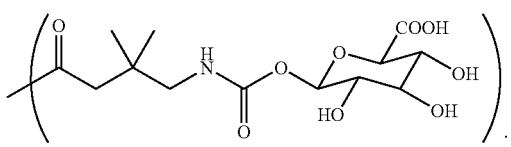

25. The method of claim 22, wherein the didemnin analog is selected from the group consisting of (compound 131)

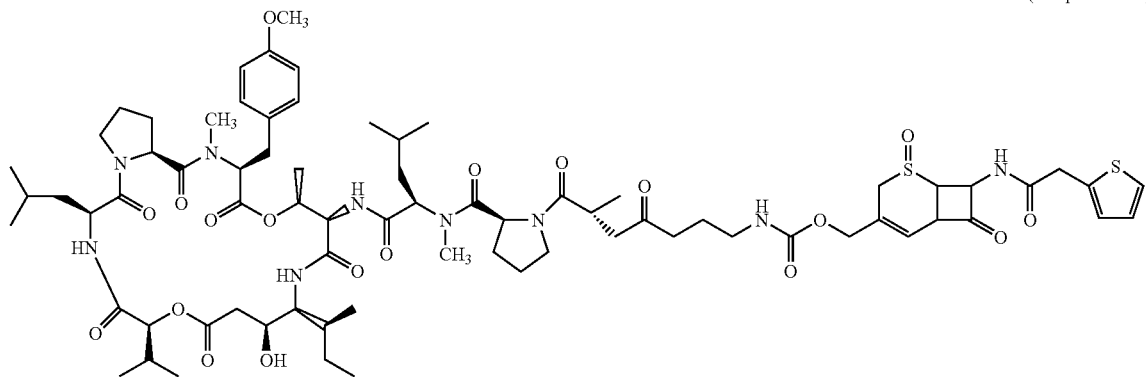

and (compound 132)

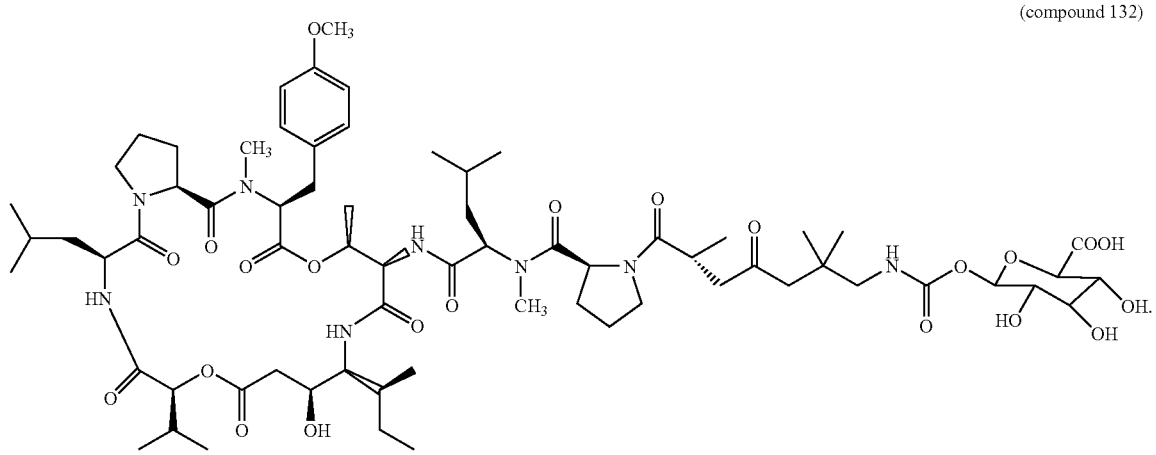

* * * * *